(12) United States Patent
Freeman et al.

(10) Patent No.: US 7,432,059 B2
(45) Date of Patent: Oct. 7, 2008

(54) METHODS OF IDENTIFYING COMPOUNDS THAT UPMODULATE T CELL ACTIVATION IN THE PRESENCE OF A PD-1 MEDIATED SIGNAL

(75) Inventors: Gordon Freeman, Brookline, MA (US); Irene Chernova, Brighton, MA (US); Tatyana Chernova, Mobile, AL (US); Nelly Malenkovich, Boston, MA (US); Clive Wood, Boston, MA (US); Yvette Latchman, Brookline, MA (US); Arlene H. Sharpe, Brookline, MA (US)

(73) Assignees: Dana-Farber Cancer Institute, Inc., Boston, MA (US); Genetics Institute, LLC, Cambridge, MA (US); Brigham and Women's Hospital, Boston, MA (US)

( * ) Notice: Subject to any disclaimer, the term of this patent is extended or adjusted under 35 U.S.C. 154(b) by 0 days.

(21) Appl. No.: 09/895,837

(22) Filed: Jun. 28, 2001

(65) Prior Publication Data
US 2002/0110836 A1    Aug. 15, 2002

Related U.S. Application Data

(60) Provisional application No. 60/214,563, filed on Jun. 28, 2000, provisional application No. 60/270,822, filed on Feb. 23, 2001, provisional application No. 60/271,114, filed on Feb. 23, 2001.

(51) Int. Cl.
*G01N 33/53* (2006.01)
(52) U.S. Cl. ........................................ 435/7.1
(58) Field of Classification Search ............... 435/4, 435/7.1, 7.2, 7.21, 7.24
See application file for complete search history.

(56) References Cited

U.S. PATENT DOCUMENTS 5,698,520 A    12/1997    Honjo et al.

FOREIGN PATENT DOCUMENTS

| WO | WO 01/14557 | A1 | 3/2001 |
|---|---|---|---|
| WO | WO 01/39722 | A2 | 6/2001 |
| WO | WO 01/39722 | A3 | 6/2001 |
| WO | WO 01/83750 | A2 | 11/2001 |
| WO | WO 01/83750 | A3 | 11/2001 |
| WO | WO 01/94413 | A2 | 12/2001 |
| WO | WO 01/94413 | A3 | 12/2001 |
| WO | WO 02/00730 | A2 | 1/2002 |
| WO | WO 02/08279 | A2 | 1/2002 |
| WO | WO 02/08279 | A3 | 1/2002 |

OTHER PUBLICATIONS

Greenwald et al. Cur. Opin. Immunol. 2002; 14:391-396.*
Ishida, Y. et al. "Induced expression of PD-1, a novel member of the immunoglobulin gene superfamily, upon programmed cell death," EMBO J. Nov. 1992;11(11):3887-95.
Krummel, M.F. et al. "CTLA-4 engagement inhibits IL-2 accumulation and cell cycle progression upon activation of resting T cells," J. Exp. Med. Jun. 1, 1996;183(6):2533-40.
Nishimura, H. et al. "Developmentally regulated expression of the PD-1 protein on the surface of double-negative (CD4-CD8-) thymocytes," Int. Immunol. May 1996;8(5):773-80.
Nishimura, H. et al. "Immunological studies on PD-1 deficient mice: implication of PD-1 as a negative regulator for B cell responses," Int. Immunol. Oct. 1998;10(10):1563-72.
Shinohara, T. et al. "Structure and chromosomal localization of the human PD-1 gene (PDCD1)," Genomics Oct. 1994;23(3):704-6.
Walunas, T.L. et al. "CTLA-4 ligation blocks CD28-dependent T cell activation," J. Exp. Med. Jun. 1, 1996;183(6):2541-50.
Agata et al. "Expression of the PD-1 antigen on the surface of stimulated mouse T and B lymphocytes." *Int. Immunol.* May 1996;8(5):765-72.
Dong et al. "B7-H1, a third member of the B7 family, co-stimulates T-cell proliferation and interleukin-10 secretion." *Nat. Med.* Dec. 1999;5(12):1365-9.
Freeman et al. "The B7-homologue, PD-L is the ligand of the PD-1 immunoinhibitory receptor," *FASEB J.* Apr. 20, 2000;14(6):A913.
Freeman et al. "Engagement of the PD-1 immunoinhibitory receptor by a novel B7 family member leads to negative regulation of lymphocyte activation." *J. Exp. Med.* Oct. 2, 2000;192(7):1027-34.
Latchman et al. "PD-L2 is a second ligand for PD-1 and inhibits T cell activation." *Nat. Immunol.* Mar. 2001;2(3):261-8.
Tseng et al. "B7-DC, a new dendritic cell molecule with potent costimulatory properties for T cells." *J. Exp. Med.* Apr. 2, 2001;193(7):839-45.

* cited by examiner

*Primary Examiner*—Ilia Ouspenski
(74) *Attorney, Agent, or Firm*—Foley Hoag LLP

(57) ABSTRACT

The invention provides isolated nucleic acids molecules, designated PD-L2 nucleic acid molecules, which encode novel B7-related molecules which are ligands for PD-1. The invention also provides antisense nucleic acid molecules, recombinant expression vectors containing PD-L2 nucleic acid molecules, host cells into which the expression vectors have been introduced, and nonhuman transgenic animals in which a PD-L2 gene has been introduced or disrupted. The invention further provides isolated PD-L2 polypeptides, fusion proteins, antigenic peptides and anti-PD-L2 antibodies. The invention still further provides methods for promoting or inhibiting the interaction between PD-L2 and PD-1. The invention further provides methods of identifying compounds that upmodulate T cell activation in the presence of a PD-1-mediated signal. Diagnostic and treatment methods utilizing compositions of the invention are also provided.

13 Claims, 17 Drawing Sheets

FIG. 1

Human PD-L2 nucleotide sequence

```
1 GCAAACCTTAAGCTGAATGAACAACTTTTCTTCTCTTGAATATATCTTAACGCCAA
  ATTTTGAGTGCTTTTTTGTTACCCATCCTCATATGTCCCAGCTGGAAAGAATCCTG
  GGTTGGAGCTACTGCATGTTGATTGTTTTGTTTTTCCTTTTGGCTGTTCATTTTGG
  TGGCTACTATAAGGAAATCTAACACAAACAGCAACTGTTTTTTGTTGTTTACTTTT
  GCATCTTTACTTGTGGAGCTGTGGCAAGTCCTCATATCAAATACAGAACATGATCT
  TCCTCCTGCTAATGTTGAGCCTGGAATTGCAGCTTCACCAGATAGCAGCTTTATTC
  ACAGTGACAGTCCCTAAGGAACTGTACATAATAGAGCATGGCAGCAATGTGACCCT
  GGAATGCAACTTTGACACTGGAAGTCATGTGAACCTTGGAGCAATAACAGCCAGTT
  TGCAAAAGGTGGAAAATGATACATCCCCACACCGTGAAAGAGCCACTTTGCTGGAG
  GAGCAGCTGCCCCTAGGGAAGGCCTCGTTCCACATACCTCAAGTCCAAGTGAGGGA
  CGAAGGACAGTACCAATGCATAATCATCTATGGGGTCGCCTGGGACTACAAGTACC
  TGACTCTGAAAGTCAAAGCTTCCTACAGGAAAATAAACACTCACATCCTAAAGGTT
  CCAGAAACAGATGAGGTAGAGCTCACCTGCCAGGCTACAGGTTATCCTCTGGCAGA
  AGTATCCTGGCCAAACGTCAGCGTTCCTGCCAACACCAGCCACTCCAGGACCCCTG
  AAGGCCTCTACCAGGTCACCAGTGTTCTGCGCCTAAAGCCACCCCCTGGCAGAAAC
  TTCAGCTGTGTGTTCTGGAATACTCACGTGAGGGAACTTACTTTGGCCAGCATTGA
  CCTTCAAAGTCAGATGGAACCCAGGACCCATCCAACTTGGCTGCTTCACATTTTCA
  TCCCCTCCTGCATCATTGCTTTCATTTTCATAGCCACAGTGATAGCCCTAAGAAAA
  CAACTCTGTCAAAAGCTGTATTCTTCAAAAGACACAACAAAAAGACCTGTCACCAC
  AACAAAGAGGGAAGTGAACAGTGCTATCTGAACCTGTGGTCTTGGGAGCCAGGGTG
  ACCTGATATGACATCTAAAGAAGCTTCTGGACTCTGAACAAGAATTCGGTGGCCTG
  CAGAGCTTGCCATTTGCACTTTTCAAATGCCTTTGGATGACCCAGCA      1223
```

Human PD-L2 amino acid sequence

```
1 MIFLLLMLSLELQLHQIAALFTVTVPKELYIIEHGSNVTLECNFDTGSHVNLGAIT
  ASLQKVENDTSPHRERATLLEEQLPLGKASFHIPQVQVRDEGQYQCIIIYGVAWDY
  KYLTLKVKASYRKINTHILKVPETDEVELTCQATGYPLAEVSWPNVSVPANTSHSR
  TPEGLYQVTSVLRLKPPPGRNFSCVFWNTHVRELTLASIDLQSQMEPRTHPTWLLH
  IFIPSCIIAFIFIATVIALRKQLCQKLYSSKDTTKRPVTTTKREVNSAI      273
```

FIG. 2

Mouse PD-L2 nucleotide sequence

1 GAATTCGGCACGAGGTCAAATGTGGCATATCTTTGTTGTCTCCTTCTGTCTCCCAA
CTAGAGAGAACACACTTACGGCTCCTGTCCCGGGCAGGTTTGGTTGTCGGTGTGAT
TGGCTTCCAGGGAACCTGATACAAGGAGCAACTGTGTGCTGCCTTTTCTGTGTCTT
TGCTTGAGGAGCTGTGCTGGGTGCTGATATTGACACAGACCATGCTGCTCCTGCTG
CCGATACTGAACCTGAGCTTACAACTTCATCCTGTAGCAGCTTTATTCACCGTGAC
AGCCCCTAAAGAAGTGTACACCGTAGACGTCGGCAGCAGTGTGAGCCTGGAGTGCG
ATTTTGACCGCAGAGAATGCACTGAACTGGAAGGGATAAGAGCCAGTTTGCAGAAG
GTAGAAAATGATACGTCTCTGCAAAGTGAAAGAGCCACCCTGCTGGAGGAGCAGCT
GCCCCTGGGAAAGGCTTTGTTCCACATCCCTAGTGTCCAAGTGAGAGATTCCGGGC
AGTACCGTTGCCTGGTCATCTGCGGGGCCGCCTGGGACTACAAGTACCTGACGGTG
AAAGTCAAAGCTTCTTACATGAGGATAGACACTAGGATCCTGGAGGTTCCAGGTAC
AGGGGAGGTGCAGCTTACCTGCCAGGCTAGAGGTTATCCCCTAGCAGAAGTGTCCT
GGCAAAATGTCAGTGTTCCTGCCAACACCAGCCACATCAGGACCCCCGAAGGCCTC
TACCAGGTCACCAGTGTTCTGCGCCTCAAGCCTCAGCCTAGCAGAAACTTCAGCTG
CATGTTCTGGAATGCTCACATGAAGGAGCTGACTTCAGCCATCATTGACCCTCTGA
GTCGGATGGAACCCAAAGTCCCCAGAACGTGGCCACTTCATGTTTTCATCCCGGCC
TGCACCATCGCTTTGATCTTCCTGGCCATAGTGATAATCCAGAGAAAGAGGATCTA
GGGGAAGCTGTATTACGGAAGAAGTGGTCTCTTCTTCCCAGATCTGGACCTGCGGT
CTTGGGAGTTGGAAGGATCTGATGGGAAACCCTCAAGAGACTTCTGGACTCAAAGT
GAGAATCTTGCAGGACCTGCCATTTGCACTTTTGAACCCTTTGGACGGTGACCCAG
GGCTCCGAAGAGGAGCTTGTAAGACTGACAATCTTCCCTCTGTCTCAAGACTCTCT
GAACAGCAAGACCCCAATGGCACTTTAGACTTACCCCTGGGATCCTGGACCCCAGT
GAGGGCCTAAGGCTCCTAATGACTTTCAGGGTGAGAACAAAAGGAATTGCTCTCCG
CCCCACCCCCACCTCCTGCTTTCCGCAGGGAGACATGGAAATTCCCAGTTACTAAA
ATAGATTGTCAATAGAGTTATTTATAGCCCTCATTTCCTCCGGGGACTTGGAAGCT
TCAGACAGGGTTTTTCATAAACAAAGTCATAACTGATGTGTTTTACAGCATCCTAG
AATCCTGGCAGCCTCTGAAGTTCTAATTAACTGGAAGCATTTAAGCAACACGTCAA
GTGCCCCTGCTGTGGTATTTGTTTCTACTTTTCTGTTTTTAAAGTGTGAGTCACAA
GGTAATTGTTGTAACCTGTGATATCACTGTTTCTTGTGTCTCTTCTTTCAACTACA
TCTTTTAAAACAAAAAAAAAAAAAAAAAAAA                                1655

Mouse PD-L2 amino acid sequence

1 MLLLLPILNLSLQLHPVAALFTVTAPKEVYTVDVGSSVSLECDFDRRECTELEGIR
ASLQKVENDTSLQSERATLLEEQLPLGKALFHIPSVQVRDSGQYRCLVICGAAWDY
KYLTVKVKASYMRIDTRILEVPGTGEVQLTCQARGYPLAEVSWQNVSVPANTSHIR
TPEGLYQVTSVLRLKPQPSRNFSCMFWNAHMKELTSAIIDPLSRMEPKVPRTWPLH
VFIPACTIALIFLAIVIIQRKRI                                         247

Domains Order: signal, IgV, IgC, transmembrane, cytoplasmic

Murine 247 aa

Signal Peptide    MLLLLPILNLSLQLHPVAA

IgV    LFTVTAPKEVYTVDVGSSVSLECDFDRRECTELEGIRASLQKVENDTSLQS
ERATLLEEQLPLGKALFHIPSVQVRDSGQYRCLVICGAAWDYKYLTVKVK

IgC    ASYMRIDTRILEVPGTGEVQLTCQARGYPLAEVSWQNVSVPANTSHIRTPE
GLYQVTSVLRLKPQPSRNFSCMFWNAHMKELTSAIIDPLSRMEPKVPR

} Extracellular

Trans-membrane    TWPLHVFIPACTIALIFLAIVII

Cyto-plasmic    QRKRI

Human 273 aa

Signal peptide    MIFLLLMLSLELQLHQIAA

IgV    LFTVTVPKELYIIEHGSNVTLECNFDTGSHVNLGAITASLQKVENDTSPHR
ERATLLEEQLPLGKASFHIPQVQVRDEGQYQCIIIYGVAWDYKYLTLKVK

IgC    ASYRKINTHILKVPETDEVELTCQATGYPLAEVSWPNVSVPANTSHSRTPE
GLYQVTSVLRLKPPPGRNFSCVFWNTHVRELTLASIDLQSQMEPRTHP

} Extracellular

Trans-membrane    TWLLHIFIPSCIIAFIFIATVIAL

Cyto-plasmic    RKQLCQKLYSSKDTTKRPVTTTKREVNSAI

FIG. 5 murine PD-L2 vs human PD-L2

70% identity

```
mPD-L2:  15  HPVAALFTVTAPKEVYTVDVGSSVSLECDFDRRECTELEGIRASLQKVENDTSLQSERAT  74
             H +AALFTVT PKE+Y ++ GS+V+LEC+FD        L  I ASLQKVENDTS   ERAT
hPD-L2:  15  HQIAALFTVTVPKELYIIEHGSNVTLECNFDTGSHVNLGAITASLQKVENDTSPHRERAT  74 mPD-L2:  75  LLEEQLPLGKALFHIPSVQVRDSGQYRCLVICGAAWDYKYLTVKVKASYMRIDTRILEVP  134
             LLEEQLPLGKA FHIP VQVRD GQY+C++I G AWDYKYLT +KVKASY +I+T IL+VP
hPD-L2:  75  LLEEQLPLGKASFHIPQVQVRDEGQYQCIIIYGVAWDYKYLTLKVKASYRKINTHILKVP  134 mPD-L2: 135  GTGEVQLTCQARGYPLAEVSWQNVSVPANTSHIRTPEGLYQVTSVLRLKPQPSRNFSCMF  194
             T EV+LTCQA GYPLAEVSW NVSVPANTSH RTPEGLYQVTSVLRLKP P RNFSC+F
hPD-L2: 135  ETDEVELTCQATGYPLAEVSWPNVSVPANTSHSRTPEGLYQVTSVLRLKPPPGRNFSCVF  194 mPD-L2: 195  WNAHMKELTSAIIDPLSRMEPKVPRTWPLHVFIPACTIALIFLAIVIIQRKRI  247
             WN H++ELT A ID  S+MEP+    TW LH+FIP+C IA IF+A VI  RK++
hPD-L2: 195  WNTHVRELTTLASIDLQSQMEPRTHPTWLLHIFIPSCIIAFIFIATVIALRKQL  247
```

FIG. 6

```
mPD-L2  MLLLLPILNLSLQLHPVAALFTVTAPKEVYTVDVGSSVSLECDFDRRECTELEGI.....
hPD-L2  MIFLLLMLSLELQLHQIAALFTVTVPKELYIIEHGSNVTLECNFDTGSHVNLGAI.....
mPD-L1  ~MRIFAGIIFTACCHLLRA.FTITAPKDLYVVEYGSNVTMECRFPVERELDLLALVVYWE
hPD-L1  ~MRIFAVFIFMTYWHLLNA.FTVTVPKDLYVVEYGSNMTIECKFPVEKQLDLAALIVYWE
        1........10........20........30........40........50........

mPD-L2  ...RASLQKV..ENDTSLQ....SERATLLEEQLPLGKALFHIPSVQVRDSGQYRCLVIC
hPD-L2  ...TASLQKV..ENDTSPH....RERATLLEEQLPLGKASFHIPQVQVRDGQYQCIIIY
mPD-L1  KEDEQVIQFVAGEEDLKPQHSNFRGRASLPKDQLLKGNAALQITDVKLQDAGVYCCIISY
hPD-L1  MEDKNIIQFVHGEEDLKVQHSSYRQRARLLKDQLSLGNAALQITDVKLQDAGVYRCMISY
        61.......70........80........90........100.......110........

mPD-L2  GAAWDYKYLTVKVKASYMRIDTRILEV.PGTGEVQLTCQARGYPLAEVSWQN.....VSV
hPD-L2  GVAWDYKYLTLKVKASYRKINTHILKV.PETDEVELTCQATGYPLAEVSWPN.....VSV
mPD-L1  GGA.DYKRITLKVNAPYRKINQRI.SVDPATSEHELICQAEGYPEAEVIWTNSDHQPVSG
hPD-L1  GGA.DYKRITVKVNAPYNKINQRILVVDPVTSEHELTCQAEGYPKAEVIWTSSDHQVLSG
        121......130.......140.......150.......160.......170........

mPD-L2  PANTSHIRTPEGLYQVTSVLRLKPQPSRNFSCMFWNAHMKELTSA...IIDPLSRMEPKVP
hPD-L2  PANTSHSRTPEGLYQVTSVLRLKPPPGRNFSCVFWNTHVRELTLA...SIDLQSQMEPRTH
mPD-L1  KRSVTTSRTEGMLLNVTSSLRVNATANDVFYCTFWRSQPGQNHTAELIIPELPATHPPQN
hPD-L1  KTTTTNSKREEKLFNVTSTLRINTTTNEIFYCTFRRLDPEENHTAELVIPELPLAHPPNE
        181......190.......200.......210.......220.......230........

mPD-L2  RTWPLHVFIPACTIALIFLAIVIIQRKRI~~~~~~~~~~~~~~~~~~~~~~~~~~~~~~
hPD-L2  PTWLLHIFIPSCIIAFIFIATVIALRKQLCQKLYSSKDTTKRPVTTTKREVNSAI~~
mPD-L1  RT...HWVLLGSILLFLIVVSTVLLFLRKQVRMLDVEKCGVEDTSSKNRNDTQFEET
hPD-L1  RT...HLVTLGAILLCLGVALTFIFRLRKG.RMMDVKKCGIQDTNSKKQSDTHLEET
        241......250.......260.......270.......280.......290.....
```

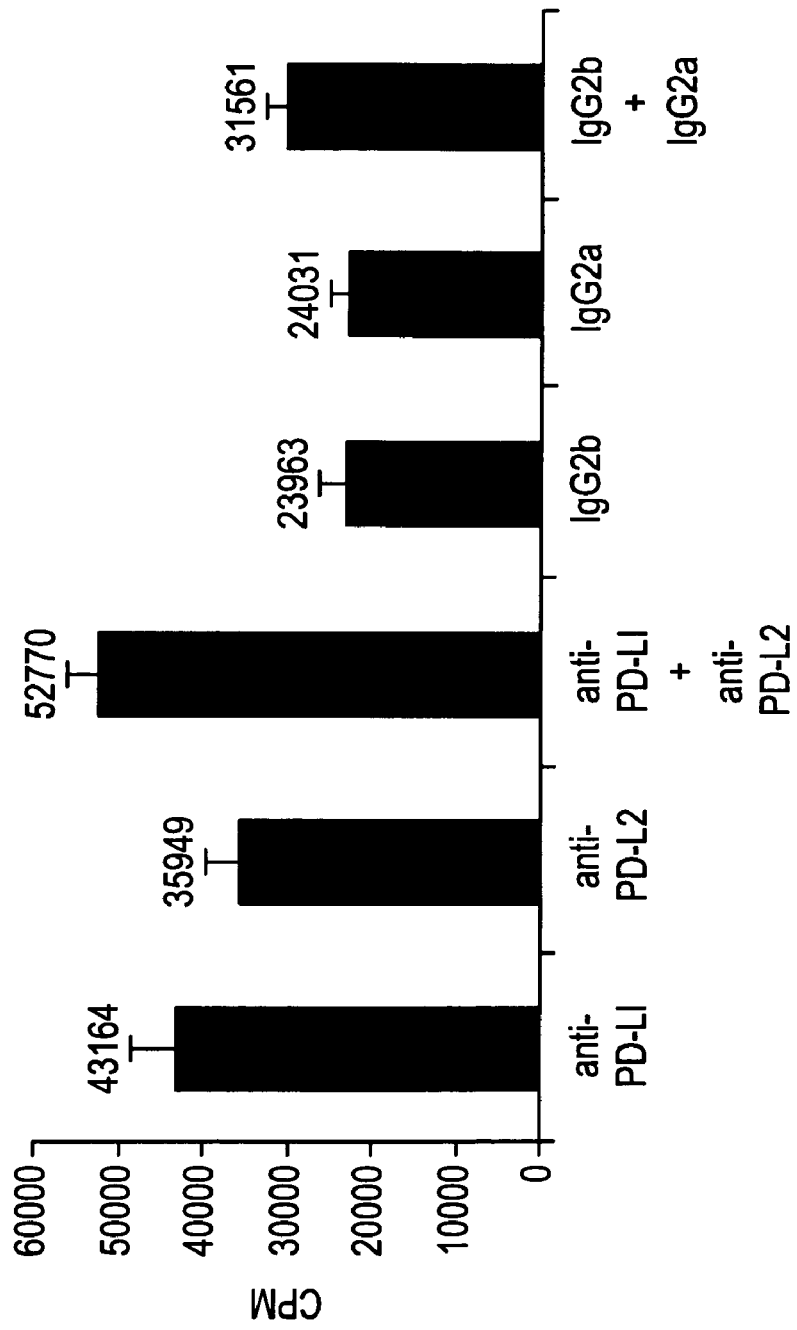

SEQUENCE LISTING

```
<160> NUMBER OF SEQ ID NOS: 12

<210> SEQ ID NO 1
<211> LENGTH: 1223
<212> TYPE: DNA
<213> ORGANISM: Homo sapiens
<220> FEATURE:
<221> NAME/KEY: CDS
<222> LOCATION: (274)...(1092)

<400> SEQUENCE: 1
gcaaacctta agctgaatga acaactttc ttctcttgaa tatatcttaa cgccaaattt         60
tgagtgcttt tttgttaccc atcctcatat gtcccagctg gaaagaatcc tgggttggag       120
ctactgcatg ttgattgttt tgtttttcct tttggctgtt cattttggtg gctactataa       180
ggaaatctaa cacaaacagc aactgttttt tgttgtttac ttttgcatct ttacttgtgg       240
agctgtggca agtcctcata tcaaatacag aac atg atc ttc ctc ctg cta atg        294
                                    Met Ile Phe Leu Leu Leu Met
                                     1               5
```

```
ttg agc ctg gaa ttg cag ctt cac cag ata gca gct tta ttc aca gtg      342
Leu Ser Leu Glu Leu Gln Leu His Gln Ile Ala Ala Leu Phe Thr Val
        10                  15                  20 aca gtc cct aag gaa ctg tac ata ata gag cat ggc agc aat gtg acc      390
Thr Val Pro Lys Glu Leu Tyr Ile Ile Glu His Gly Ser Asn Val Thr
25                  30                  35 ctg gaa tgc aac ttt gac act gga agt cat gtg aac ctt gga gca ata      438
Leu Glu Cys Asn Phe Asp Thr Gly Ser His Val Asn Leu Gly Ala Ile
 40                  45                  50                  55 aca gcc agt ttg caa aag gtg gaa aat gat aca tcc cca cac cgt gaa      486
Thr Ala Ser Leu Gln Lys Val Glu Asn Asp Thr Ser Pro His Arg Glu
                 60                  65                  70 aga gcc act ttg ctg gag gag cag ctg ccc cta ggg aag gcc tcg ttc      534
Arg Ala Thr Leu Leu Glu Glu Gln Leu Pro Leu Gly Lys Ala Ser Phe
             75                  80                  85 cac ata cct caa gtc caa gtg agg gac gaa gga cag tac caa tgc ata      582
His Ile Pro Gln Val Gln Val Arg Asp Glu Gly Gln Tyr Gln Cys Ile
         90                  95                 100 atc atc tat ggg gtc gcc tgg gac tac aag tac ctg act ctg aaa gtc      630
Ile Ile Tyr Gly Val Ala Trp Asp Tyr Lys Tyr Leu Thr Leu Lys Val
     105                 110                 115 aaa gct tcc tac agg aaa ata aac act cac atc cta aag gtt cca gaa      678
Lys Ala Ser Tyr Arg Lys Ile Asn Thr His Ile Leu Lys Val Pro Glu
120                 125                 130                 135 aca gat gag gta gag ctc acc tgc cag gct aca ggt tat cct ctg gca      726
Thr Asp Glu Val Glu Leu Thr Cys Gln Ala Thr Gly Tyr Pro Leu Ala
                140                 145                 150 gaa gta tcc tgg cca aac gtc agc gtt cct gcc aac acc agc cac tcc      774
Glu Val Ser Trp Pro Asn Val Ser Val Pro Ala Asn Thr Ser His Ser
            155                 160                 165 agg acc cct gaa ggc ctc tac cag gtc acc agt gtt ctg cgc cta aag      822
Arg Thr Pro Glu Gly Leu Tyr Gln Val Thr Ser Val Leu Arg Leu Lys
        170                 175                 180 cca ccc cct ggc aga aac ttc agc tgt gtg ttc tgg aat act cac gtg      870
Pro Pro Pro Gly Arg Asn Phe Ser Cys Val Phe Trp Asn Thr His Val
    185                 190                 195 agg gaa ctt act ttg gcc agc att gac ctt caa agt cag atg gaa ccc      918
Arg Glu Leu Thr Leu Ala Ser Ile Asp Leu Gln Ser Gln Met Glu Pro
200                 205                 210                 215 agg acc cat cca act tgg ctg ctt cac att ttc atc ccc tcc tgc atc      966
Arg Thr His Pro Thr Trp Leu Leu His Ile Phe Ile Pro Ser Cys Ile
                220                 225                 230 att gct ttc att ttc ata gcc aca gtg ata gcc cta aga aaa caa ctc     1014
Ile Ala Phe Ile Phe Ile Ala Thr Val Ile Ala Leu Arg Lys Gln Leu
            235                 240                 245 tgt caa aag ctg tat tct tca aaa gac aca aca aaa aga cct gtc acc     1062
Cys Gln Lys Leu Tyr Ser Ser Lys Asp Thr Thr Lys Arg Pro Val Thr
        250                 255                 260 aca aca aag agg gaa gtg aac agt gct atc tgaacctgtg gtcttgggag       1112
Thr Thr Lys Arg Glu Val Asn Ser Ala Ile
    265                 270 ccagggtgac ctgatatgac atctaaagaa gcttctggac tctgaacaag aattcggtgg   1172
cctgcagagc ttgccatttg cacttttcaa atgcctttgg atgacccagc a            1223

<210> SEQ ID NO 2
<211> LENGTH: 273
<212> TYPE: PRT
<213> ORGANISM: Homo sapiens

<400> SEQUENCE: 2
```

```
Met Ile Phe Leu Leu Leu Met Leu Ser Leu Glu Leu Gln Leu His Gln
 1               5                  10                  15

Ile Ala Ala Leu Phe Thr Val Thr Val Pro Lys Glu Leu Tyr Ile Ile
             20                  25                  30

Glu His Gly Ser Asn Val Thr Leu Glu Cys Asn Phe Asp Thr Gly Ser
             35                  40                  45

His Val Asn Leu Gly Ala Ile Thr Ala Ser Leu Gln Lys Val Glu Asn
 50                  55                  60

Asp Thr Ser Pro His Arg Glu Arg Ala Thr Leu Leu Glu Glu Gln Leu
65                   70                  75                  80

Pro Leu Gly Lys Ala Ser Phe His Ile Pro Gln Val Gln Val Arg Asp
                 85                  90                  95

Glu Gly Gln Tyr Gln Cys Ile Ile Ile Tyr Gly Val Ala Trp Asp Tyr
             100                 105                 110

Lys Tyr Leu Thr Leu Lys Val Lys Ala Ser Tyr Arg Lys Ile Asn Thr
             115                 120                 125

His Ile Leu Lys Val Pro Glu Thr Asp Glu Val Glu Leu Thr Cys Gln
130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                 165                 170                 175

Thr Ser Val Leu Arg Leu Lys Pro Pro Pro Gly Arg Asn Phe Ser Cys
             180                 185                 190

Val Phe Trp Asn Thr His Val Arg Glu Leu Thr Leu Ala Ser Ile Asp
             195                 200                 205

Leu Gln Ser Gln Met Glu Pro Arg Thr His Pro Thr Trp Leu Leu His
210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                 245                 250                 255

Thr Thr Lys Arg Pro Val Thr Thr Thr Lys Arg Glu Val Asn Ser Ala
                 260                 265                 270

Ile

<210> SEQ ID NO 3
<211> LENGTH: 819
<212> TYPE: DNA
<213> ORGANISM: Homo sapiens
<220> FEATURE:
<221> NAME/KEY: CDS
<222> LOCATION: (1)...(819)

<400> SEQUENCE: 3 atg atc ttc ctc ctg cta atg ttg agc ctg gaa ttg cag ctt cac cag      48
Met Ile Phe Leu Leu Leu Met Leu Ser Leu Glu Leu Gln Leu His Gln
 1               5                  10                  15 ata gca gct tta ttc aca gtg aca gtc cct aag gaa ctg tac ata ata      96
Ile Ala Ala Leu Phe Thr Val Thr Val Pro Lys Glu Leu Tyr Ile Ile
             20                  25                  30 gag cat ggc agc aat gtg acc ctg gaa tgc aac ttt gac act gga agt     144
Glu His Gly Ser Asn Val Thr Leu Glu Cys Asn Phe Asp Thr Gly Ser
             35                  40                  45 cat gtg aac ctt gga gca ata aca gcc agt ttg caa aag gtg gaa aat     192
His Val Asn Leu Gly Ala Ile Thr Ala Ser Leu Gln Lys Val Glu Asn
```

|  |  |  |  |  |  |  |  |  |  |  |  |  |  |  |  |
|---|---|---|---|---|---|---|---|---|---|---|---|---|---|---|---|
|  |  | 50 |  |  |  | 55 |  |  |  | 60 |  |  |  |  |  |
| gat | aca | tcc | cca | cac | cgt | gaa | aga | gcc | act | ttg | ctg | gag | gag | cag | ctg | 240 |
| Asp | Thr | Ser | Pro | His | Arg | Glu | Arg | Ala | Thr | Leu | Leu | Glu | Glu | Gln | Leu |  |
| 65 |  |  |  |  | 70 |  |  |  |  | 75 |  |  |  |  | 80 |  |
| ccc | cta | ggg | aag | gcc | tcg | ttc | cac | ata | cct | caa | gtc | caa | gtg | agg | gac | 288 |
| Pro | Leu | Gly | Lys | Ala | Ser | Phe | His | Ile | Pro | Gln | Val | Gln | Val | Arg | Asp |  |
|  |  |  |  | 85 |  |  |  |  | 90 |  |  |  |  | 95 |  |  |
| gaa | gga | cag | tac | caa | tgc | ata | atc | atc | tat | ggg | gtc | gcc | tgg | gac | tac | 336 |
| Glu | Gly | Gln | Tyr | Gln | Cys | Ile | Ile | Ile | Tyr | Gly | Val | Ala | Trp | Asp | Tyr |  |
|  |  |  | 100 |  |  |  |  | 105 |  |  |  |  | 110 |  |  |  |
| aag | tac | ctg | act | ctg | aaa | gtc | aaa | gct | tcc | tac | agg | aaa | ata | aac | act | 384 |
| Lys | Tyr | Leu | Thr | Leu | Lys | Val | Lys | Ala | Ser | Tyr | Arg | Lys | Ile | Asn | Thr |  |
|  | 115 |  |  |  |  | 120 |  |  |  |  | 125 |  |  |  |  |  |
| cac | atc | cta | aag | gtt | cca | gaa | aca | gat | gag | gta | gag | ctc | acc | tgc | cag | 432 |
| His | Ile | Leu | Lys | Val | Pro | Glu | Thr | Asp | Glu | Val | Glu | Leu | Thr | Cys | Gln |  |
| 130 |  |  |  |  | 135 |  |  |  |  | 140 |  |  |  |  |  |  |
| gct | aca | ggt | tat | cct | ctg | gca | gaa | gta | tcc | tgg | cca | aac | gtc | agc | gtt | 480 |
| Ala | Thr | Gly | Tyr | Pro | Leu | Ala | Glu | Val | Ser | Trp | Pro | Asn | Val | Ser | Val |  |
| 145 |  |  |  |  | 150 |  |  |  |  | 155 |  |  |  |  | 160 |  |
| cct | gcc | aac | acc | agc | cac | tcc | agg | acc | cct | gaa | ggc | ctc | tac | cag | gtc | 528 |
| Pro | Ala | Asn | Thr | Ser | His | Ser | Arg | Thr | Pro | Glu | Gly | Leu | Tyr | Gln | Val |  |
|  |  |  |  | 165 |  |  |  |  | 170 |  |  |  |  | 175 |  |  |
| acc | agt | gtt | ctg | cgc | cta | aag | cca | ccc | cct | ggc | aga | aac | ttc | agc | tgt | 576 |
| Thr | Ser | Val | Leu | Arg | Leu | Lys | Pro | Pro | Pro | Gly | Arg | Asn | Phe | Ser | Cys |  |
|  |  |  | 180 |  |  |  |  | 185 |  |  |  |  | 190 |  |  |  |
| gtg | ttc | tgg | aat | act | cac | gtg | agg | gaa | ctt | act | ttg | gcc | agc | att | gac | 624 |
| Val | Phe | Trp | Asn | Thr | His | Val | Arg | Glu | Leu | Thr | Leu | Ala | Ser | Ile | Asp |  |
|  | 195 |  |  |  |  | 200 |  |  |  |  | 205 |  |  |  |  |  |
| ctt | caa | agt | cag | atg | gaa | ccc | agg | acc | cat | cca | act | tgg | ctg | ctt | cac | 672 |
| Leu | Gln | Ser | Gln | Met | Glu | Pro | Arg | Thr | His | Pro | Thr | Trp | Leu | Leu | His |  |
| 210 |  |  |  |  | 215 |  |  |  |  | 220 |  |  |  |  |  |  |
| att | ttc | atc | ccc | tcc | tgc | atc | att | gct | ttc | att | ttc | ata | gcc | aca | gtg | 720 |
| Ile | Phe | Ile | Pro | Ser | Cys | Ile | Ile | Ala | Phe | Ile | Phe | Ile | Ala | Thr | Val |  |
| 225 |  |  |  |  | 230 |  |  |  |  | 235 |  |  |  |  | 240 |  |
| ata | gcc | cta | aga | aaa | caa | ctc | tgt | caa | aag | ctg | tat | tct | tca | aaa | gac | 768 |
| Ile | Ala | Leu | Arg | Lys | Gln | Leu | Cys | Gln | Lys | Leu | Tyr | Ser | Ser | Lys | Asp |  |
|  |  |  |  | 245 |  |  |  |  | 250 |  |  |  |  | 255 |  |  |
| aca | aca | aaa | aga | cct | gtc | acc | aca | aca | aag | agg | gaa | gtg | aac | agt | gct | 816 |
| Thr | Thr | Lys | Arg | Pro | Val | Thr | Thr | Thr | Lys | Arg | Glu | Val | Asn | Ser | Ala |  |
|  |  |  | 260 |  |  |  |  | 265 |  |  |  |  | 270 |  |  |  |
| atc |  |  |  |  |  |  |  |  |  |  |  |  |  |  |  | 819 |
| Ile |  |  |  |  |  |  |  |  |  |  |  |  |  |  |  |  |

<210> SEQ ID NO 4
<211> LENGTH: 1655
<212> TYPE: DNA
<213> ORGANISM: Mus musculus
<220> FEATURE:
<221> NAME/KEY: CDS
<222> LOCATION: (210)...(950)

<400> SEQUENCE: 4

| gaattcggca cgaggtcaaa tgtggcatat ctttgttgtc tccttctgtc tcccaactag | 60 |
|---|---|
| agagaacaca cttacggctc ctgtcccggg caggtttggt tgtcggtgtg attggcttcc | 120 |
| agggaacctg atacaaggag caactgtgtg ctgccttttc tgtgtctttg cttgaggagc | 180 |

| tgtgctgggt gctgatattg acacagacc | atg ctg ctc ctg ctg ccg ata ctg | 233 |
|---|---|---|
|  | Met Leu Leu Leu Leu Pro Ile Leu |  |
|  | 1               5 |  |

| aac ctg agc tta caa ctt cat cct gta gca gct tta ttc acc gtg aca | 281 |
|---|---|

```
                Asn Leu Ser Leu Gln Leu His Pro Val Ala Ala Leu Phe Thr Val Thr
                     10                  15                  20 gcc cct aaa gaa gtg tac acc gta gac gtc ggc agc agt gtg agc ctg            329
Ala Pro Lys Glu Val Tyr Thr Val Asp Val Gly Ser Ser Val Ser Leu
 25              30                  35                  40 gag tgc gat ttt gac cgc aga gaa tgc act gaa ctg gaa ggg ata aga            377
Glu Cys Asp Phe Asp Arg Arg Glu Cys Thr Glu Leu Glu Gly Ile Arg
                 45                  50                  55 gcc agt ttg cag aag gta gaa aat gat acg tct ctg caa agt gaa aga            425
Ala Ser Leu Gln Lys Val Glu Asn Asp Thr Ser Leu Gln Ser Glu Arg
             60                  65                  70 gcc acc ctg ctg gag gag cag ctg ccc ctg gga aag gct ttg ttc cac            473
Ala Thr Leu Leu Glu Glu Gln Leu Pro Leu Gly Lys Ala Leu Phe His
         75                  80                  85 atc cct agt gtc caa gtg aga gat tcc ggg cag tac cgt tgc ctg gtc            521
Ile Pro Ser Val Gln Val Arg Asp Ser Gly Gln Tyr Arg Cys Leu Val
     90                  95                 100 atc tgc ggg gcc gcc tgg gac tac aag tac ctg acg gtg aaa gtc aaa            569
Ile Cys Gly Ala Ala Trp Asp Tyr Lys Tyr Leu Thr Val Lys Val Lys
105                 110                 115                 120 gct tct tac atg agg ata gac act agg atc ctg gag gtt cca ggt aca            617
Ala Ser Tyr Met Arg Ile Asp Thr Arg Ile Leu Glu Val Pro Gly Thr
                125                 130                 135 ggg gag gtg cag ctt acc tgc cag gct aga ggt tat ccc cta gca gaa            665
Gly Glu Val Gln Leu Thr Cys Gln Ala Arg Gly Tyr Pro Leu Ala Glu
            140                 145                 150 gtg tcc tgg caa aat gtc agt gtt cct gcc aac acc agc cac atc agg            713
Val Ser Trp Gln Asn Val Ser Val Pro Ala Asn Thr Ser His Ile Arg
        155                 160                 165 acc ccc gaa ggc ctc tac cag gtc acc agt gtt ctg cgc ctc aag cct            761
Thr Pro Glu Gly Leu Tyr Gln Val Thr Ser Val Leu Arg Leu Lys Pro
    170                 175                 180 cag cct agc aga aac ttc agc tgc atg ttc tgg aat gct cac atg aag            809
Gln Pro Ser Arg Asn Phe Ser Cys Met Phe Trp Asn Ala His Met Lys
185                 190                 195                 200 gag ctg act tca gcc atc att gac cct ctg agt cgg atg gaa ccc aaa            857
Glu Leu Thr Ser Ala Ile Ile Asp Pro Leu Ser Arg Met Glu Pro Lys
                205                 210                 215 gtc ccc aga acg tgg cca ctt cat gtt ttc atc ccg gcc tgc acc atc            905
Val Pro Arg Thr Trp Pro Leu His Val Phe Ile Pro Ala Cys Thr Ile
            220                 225                 230 gct ttg atc ttc ctg gcc ata gtg ata atc cag aga aag agg atc                950
Ala Leu Ile Phe Leu Ala Ile Val Ile Ile Gln Arg Lys Arg Ile
        235                 240                 245 tagggaagc tgtattacgg aagaagtggt ctcttcttcc cagatctgga cctgcggtct         1010
tgggagttgg aaggatctga tgggaaaccc tcaagagact tctggactca aagtgagaat        1070
cttgcaggac ctgccatttg cacttttgaa ccctttggac ggtgacccag ggctccgaag        1130
aggagcttgt aagactgaca atcttccctc tgtctcaaga ctctctgaac agcaagaccc        1190
caatggcact ttagacttac ccctgggatc ctggaccca gtgagggcct aaggctccta         1250
atgactttca gggtgagaac aaaaggaatt gctctccgcc ccaccccac ctcctgcttt         1310 ccgcagggag acatggaaat tcccagttac taaaatagat tgtcaataga gttatttata       1370
gccctcattt cctccgggga cttggaagct tcagacaggg ttttcataa acaaagtcat         1430 aactgatgtg ttttacagca tcctagaatc ctggcagcct ctgaagttct aattaactgg       1490
aagcatttaa gcaacacgtc aagtgcccct gctgtggtat ttgtttctac ttttctgttt       1550
```

```
ttaaagtgtg agtcacaagg taattgttgt aacctgtgat atcactgttt cttgtgtctc      1610
ttctttcaac tacatctttt aaacaaaaa  aaaaaaaaa  aaaaa                       1655
```

<210> SEQ ID NO 5
<211> LENGTH: 247
<212> TYPE: PRT
<213> ORGANISM: Mus musculus

<400> SEQUENCE: 5

```
Met Leu Leu Leu Leu Pro Ile Leu Asn Leu Ser Leu Gln Leu His Pro
 1               5                  10                  15

Val Ala Ala Leu Phe Thr Val Thr Ala Pro Lys Glu Val Tyr Thr Val
                20                  25                  30

Asp Val Gly Ser Ser Val Ser Leu Glu Cys Asp Phe Asp Arg Arg Glu
            35                  40                  45

Cys Thr Glu Leu Glu Gly Ile Arg Ala Ser Leu Gln Lys Val Glu Asn
        50                  55                  60

Asp Thr Ser Leu Gln Ser Glu Arg Ala Thr Leu Leu Glu Glu Gln Leu
65                  70                  75                  80

Pro Leu Gly Lys Ala Leu Phe His Ile Pro Ser Val Gln Val Arg Asp
                85                  90                  95

Ser Gly Gln Tyr Arg Cys Leu Val Ile Cys Gly Ala Ala Trp Asp Tyr
            100                 105                 110

Lys Tyr Leu Thr Val Lys Val Lys Ala Ser Tyr Met Arg Ile Asp Thr
        115                 120                 125

Arg Ile Leu Glu Val Pro Gly Thr Gly Glu Val Gln Leu Thr Cys Gln
    130                 135                 140

Ala Arg Gly Tyr Pro Leu Ala Glu Val Ser Trp Gln Asn Val Ser Val
145                 150                 155                 160

Pro Ala Asn Thr Ser His Ile Arg Thr Pro Glu Gly Leu Tyr Gln Val
                165                 170                 175

Thr Ser Val Leu Arg Leu Lys Pro Gln Pro Ser Arg Asn Phe Ser Cys
            180                 185                 190

Met Phe Trp Asn Ala His Met Lys Glu Leu Thr Ser Ala Ile Ile Asp
        195                 200                 205

Pro Leu Ser Arg Met Glu Pro Lys Val Pro Arg Thr Trp Pro Leu His
    210                 215                 220

Val Phe Ile Pro Ala Cys Thr Ile Ala Leu Ile Phe Leu Ala Ile Val
225                 230                 235                 240

Ile Ile Gln Arg Lys Arg Ile
                245
```

<210> SEQ ID NO 6
<211> LENGTH: 741
<212> TYPE: DNA
<213> ORGANISM: Mus musculus
<220> FEATURE:
<221> NAME/KEY: CDS
<222> LOCATION: (1)...(741)

<400> SEQUENCE: 6

```
atg ctg ctc ctg ctg ccg ata ctg aac ctg agc tta caa ctt cat cct       48
Met Leu Leu Leu Leu Pro Ile Leu Asn Leu Ser Leu Gln Leu His Pro
 1               5                  10                  15 gta gca gct tta ttc acc gtg aca gcc cct aaa gaa gtg tac acc gta       96
Val Ala Ala Leu Phe Thr Val Thr Ala Pro Lys Glu Val Tyr Thr Val
                20                  25                  30
```

| | | |
|---|---|---|
| gac gtc ggc agc agt gtg agc ctg gag tgc gat ttt gac cgc aga gaa<br>Asp Val Gly Ser Ser Val Ser Leu Glu Cys Asp Phe Asp Arg Arg Glu<br>              35                      40                  45 | | 144 |
| tgc act gaa ctg gaa ggg ata aga gcc agt ttg cag aag gta gaa aat<br>Cys Thr Glu Leu Glu Gly Ile Arg Ala Ser Leu Gln Lys Val Glu Asn<br> 50                      55                      60 | | 192 |
| gat acg tct ctg caa agt gaa aga gcc acc ctg ctg gag gag cag ctg<br>Asp Thr Ser Leu Gln Ser Glu Arg Ala Thr Leu Leu Glu Glu Gln Leu<br>65                      70                      75                      80 | | 240 |
| ccc ctg gga aag gct ttg ttc cac atc cct agt gtc caa gtg aga gat<br>Pro Leu Gly Lys Ala Leu Phe His Ile Pro Ser Val Gln Val Arg Asp<br>              85                      90                      95 | | 288 |
| tcc ggg cag tac cgt tgc ctg gtc atc tgc ggg gcc gcc tgg gac tac<br>Ser Gly Gln Tyr Arg Cys Leu Val Ile Cys Gly Ala Ala Trp Asp Tyr<br>                    100                      105                    110 | | 336 |
| aag tac ctg acg gtg aaa gtc aaa gct tct tac atg agg ata gac act<br>Lys Tyr Leu Thr Val Lys Val Lys Ala Ser Tyr Met Arg Ile Asp Thr<br>          115                      120                      125 | | 384 |
| agg atc ctg gag gtt cca ggt aca ggg gag gtg cag ctt acc tgc cag<br>Arg Ile Leu Glu Val Pro Gly Thr Gly Glu Val Gln Leu Thr Cys Gln<br>130                      135                      140 | | 432 |
| gct aga ggt tat ccc cta gca gaa gtg tcc tgg caa aat gtc agt gtt<br>Ala Arg Gly Tyr Pro Leu Ala Glu Val Ser Trp Gln Asn Val Ser Val<br>145                      150                      155                    160 | | 480 |
| cct gcc aac acc agc cac atc agg acc ccc gaa ggc ctc tac cag gtc<br>Pro Ala Asn Thr Ser His Ile Arg Thr Pro Glu Gly Leu Tyr Gln Val<br>                    165                      170                    175 | | 528 |
| acc agt gtt ctg cgc ctc aag cct cag cct agc aga aac ttc agc tgc<br>Thr Ser Val Leu Arg Leu Lys Pro Gln Pro Ser Arg Asn Phe Ser Cys<br>                  180                      185                    190 | | 576 |
| atg ttc tgg aat gct cac atg aag gag ctg act tca gcc atc att gac<br>Met Phe Trp Asn Ala His Met Lys Glu Leu Thr Ser Ala Ile Ile Asp<br>          195                      200                      205 | | 624 |
| cct ctg agt cgg atg gaa ccc aaa gtc ccc aga acg tgg cca ctt cat<br>Pro Leu Ser Arg Met Glu Pro Lys Val Pro Arg Thr Trp Pro Leu His<br>210                      215                      220 | | 672 |
| gtt ttc atc ccg gcc tgc acc atc gct ttg atc ttc ctg gcc ata gtg<br>Val Phe Ile Pro Ala Cys Thr Ile Ala Leu Ile Phe Leu Ala Ile Val<br>225                      230                      235                    240 | | 720 |
| ata atc cag aga aag agg atc<br>Ile Ile Gln Arg Lys Arg Ile<br>              245 | | 741 |

<210> SEQ ID NO 7
<211> LENGTH: 31
<212> TYPE: DNA
<213> ORGANISM: Mus musculus

<400> SEQUENCE: 7
gtcgaccacc atgctgctcc tgctgccgat a                                      31

<210> SEQ ID NO 8
<211> LENGTH: 36
<212> TYPE: DNA
<213> ORGANISM: Mus musculus

<400> SEQUENCE: 8
gtcgactcac tagatcctct ttctctggat tatcac                                36

<210> SEQ ID NO 9
<211> LENGTH: 23

```
<212> TYPE: DNA
<213> ORGANISM: Homo sapiens

<400> SEQUENCE: 9
gtacataata gagcatggca gca                                          23

<210> SEQ ID NO 10
<211> LENGTH: 22
<212> TYPE: DNA
<213> ORGANISM: Homo sapiens

<400> SEQUENCE: 10
ccaccttttg caaactggct gt                                           22

<210> SEQ ID NO 11
<211> LENGTH: 290
<212> TYPE: PRT
<213> ORGANISM: Mus musculus

<400> SEQUENCE: 11
```

Met Arg Ile Phe Ala Gly Ile Ile Phe Thr Ala Cys Cys His Leu Leu
 1               5                  10                  15

Arg Ala Phe Thr Ile Thr Ala Pro Lys Asp Leu Tyr Val Val Glu Tyr
             20                  25                  30

Gly Ser Asn Val Thr Met Glu Cys Arg Phe Pro Val Glu Arg Glu Leu
         35                  40                  45

Asp Leu Leu Ala Leu Val Val Tyr Trp Glu Lys Glu Asp Glu Gln Val
     50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                 85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

```
Glu Thr
    290

<210> SEQ ID NO 12
<211> LENGTH: 290
<212> TYPE: PRT
<213> ORGANISM: Homo sapiens

<400> SEQUENCE: 12

Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
             35                  40                  45

Asp Leu Ala Ala Leu Ile Val Tyr Trp Glu Met Glu Asp Lys Asn Ile
         50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

METHODS OF IDENTIFYING COMPOUNDS THAT UPMODULATE T CELL ACTIVATION IN THE PRESENCE OF A PD-1 MEDIATED SIGNAL

RELATED APPLICATIONS

This application claims priority to U.S. Provisional Application Ser. No. 60/214,563, filed Jun. 28, 2000; U.S. Provisional Application Ser. No. 60/270,822, filed Feb. 23, 2001; and U.S. Provisional Application Ser. No. 60/271,114, filed Feb. 23, 2001. The entire contents of each of these applications are incorporated herein by this reference.

GOVERNMENT FUNDING

Work described herein was supported under AI 39671, CA84500, AI41584, AI38310, and AI40614, awarded by the National Institutes of Health. The U.S. government therefore may have certain rights in this invention.

BACKGROUND OF THE INVENTION

In order for T cells to respond to foreign polypeptides, two signals must be provided by antigen-presenting cells (APCs) to resting T lymphocytes (Jenkins, M. and Schwartz, R. (1987) *J. Exp. Med.* 165:302-319; Mueller, D. L. et al. (1990) *J. Immunol.* 144:3701-3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. (1996) *Annu. Rev. Immunol.* 14:233). Costimulation is neither antigen-specific, nor MHC-restricted, and is thought to be provided by one or more distinct cell surface molecules expressed by APCs (Jenkins, M. K. et al. (1988) *J. Immunol.* 140:3324-3330; Linsley, P.S. et al. (1991) *J. Exp. Med.* 173:721-730; Gimmi, C.D. et al. (1991) *Proc. Natl. Acad Sci. USA* 88:6575-6579; Young, J. W. et al. (1992) *J. Clin. Invest.* 90:229-237; Koulova, L. et al. (1991) *J. Exp. Med* 173:759-762; Reiser, H. et al. (1992) *Proc. Natl. Acad Sci. USA* 89:271-275; van-Seventer, G. A. et al. (1990) *J. Immunol.* 144:4579-4586; LaSalle, J. M. et al. (1991) *J. Immunol.* 147:774-80; Dustin, M. I. et al. (1989) *J. Exp. Med.* 169:503; Armitage, R. J. et al. (1992) *Nature* 357:80-82; Liu, Y. et al. (1992) *J. Exp. Med.* 175:437-445).

The CD80 (B7-1) and CD86 (B7-2) proteins, expressed on APCs, are critical costimulatory molecules (Freeman et al. (1991) *J. Exp. Med.* 174:625; Freeman et al. (1989) *J. Immunol.* 143:2714; Azuma et al. (1993) *Nature* 366:76; Freeman et al. (1993) *Science* 262:909). B7-2 appears to play a predominant role during primary immune responses, while B7-1, which is upregulated later in the course of an immune response, may be important in prolonging primary T cell responses or costimulating secondary T cell responses (Bluestone (1995) *Immunity* 2:555).

One ligand to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S. et al. (1991) *J. Exp. Med.* 173:721-730; Gimmi, C. D. et al. (1991) *Proc. Natl. Acad. Sci. USA* 88:6575-6579; June, C. H. et al. (1990) *Immunol. Today* 11:211-6; Harding, F.A. et al. (1992) *Nature* 356:607-609). A second ligand, termed CTLA4 (CD152) is homologous to CD28 but is not expressed on resting T cells and appears following T cell activation (Brunet, J. F. et al. (1987) *Nature* 328:267-270). CTLA4 appears to be critical in negative regulation of T cell responses (Waterhouse et al. (1995) *Science* 270:985). Blockade of CTLA4 has been found to remove inhibitory signals, while aggregation of CTLA4 has been found to provide inhibitory signals that downregulate T cell responses (Allison and Krummel (1995) *Science* 270:932). The B7 molecules have a higher affinity for CTLA4 than for CD28 (Linsley, P. S. et al. (1991) *J. Exp. Med.* 174:561-569) and B7-1 and B7-2 have been found to bind to distinct regions of the CTLA4 molecule and have different kinetics of binding to CTLA4 (Linsley et al. (1994) *Immunity* 1:793). A new molecule related to CD28 and CTLA4, ICOS, has been identified (Hutloff et al. (1999) *Nature* 397:263; WO 98/38216), as has its ligand, which is a new B7 family member (Aicher A. et al. (2000) *J. Immunol.* 164:4689-96; Mages H. W. et al. (2000) *Eur. J Immunol.* 30:1040-7; Brodie D. et al. (2000) *Curr. Biol.* 10:333-6; Ling V. et al. (2000) *J. Immunol.* 164:1653-7; Yoshinaga S. K. et al. (1999) *Nature* 402:827-32). If T cells are only stimulated through the T cell receptor, without receiving an additional costimulatory signal, they become nonresponsive, anergic, or die, resulting in downmodulation of the immune response.

Immune cells have receptors that transmit activating signals. For example, T cells have T cell receptors and the CD3 complex, B cells have B cell receptors, and myeloid cells have Fc receptors. In addition, immune cells bear receptors that transmit signals that provide costimulatory signals or receptors that transmit signals that inhibit receptor-mediated signaling. For example, CD28 transmits a costimulatory signal to T cells. After ligation of the T cell receptor, ligation of CD28 results in a costimulatory signal characterized by, e.g., upregulation of IL-2rα, IL-2rβ, and IL-2rγ receptor, increased transcription of IL-2 messenger RNA, and increased expression of cytokine genes (including IL-2, IFN-γ, GM-CSF, and TNF-α). Transmission of a costimulatory signal allows the cell to progress through the cell cycle and, thus, increases T cell proliferation (Greenfield et al. (1998) *Crit. Rev. Immunol.* 18:389). Binding of a receptor on a T cell which transmits a costimulatory signal to the cell (e.g., ligation of a costimulatory receptor that leads to cytokine secretion and/or proliferation of the T cell) by a costimulatory ligand results in costimulation. Thus, inhibition of an interaction between a costimulatory ligand and a receptor that transmits a costimulatory signal on immune cells results in a downmodulation of the immune response and/or specific unresponsiveness, termed immune cell anergy. Inhibition of this interaction can be accomplished using, e.g., anti-CD28 Fab fragments, antibodies to B7 family molecules, or by using a soluble form of a receptor to which a B7 family member molecule can bind as a competitive inhibitor (e.g., CTLA4Ig).

Inhibitory receptors that bind to costimulatory molecules have also been identified on immune cells. Activation of CTLA4, for example, transmits a negative signal to a T cell. Engagement of CTLA4 inhibits IL-2 production and can induce cell cycle arrest (Krummel and Allison (1996) *J. Exp. Med.* 183:2533). In addition, mice that lack CTLA4 develop lymphoproliferative disease (Tivol et al. (1995) *Immunity* 3:541; Waterhouse et al. (1995) *Science* 270:985). The blockade of CTLA4 with antibodies may remove an inhibitory signal, whereas aggregation of CTLA4 with antibody transmits an inhibitory signal. Therefore, depending upon the receptor to which a costimulatory molecule binds (i.e., a costimulatory receptor such as CD28 or an inhibitory receptor such as CTLA4), B7 molecules including B7-4 can promote T cell costimulation or inhibition.

PD-1 is a member of the immunoglobulin family of molecules (Ishida et al. (1992) *EMBO J.* 11:3887; Shinohara et al. (1994) *Genomics* 23:704). PD-1 was previously identified using a subtraction cloning based approach designed to identify modulators of programmed cell death (Ishida et al. (1992) *EMBO J.* 11:3887-95; Woronicz et al. (1995) *Curr. Top. Microbiol. Immunol.* 200:137). PD-1 is believed to play a role in regulating lymphocyte survival, e.g., during clonal selection (Honjo (1992) *Science* 258:591; Agata et al. (1996) *Int. Immunology* 8:765; Nishimura et al. (1996) *Int. Immunology* 8:773). PD-1 has an extracellular region containing an immunoglobulin superfamily domain, a transmembrane domain, and an intracellular region which includes an immunoreceptor tyrosine kinase-based inhibitory motif (ITIM) (Ishida et al. (1992) supra; Shinohara et al. (1994) supra; U.S. Pat. No. 5,698,520). This features also define a larger family of molecules, called the immunoinhibitory receptors, which also includes gp49B, PIR-B, and the killer inhibitory receptors (KIRs) (Vivier and Daeron (1997) *Immunology Today* 18:286). It is often assumed that the tyrosyl phosphorylated ITIM motif of these receptors interacts with the SH2-domain-containing phosphatases, which leads to inhibitory signals. A subset of these immunoinhibitory receptors binds to MHC molecules, for example the KIRs, and CTLA4 binds to B7-1 and B7-2. It has been proposed that there is a phylogenetic relationship between the MHC and B7 genes (Henry et al. (1999) *Immunology Today* 20:285-288).

PD-1 was also implicated as a regulator of B cell responses (Nishimura (1998) *Int. Immunology* 10:1563). Unlike CTLA4, which is found only on T cells, PD-1 is also found on B cells (in response anti-IgM) and on a subset of thymocytes and myeloid cells (Agata et al. (1996) supra; Nishimura et al. (1996) *Int. Immunology* 8:773).

The importance of the B7:CD28/CTLA4 costimulatory pathway has been demonstrated in vitro and in several in vivo model systems. Blockade of this costimulatory pathway results in the development of antigen-specific tolerance in murine and human systems (Harding, F. A. et al. (1992) *Nature* 356:607-609; Lenschow, D. J. et al. (1992) *Science* 257:789-792; Turka, L. A. et al. (1992) *Proc. Natl. Acad. Sci. USA* 89:11102-11105; Gimmi, C. D. et al. (1993) *Proc. Natl. Acad. Sci. USA* 90:6586-6590; Boussiotis, V. et al. (1993) *J. Exp. Med* 178:1753-1763). Conversely, expression of B7 by B7-negative murine tumor cells induces T-cell mediated specific immunity accompanied by tumor rejection and long lasting protection to tumor challenge (Chen, L. et al. (1992) *Cell* 71:1093-1102; Townsend, S. E. and Allison, J. P. (1993) *Science* 259:368-370; Baskar, S. et al. (1993) *Proc. Natl. Acad. Sci* 90:5687-5690.). Therefore, manipulation of the costimulatory pathways offers great potential to stimulate or suppress immune responses in humans.

SUMMARY OF THE INVENTION

The present invention is based, at least in part, on the discovery of novel nucleic acid molecules and polypeptides encoded by such nucleic acid molecules, referred to herein as PD-L2 nucleic acid and polypeptide molecules, which are members of the B7 family and are ligands for PD-1. Interaction of PD-L2 with PD-1 transmits a negative signal to immune cells, downregulating immune responses. Preferred PD-L2 molecules are expressed on the surface of professional antigen presenting cells (e.g., B lymphocytes, monocytes, dendritic cells, and Langerhans cells) and other antigen presenting cells (e.g., keratinocytes, endothelial cells, astrocytes, fibroblasts, and oligodendrocytes), down-regulate lymphocyte activation, and/or are bound by antibodies which recognize PD-L2 molecules. The PD-L2 nucleic acid and polypeptide molecules of the present invention are useful, e.g., in modulating the immune response. Accordingly, in one aspect, this invention provides isolated nucleic acid molecules encoding PD-L2 polypeptides, as well as nucleic acid fragments suitable as primers or hybridization probes for the detection of PD-L2-encoding nucleic acids.

In one embodiment, a PD-L2 nucleic acid molecule of the invention is at least about 70%, 75%, 80%, 85%, 90%, 91%, 92%, 93%, 94%, 95%, 96%, 97%, 98%, 99% or more identical to the nucleotide sequence (e.g., to the entire length of the nucleotide sequence) shown in SEQ ID NO:1 or 3, or a complement thereof.

In a preferred embodiment, the isolated nucleic acid molecule includes the nucleotide sequence shown in SEQ ID NO:1 or 3, or a complement thereof. In another embodiment, the nucleic acid molecule includes the nucleic acid sequence shown in SEQ ID NO:3 and nucleotides 1-273 of SEQ ID NO:1. In a further embodiment, the nucleic acid molecule includes the nucleic acid sequence shown in SEQ ID NO:3 and nucleotides 1096-1223 of SEQ ID NO:1. In another preferred embodiment, the nucleic acid molecule consists of the nucleotide sequence shown in SEQ ID NO:1 or 3.

In another embodiment, a PD-L2 nucleic acid molecule includes a nucleotide sequence encoding a polypeptide having an amino acid sequence sufficiently identical to the amino acid sequence of SEQ ID NO:2. In a preferred embodiment, a PD-L2 nucleic acid molecule includes a nucleotide sequence encoding a polypeptide having an amino acid sequence at least about 71%, 75%, 80%, 85%, 90%, 95%, 96%, 97%, 98%, 99% or more identical to the entire length of the amino acid sequence of SEQ ID NO:2.

In another preferred embodiment, an isolated nucleic acid molecule encodes the amino acid sequence of human PD-L2. In yet another preferred embodiment, the nucleic acid molecule includes a nucleotide sequence encoding a polypeptide having the amino acid sequence of SEQ ID NO:2. In yet another preferred embodiment, the nucleic acid molecule is at least about 50, 100, 150, 200, 250, 300, 350, 400, 450, 500, 550, 600, 650, 700, 750, 800, 850, 900, 950, 1000, 1050, 1100, 1150 or more nucleotides in length. In a further preferred embodiment, the nucleic acid molecule is at least about 50, 100, 150, 200, 250, 300, 350, 400, 450, 500, 550, 600, 650, 700, 750, 800, 850, 900, 950, 1000, 1050, 1100, 1150 or more nucleotides in length and encodes a polypeptide having a PD-L2 activity (as described herein).

Another embodiment of the invention features nucleic acid molecules, preferably PD-L2 nucleic acid molecules, which specifically detect PD-L2 nucleic acid molecules relative to nucleic acid molecules encoding non-PD-L2 polypeptides. For example, in one embodiment, such a nucleic acid molecule is at least about 880, 900, 950, 1000, 1050, 1100, 1150 or more nucleotides in length and hybridizes under stringent conditions to a nucleic acid molecule comprising the nucleotide sequence shown in SEQ ID NO:1, or a complement thereof. In another embodiment, such a nucleic acid molecule is at least 20, 30, 40, 50, 100, 150, 200, 250, 300 or more nucleotides in length and hybridizes under stringent conditions to a nucleic acid molecule comprising nucleotides 1-358 of SEQ ID NO:1, or a complement thereof. In a further embodiment, such a nucleic acid molecule is at least 20, 30, 40, 50, 100, 150, 200, 250, 300, 350, 400, 450, 500, 550, 600, 650, 700, 750, 800, 850, 900, 950, 1000, 1050, 1100, 1150 or more nucleotides in length, includes at least 15 (i.e., 15 contiguous) nucleotides of the sequence comprising nucleotides 1-358 of SEQ ID NO:1, or a complement thereof, and hybridizes under stringent conditions to a nucleic acid molecule comprising the nucleotide sequence shown in SEQ ID NO:1, or a complement thereof.

In preferred embodiments, the nucleic acid molecules are at least about 880 nucleotides in length and hybridize under stringent conditions to the nucleotide molecule set forth in SEQ ID NO:1 (i.e., to 880 contiguous nucleotides of SEQ ID NO:1), or a complement thereof. In other preferred embodiments, the nucleic acid molecules are at least about 15 nucleotides in length and hybridize under stringent conditions to nucleotides 1-358 of the nucleotide molecule set forth in SEQ ID NO:1 (i.e., to 15 contiguous nucleotides of nucleotides 1-358 of SEQ ID NO:1), or a complement thereof. In further preferred embodiments, the nucleic acid molecules are at least 15 nucleotides in length, include at least 15 (i.e., 15 contiguous) nucleotides of the sequence comprising nucleotides 1-358 of SEQ ID NO:1, or a complement thereof, and hybridize under stringent conditions to a nucleic acid molecule comprising the nucleotide sequence shown in SEQ ID NO:1, or a complement thereof.

In still other preferred embodiments, the nucleic acid molecule encodes a naturally occurring allelic variant of a polypeptide comprising the amino acid sequence of SEQ ID NO:2, wherein the nucleic acid molecule hybridizes to a complement of a nucleic acid molecule comprising SEQ ID NO:1 or 3, or a complement thereof, under stringent conditions.

Another embodiment of the invention provides an isolated nucleic acid molecule which is antisense to a PD-L2 nucleic acid molecule, e.g., is antisense to the coding strand of a PD-L2 nucleic acid molecule as shown in SEQ ID NO:1 or 3.

Another aspect of the invention provides a vector comprising a PD-L2 nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a polypeptide, preferably a PD-L2 polypeptide, by culturing in a suitable medium, a host cell, e.g., a mammalian host cell such as a non-human mammalian cell, of the invention containing a recombinant expression vector, such that the polypeptide is produced.

Another aspect of this invention features isolated or recombinant PD-L2 polypeptides (e.g., proteins, polypeptides, peptides, or fragments or portions thereof). In one embodiment, an isolated PD-L2 polypeptide includes at least one or more of the following domains: a signal peptide domain, an IgV domain, an IgC domain, an extracellular domain, a transmembrane domain, and a cytoplasmic domain.

In a preferred embodiment, a PD-L2 polypeptide includes at least one or more of the following domains: a signal peptide domain, an IgV domain, an IgC domain, an extracellular domain, a transmembrane domain, and a cytoplasmic domain, and has an amino acid sequence at least about 71%, 75%, 80%, 85%, 90%, 91%, 92%, 93%, 94%, 95%, 96%, 97%, 98%, 99% or more identical to the amino acid sequence of SEQ ID NO:2. In another preferred embodiment, a PD-L2 polypeptide includes at least one or more of the following domains: a signal peptide domain, an IgV domain, an IgC domain, an extracellular domain, a transmembrane domain, and a cytoplasmic domain, and has a PD-L2 activity (as described herein).

In yet another preferred embodiment, a PD-L2 polypeptide includes at least one or more of the following domains: a signal peptide domain, an IgV domain, an IgC domain, an extracellular domain, a transmembrane domain, and a cytoplasmic domain, and is encoded by a nucleic acid molecule having a nucleotide sequence which hybridizes under stringent hybridization conditions to a complement of a nucleic acid molecule comprising the nucleotide sequence of SEQ ID NO:1 or 3.

In another embodiment, the invention features fragments or portions of the polypeptide having the amino acid sequence of SEQ ID NO:2, wherein the fragment comprises at least 15 amino acids (i.e., contiguous amino acids) of the amino acid sequence of SEQ ID NO:2. In another embodiment, a PD-L2 polypeptide comprises or consists of the amino acid sequence of SEQ ID NO:2.

In another embodiment, the invention features a PD-L2 polypeptide which is encoded by a nucleic acid molecule consisting of a nucleotide sequence at least about 70%, 75%, 80%, 85%, 90%, 91%, 92%, 93%, 94%, 95%, 96%, 97%, 98%, 99% or more identical to a nucleotide sequence of SEQ ID NO:1 or 3, or a complement thereof. This invention further features a PD-L2 polypeptide which is encoded by a nucleic acid molecule consisting of a nucleotide sequence which hybridizes under stringent hybridization conditions to a complement of a nucleic acid molecule comprising the nucleotide sequence of SEQ ID NO:1 or 3.

The polypeptides of the present invention or portions thereof, e.g., biologically active portions thereof, can be operatively linked to a non-PD-L2 polypeptide (e.g., heterologous amino acid sequences) to form fusion polypeptides. The invention further features antibodies, such as monoclonal or polyclonal antibodies, that specifically bind polypeptides of the invention, preferably PD-L2 polypeptides. In addition, the PD-L2 polypeptides (or biologically active portions thereof) or modulators of the PD-L2 molecules can be incorporated into pharmaceutical compositions, which optionally include pharmaceutically acceptable carriers.

In another aspect, the present invention provides a method for detecting the presence of a PD-L2 nucleic acid molecule, protein, or polypeptide in a biological sample by contacting the biological sample with an agent capable of detecting a PD-L2 nucleic acid molecule, protein, or polypeptide, such that the presence of a PD-L2 nucleic acid molecule, protein or polypeptide is detected in the biological sample.

In another aspect, the present invention provides a method for detecting the presence of PD-L2 activity in a biological sample by contacting the biological sample with an agent capable of detecting an indicator of PD-L2 activity, such that the presence of PD-L2 activity is detected in the biological sample.

In another aspect, the invention provides a method for modulating PD-L2 activity, comprising contacting a cell capable of expressing PD-L2 with an agent that modulates PD-L2 activity, such that PD-L2 activity in the cell is modulated. In one embodiment, the agent inhibits PD-L2 activity. In another embodiment, the agent stimulates PD-L2 activity. In a further embodiment, the agent interferes with or enhances the interaction between a PD-L2 polypeptide and its natural binding partner(s), e.g., PD-1. In a preferred embodiment, the binding partner is PD-1. In one embodiment, the agent is an antibody that specifically binds to a PD-L2 polypeptide. In a further embodiment, the agent is a combination of an antibody that specifically binds to a PD-L2 polypeptide and an antibody that specifically binds to a PD-L1 polypeptide. In another embodiment, the agent is a peptide, peptidomimetic, or other small molecule that binds to a PD-L2 polypeptide. In yet another embodiment, the agent is another PD-1 ligand which can modulate the interaction between PD-L2 and PD-1. In still another embodiment, the agent modulates expression of PD-L2 by modulating transcription of a PD-L2 gene, translation of a PD-L2 mRNA, or post-translational modification of a PD-L2 polypeptide. In another embodiment, the agent is a nucleic acid molecule having a nucleotide sequence that is antisense to the coding strand of a PD-L2 mRNA or a PD-L2 gene.

In one embodiment, the methods of the present invention are used to treat a subject having a disorder or condition characterized by aberrant, insufficient, or unwanted PD-L2 polypeptide or nucleic acid expression or activity by administering an agent which is a PD-L2 modulator to the subject. In one embodiment, the PD-L2 modulator is a PD-L2 polypeptide. In another embodiment the PD-L2 modulator is a PD-L2 nucleic acid molecule. In a further embodiment, the PD-L2 modulator is an antibody that specifically binds to a PD-L2 polypeptide. In another embodiment, the PD-L2 modulator is a combination of an antibody that specifically binds to a PD-L2 polypeptide and an antibody that specifically binds to a PD-L1 polypeptide. In yet another embodiment, the PD-L2 modulator is a peptide, peptidomimetic, or other small molecule. In a preferred embodiment, the disorder or condition characterized by aberrant, insufficient, or unwanted PD-L2 polypeptide or nucleic acid expression or activity is an immune response disorder or condition that would benefit from modulation of PD-L2 activity. In another embodiment, the invention further provides treating the subject with an additional agent that modulates an immune response.

In still another embodiment, the invention provides a vaccine comprising an antigen and an agent that reduces or inhibits PD-L2 activity. In a preferred embodiment, the vaccine inhibits the interaction between PD-L2 and its natural binding partner(s). In a more preferred embodiment, the binding partner is PD-1.

The present invention also provides diagnostic assays for identifying the presence or absence of a genetic alteration characterized by at least one of (i) aberrant modification or mutation of a gene encoding a PD-L2 polypeptide; (ii) misregulation of the gene; and (iii) aberrant post-translational modification of a PD-L2 polypeptide, wherein a wild-type form of the gene encodes a polypeptide with a PD-L2 activity.

In another aspect the invention provides methods for identifying a compound that binds to or modulates the activity of a PD-L2 polypeptide, by providing an indicator composition comprising a PD-L2 polypeptide having PD-L2 activity, contacting the indicator composition with a test compound, and determining the effect of the test compound on PD-L2 activity in the indicator composition to identify a compound that modulates the activity of a PD-L2 polypeptide.

In another aspect, this invention provides a method for modulating an immune response by modulating the interaction between PD-1 and PD-L2.

In one aspect, the invention features a method for modulating the interaction of PD-L2 with its natural binding partner(s) on an immune cell comprising contacting an antigen presenting cell which expresses PD-L2 with an agent selected from the group consisting of: a form of PD-L2, a form of PD-1, or an agent that modulates the interaction of PD-L2 and its natural binding partner(s) such that the interaction of PD-L2 with it natural binding partner(s) on an immune cell is modulated. In a preferred embodiment, an agent that modulates the interaction of PD-L2 and its natural binding partner(s) (e.g., PD-1) is an antibody that specifically binds to PD-L2. In another preferred embodiment, the agent is a combination of an antibody that specifically binds to PD-L2 and an antibody that specifically binds to PD-1.

In one embodiment, the interaction of PD-L2 with its natural binding partner(s) is upregulated. In another embodiment, the interaction of PD-L2 with its natural binding partner(s) is downregulated.

In one embodiment, the method further comprises contacting the immune cell or the antigen presenting cell with an additional agent that modulates an immune response.

In one embodiment, the step of contacting is performed in vitro. In another embodiment, the step of contacting is performed in vivo.

In one embodiment, the immune cell is selected from the group consisting of: a T cell, a B cell, and a myeloid cell.

In one embodiment, the PD-L2 binding partner is PD-1.

In another aspect, the invention pertains to a method for inhibiting activation in an immune cell via a non-apoptotic mechanism comprising increasing the activity or expression of PD-L2 in a cell such that immune cell activation is inhibited.

In yet another aspect, the invention pertains to a vaccine comprising an antigen and an agent that inhibits the interaction between PD-L2 and its natural binding partner(s).

In still another aspect, the invention pertains to a vaccine comprising an antigen and an agent that promotes the interaction between PD-L2 and its natural binding partner(s).

In one embodiment, the PD-L2 binding partner is PD-1.

In another aspect, the invention pertains to a method for treating a subject having a condition that would benefit from upregulation of an immune response comprising administering an agent that inhibits the interaction between PD-L2 and its natural binding partner(s) on cells of the subject such that a condition that would benefit from upregulation of an immune response is treated.

In one embodiment, the agent comprises a blocking antibody or a small molecule that binds to PD-L2 and inhibits the interaction between PD-L2 and its natural binding partner(s). In another embodiment, the agent comprises a combination of an antibody that specifically binds to PD-L2 and an antibody that specifically binds to PD-L1.

In another embodiment, the method further comprises administering a second agent that upregulates an immune response to the subject.

In one embodiment, the condition is selected from the group consisting of: a tumor, a pathogenic infection, or an immunosuppressive disease.

In another embodiment, the PD-L2 binding partner is PD-1.

In one aspect, the invention pertains to a method for treating a subject having a condition that would benefit from downregulation of an immune response comprising administering an agent that stimulates the interaction between PD-L2 and its natural binding partner(s) on cells of the subject such that a condition that would benefit from downregulation of an immune response is treated.

In one embodiment agent comprises an antibody or a small molecule that stimulates the interaction between PD-L2 and its natural binding partner(s).

In another embodiment, the method further comprises administering a second agent that downregulates an immune response to the subject.

In another embodiment, the condition is selected from the group consisting of: a transplant, an allergy, and an autoimmune disorder.

In one embodiment, the PD-L2 binding partner is PD-1.

In another aspect, the invention pertains to a cell-based assay for screening for compounds which modulate the activity of PD-L2 comprising contacting a cell expressing a PD-L2 target molecule with a test compound and determining the ability of the test compound to modulate the activity of the PD-L2 target molecule In still another aspect, the invention pertains to a cell-free assay for screening for compounds which modulate the binding of PD-L2 to a target molecule comprising contacting a PD-L2 polypeptide or biologically active portion thereof with a test compound and determining the ability of the test compound to bind to the PD-L2 polypeptide or biologically active portion thereof.

In another embodiment, the invention pertains to a method of identifying a compound which modulates T cell activation at a first and second antigen concentration comprising contacting a T cell expressing a PD-L2 target molecule with a test compound at a first antigen concentration, determining the ability of the test compound to modulate T cell proliferation or cytokine production at the first antigen concentration, contacting a T cell expressing a PD-L2 target molecule with the test compound at a second antigen concentration, and determining the ability of the test compound to modulate T cell proliferation or cytokine production at the second antigen concentration, thereby identifying a compound which modulates T cell activation at a first and second antigen concentration.

In one embodiment, the PD-L2 target molecule is PD-1.

Other features and advantages of the invention will be apparent from the following detailed description and claims.

BRIEF DESCRIPTION OF THE DRAWINGS

FIG. 1 depicts the cDNA sequence and predicted amino acid sequence of human PD-L2. The nucleotide sequence corresponds to nucleic acids 1-1223 of SEQ ID NO:1. The amino acid sequence corresponds to amino acids 1-273 of SEQ ID NO:2. The coding region without the 5' or 3' untranslated regions of the human PD-L2 gene is shown in SEQ ID NO:3.

FIG. 2 depicts the CDNA sequence and amino acid sequence of mouse PD-L2. The nucleotide sequence corresponds to nucleic acids 1-1655 of SEQ ID NO:4. The amino acid sequence corresponds to amino acids 1-247 of SEQ ID NO:5. The coding region without the 5' or 3' untranslated region of the mouse PD-L2 gene is shown in SEQ ID NO:6.

FIG. 3 depicts the amino acid sequences of the human and mouse PD-L2 polypeptides (SEQ ID NO:2 and SEQ ID NO:5, respectively) and illustrates the signal peptide, IgV, IgC, extracellular, transmembrane, and cytoplasmic domains.

FIG. 5 depicts an alignment of the amino acid sequences of the mouse and human PD-L2 polypeptides (SEQ ID NO:5 and SEQ ID NO:2, respectively). Identical amino acids are illustrated between the two sequences.

FIG. 6 depicts an alignment of the amino acid sequences of the mouse PD-L2 (SEQ ID NO:5), human PD-L2 (SEQ ID NO:2), mouse PD-L1 (SEQ ID NO:11), and human PD-L1 (SEQ ID NO:12).

FIG. 16 depicts the enhancement of T cell proliferation in the presence of anti-PD-L1, anti PD-L2 antibodies, or a combination of anti-PD-L1 and anti-PD-L2 antibodies. Allogeneic CD4+ T cells were stimulated in a mixed lymphocyte reaction by IL-10 treated dendritic cells.

DETAILED DESCRIPTION OF THE INVENTION

Figure 4:
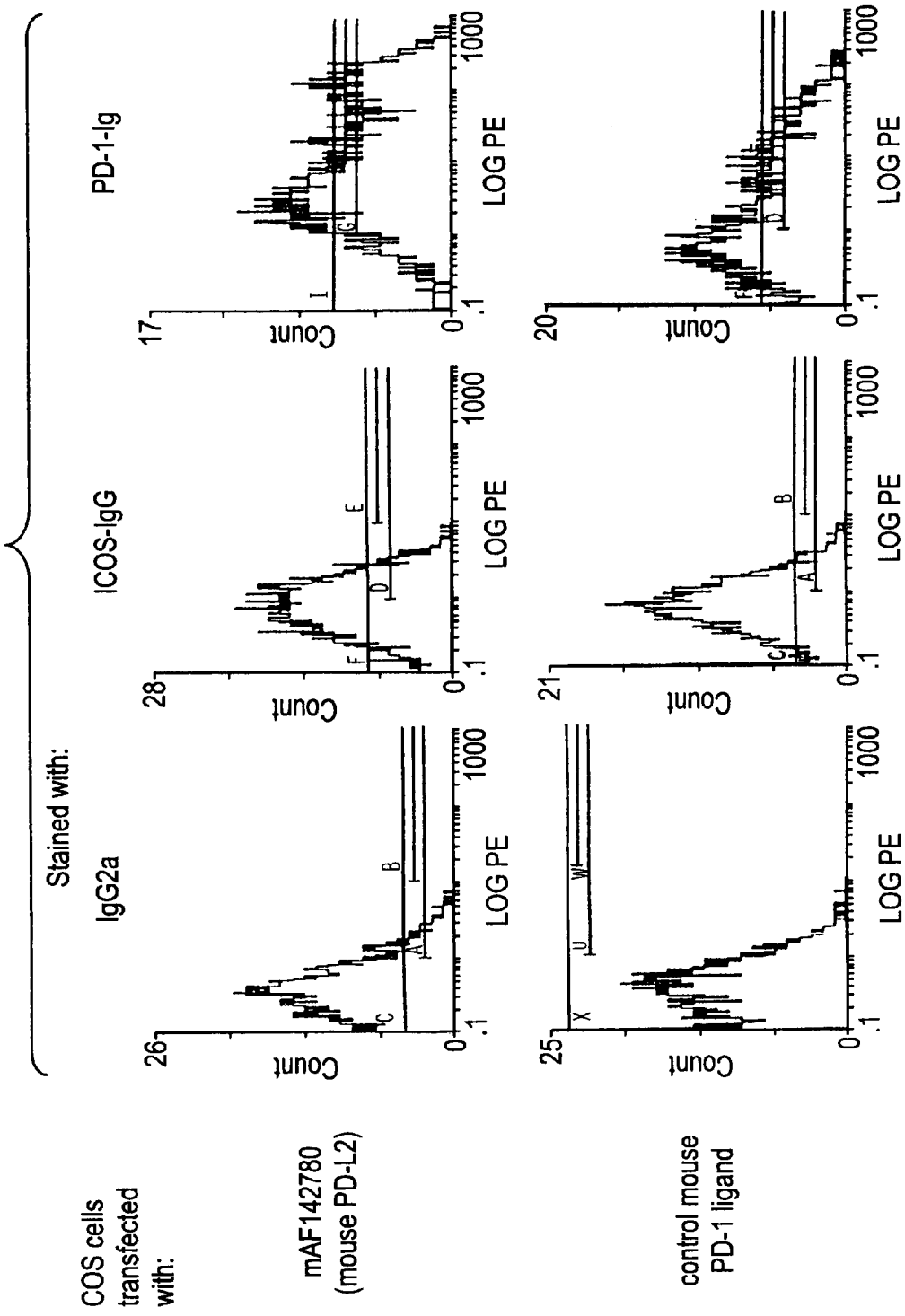
FIG. 4 illustrates the results of FACS analysis of the binding of IgG2a (control Ig), ICOS-IgG, and control PD-1-Ig to COS cells transfected with mouse PD-L2 or with a control mouse PD-1 ligand.

In addition to the previously characterized B lymphocyte activation antigens, e.g., B7-1 and B7-2, there are other antigens on the surface of antigen-presenting cells (e.g., B cells, monocytes, dendritic cell, Langerhans cells, keratinocytes, endothelial cells, astrocytes, fibroblasts, and oligodendrocytes) which modulate the activation of B cells, T cells, and other immune cells. The present invention is based, at least in part, on the discovery of novel molecules, referred to herein as PD-L2 polypeptides, which bind to the PD-1 receptor and down-regulate the activation of these immune cells and/or to downregulate immune responses. These novel molecules play a role in the modulating the immune response.

The instant discovery that PD-L2 binds to PD-1 places PD-L2 in a family of inhibitory ligands, and sequence analysis places PD-L2 in the B7 family. While engagement of a costimulatory receptor results in a costimulatory signal in an immune cell, engagement of an inhibitory receptor, e.g., CTLA4 or PD-1 (for example by crosslinking or by aggregation), leads to the transmission of an inhibitory signal in an immune cell resulting in downmodulation of immune cell responses and/or in immune cell anergy. While transmission of an inhibitory signal leads to downmodulation in immune cell responses (and a resulting downmodulation in the overall immune response), the prevention of an inhibitory signal (e.g., by using a non-activating antibody against PD-1) in immune cells leads to upmodulation of immune cell responses (and a resulting upmodulation of an immune response).

PD-L2 has homology to PD-L1, a previously described ligand for PD-1 (see the co-pending U.S. application Ser. No. 09/644,934; International Publication WO 01/14557; Dong, H. et al. (1999) *Nat. Med.* 5:1365-1369; and Freeman, G. J. et al. (2000) *J. Exp. Med.* 192:1027-1034 the contents of each of which are incorporated herein by reference).

The instant invention makes available agents useful for modulating the activity and/or expression of PD-L2; agents for modulating the interaction between PD-L2 and its natural binding partner(s) (e.g., PD-1), and agents for modulating the immune response via modulation of the interaction between PD-L2 and its natural binding partner(s) (e.g., PD-1). Exemplary modulatory agents for use in these methods are described further as follows.

Definitions

As used herein, the term "immune cell" includes cells that are of hematopoietic origin and that play a role in the immune response. Immune cells include lymphocytes, such as B cells and T cells; natural killer cells; and myeloid cells, such as monocytes, macrophages, eosinophils, mast cells, basophils, and granulocytes.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

As used herein, the term "immune response" includes T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "downmodulation" with reference to the immune response includes a diminution in any one or more immune responses, while the term "upmodulation" with reference to the immune response includes an increase in any one or more immune responses. It will be understood that upmodulation of one type of immune response may lead to a corresponding downmodulation in another type of immune response. For example, upmodulation of the production of certain cytokines (e.g., IL-10) can lead to downmodulation of cellular immune responses.

As used herein, the term "costimulatory receptor" includes receptors which transmit a costimulatory signal to an immune cell, e.g., CD28 or ICOS. As used herein, the term "inhibitory receptors" includes receptors which transmit a negative signal to an immune cell (e.g., CTLA4 or PD-1).

As used herein, the term "costimulate", with reference to activated immune cells, includes the ability of a costimulatory molecule to provide a second, non-activating, receptor-mediated signal (a "costimulatory signal") that induces proliferation or effector function. For example, a costimulatory signal can result in cytokine secretion, e.g., in a T cell that has received a T cell-receptor-mediated signal. Immune cells that have received a cell receptor-mediated signal, e.g., via an activating receptor, are referred to herein as "activated immune cells."

An inhibitory signal as transduced by an inhibitory receptor can occur even if a costimulatory receptor (such as CD28 or ICOS) in not present on the immune cell and, thus, is not simply a function of competition between inhibitory receptors and costimulatory receptors for binding of costimulatory molecules (Fallarino et al. (1998) *J. Exp. Med.* 188:205). Transmission of an inhibitory signal to an immune cell can result in unresponsiveness, anergy or programmed cell death in the immune cell. Preferably, transmission of an inhibitory signal operates through a mechanism that does not involve apoptosis. As used herein the term "apoptosis" includes programmed cell death which can be characterized using techniques which are known in the art. Apoptotic cell death can be characterized, e.g., by cell shrinkage, membrane blebbing, and chromatin condensation culminating in cell fragmentation. Cells undergoing apoptosis also display a characteristic pattern of internucleosomal DNA cleavage.

Depending upon the form of the PD-L2 molecule that binds to a receptor, a signal can be either transmitted (e.g., by a multivalent form of a PD-L2 molecule that results in crosslinking of the receptor or by a soluble form of PD-L2 that binds to Fc receptors on antigen presenting cells) or inhibited (e.g., by a soluble, monovalent form of a PD-L2 molecule or a soluble form of PD-L2 that is altered using methods known in the art such that it does not bind to Fc receptors on antigen presenting cells), e.g., by competing with activating forms of PD-L2 molecules for binding to the receptor. However, there are instances in which a soluble molecule can be stimulatory. The effects of the various modulatory agents can be easily demonstrated using routine screening assays as described herein.

As used herein, the term "activating receptor" includes immune cell receptors that bind antigen, complexed antigen (e.g., in the context of MHC molecules), or antibodies. Such activating receptors include T cell receptors (TCRs), B cell receptors (BCRs), cytokine receptors, LPS receptors, complement receptors, and Fc receptors.

For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g, protein phosphorylation, membrane lipid changes, ion fluxes, cyclic nucleotide alterations, RNA transcription changes, protein synthesis changes, and cell volume changes.

The term "B cell receptor" (BCR) as used herein includes the complex between membrane Ig (mIg) and other transmembrane polypeptides (e.g., Igα and Igβ) found on B cells. The signal transduction function of mIg is triggered by crosslinking of receptor molecules by oligomeric or multimeric antigens. B cells can also be activated by anti-immunoglobulin antibodies. Upon BCR activation, numerous changes occur in B cells, including tyrosine phosphorylation.

The term "Fc receptor" (FcRs) include cell surface receptors for the Fc portion of immunoglobulin molecules (Igs). Fc receptors are found on many cells which participate in immune responses. Among the human FcRs that have been identified so far are those which recognize IgG (designated Fcγ R), IgE (Fcϵ R1), IgA (Fcα R), and polymerized IgM/A (Fcμα R). FcRs are found in the following cell types: Fcϵ R I (mast cells), Fcϵ R.II (many leukocytes), Fcα R (neutrophils), and Fcμα R (glandular epithelium, hepatocytes) (Hogg, N. (1988) *Immunol. Today* 9:185-86). The widely studied FcγRs are central in cellular immune defenses, and are responsible for stimulating the release of mediators of inflammation and hydrolytic enzymes involved in the pathogenesis of autoimmune disease (Unkeless, J. C. (1988) *Annu. Rev. Immunol.* 6:251-87). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different receptors for IgG: h Fcγ RI (found on monocytes/ macrophages), hFcγ RII (on monocytes, neutrophils, eosinophils, platelets, possibly B cells, and the K562 cell line), and Fcγ III (on NK cells, neutrophils, eosinophils, and macrophages).

With respect to T cells, transmission of a costimulatory signal to a T cell involves a signaling pathway that is not inhibited by cyclosporin A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

As used herein, the term "inhibitory signal" refers to a signal transmitted via an inhibitory receptor (e.g., CTLA4 or PD-1) molecule on an immune cell. Such a signal antagonizes a signal via an activating receptor (e.g., via a TCR, CD3, BCR, or Fc molecule) and can result, e.g., in inhibition of: second messenger generation; proliferation; or effector function in the immune cell, e.g., reduced phagocytosis, antibody production, or cellular cytotoxicity, or the failure of the immune cell to produce mediators (such as cytokines (e.g., IL-2) and/or mediators of allergic responses); or the development of anergy.

As used herein, the term "unresponsiveness" includes refractivity of immune cells to stimulation, e.g., stimulation via an activating receptor or a cytokine. Unresponsiveness can occur, e.g., because of exposure to immunosuppressants or high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257: 1134).

Modulation of a costimulatory signal results in modulation of effector function of an immune cell. Thus, the term "PD-L2 activity" includes the ability of a PD-L2 polypeptide to bind its natural binding partner(s), e.g., PD-1, the ability to modulate immune cell costimulatory or inhibitory signals, and the ability to modulate the immune response.

With respect to PD-1, the term "activity" includes the ability of a PD-1 polypeptide to modulate an inhibitory signal in an activated immune cell, e.g., by engaging a natural ligand on an antigen presenting cell. PD-1 transmits an inhibitory signal to an immune cell in a manner similar to CTLA4. Modulation of an inhibitory signal in an immune cell results in modulation of proliferation of and/or cytokine secretion by an immune cell. PD-1 can also modulate a costimulatory signal by competing with a costimulatory receptor for binding of its natural ligand(s). Thus, the term "PD-1 activity" includes the ability of a PD-1 polypeptide to bind its natural ligand(s), the ability to modulate immune cell costimulatory or inhibitory signals, and the ability to modulate the immune response.

As used herein, a "naturally-occurring" nucleic acid molecule refers to an RNA or DNA molecule having a nucleotide sequence that occurs in nature (e.g., encodes a natural protein).

As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of other proteins, cellular material and culture medium when isolated from cells or produced by recombinant DNA techniques, or chemical precursors or other chemicals when chemically synthesized.

An "isolated" or "purified" protein or biologically active portion thereof is substantially free of cellular material or other contaminating proteins from the cell or tissue source from which the PD-L2 protein is derived, or substantially free from chemical precursors or other chemicals when chemically synthesized. The language "substantially free of cellular material" includes preparations of PD-L2 protein in which the protein is separated from cellular components of the cells from which it is isolated or recombinantly produced. In one embodiment, the language "substantially free of cellular material" includes preparations of PD-L2 protein having less than about 30% (by dry weight) of non-PD-L2 protein (also referred to herein as a "contaminating protein"), more preferably less than about 20% of non-PD-L2 protein, still more preferably less than about 10% of non-PD-L2 protein, and most preferably less than about 5% non-PD-L2 protein.

When the PD-L2 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PD-L2 protein in which the protein is separated from chemical precursors or other chemicals which are involved in the synthesis of the protein. In one embodiment, the language "substantially free of chemical precursors or other chemicals" includes preparations of PD-L2 protein having less than about 30% (by dry weight) of chemical precursors or non-PD-L2 chemicals, more preferably less than about 20% chemical precursors or non-PD-L2 chemicals, still more preferably less than about 10% chemical precursors or non-PD-L2 chemicals, and most preferably less than about 5% chemical precursors or non-PD-L2 chemicals.

The term "antibody", as used herein, includes an "antigen-binding portion" of an antibody (or simply "antibody portion"), as well as whole antibody molecules. The term "antigen-binding portion", as used herein, refers to one or more fragments of an antibody that retain the ability to specifically bind to an antigen (e.g, PD-L2). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998 *Nat. Biotechnol.* 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and Vl can also be used in the generation of Fab, Fv, or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al. (1993) *Proc. Natl. Acad. Sci. USA* 90:6444-6448; Poljak, R. J. et al. (1994) *Structure* 2:1121-1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M. et al. (1995) *Hum. Antibodies Hybridomas* 6:93-101) and use of a cysteine residue, a marker peptide and a C-terminal polyhistidine tag to make bivalent and biotinylated scFv molecules (Kipriyanov, S. M. et al. (1994) *Mol Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Antibodies may be polyclonal or monoclonal; xenogeneic, allogeneic, or syngeneic; or modified forms thereof, e.g., humanized, chimeric, etc. Preferably, antibodies of the invention bind specifically or substantially specifically to PD-L2 molecules. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds PD-L2 is substantially free of antibodies that specifically bind antigens other than PD-L2). Moreover, an isolated antibody may be substantially free of other cellular material and/or chemicals.

PD-L2 Nucleic Acid and Polypeptide Molecules

The term "family" when referring to the polypeptide and nucleic acid molecules of the invention is intended to mean two or more polypeptide or nucleic acid molecules having a common structural domain or motif and having sufficient amino acid or nucleotide sequence homology as defined herein. Such family members can be naturally or non-naturally occurring and can be from either the same or different species. For example, a family can contain a first polypeptide of human origin, as well as other, distinct polypeptides of human origin or alternatively, can contain homologues of non-human origin, e.g., monkey polypeptides. Members of a family may also have common functional characteristics.

For example, the family of PD-L2 polypeptides of the present invention preferably comprises least one "signal peptide domain". As used herein, a "signal sequence" or "signal peptide" includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., Valine, Leucine, Isoleucine or Phenylalanine). Such a "signal sequence", also referred to in the art as a "signal peptide", serves to direct a polypeptide containing such a sequence to a lipid bilayer, and is cleaved in secreted and membrane bound polypeptides. A signal sequence was identified in the amino acid sequence of native human PD-L2 at about amino acids 1-19 of SEQ ID NO:2 (FIG. 3). A signal sequence was also identified in the amino acid sequence of native mouse PD-L2 at about amino acids 1-19 of SEQ ID NO:5 (FIG. 3).

In another embodiment of the invention, a PD-L2 polypeptide of the present invention is identified based on the presence of a "transmembrane domain". As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) *Annu. Rev. Neurosci.* 19:235-263, the contents of which are incorporated herein by reference. Amino acid residues 220-243 of the native human PD-L2 polypeptide, and amino acid residues 201-243 of the predicted mature polypeptide, are predicted to comprise transmembrane domains (see FIG. 3). Amino acid residues 220-242 of the native mouse PD-L2 polypeptide, and amino acid residues 201-223 of the predicted mature polypeptide, are predicted to comprise transmembrane domains (see FIG. 3). Accordingly, PD-L2 polypeptides having at least 71-80%, or more preferably about 80-90% homology with a transmembrane domain of human PD-L2 are within the scope of the invention.

In another embodiment, a PD-L2 molecule of the present invention is identified based on the presence of an "IgC domain" or an "IgV domain" in the polypeptide or corresponding nucleic acid molecule. As used herein, IgV and IgC domains are recognized in the art as Ig superfamily member domains. These domains correspond to structural units that have distinct folding patterns called Ig folds. Ig folds are comprised of a sandwich of two β sheets, each consisting of antiparallel β strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of β strands. Amino acid residues 20-120 of the native human PD-L2 polypeptide, and amino acid residues 1-101 of the predicted mature polypeptide, are predicted to comprise IgV domains (see FIG. 3). Amino acid residues 20-120 of the native mouse PD-L2 polypeptide, and amino acid residues 1-101 of the predicted mature polypeptide, are also predicted to comprise IgV domains (see FIG. 3). Amino acid residues 121-219 of the native human PD-L2 polypeptide, and amino acid residues 102-200 of the predicted mature polypeptide, are predicted to comprise IgC domains (see FIG. 3). Amino acid residues 121-219 of the native mouse PD-L2 polypeptide, and amino acid residues 102-200 of the predicted mature polypeptide, are also predicted to comprise IgC domains (see FIG. 3). In a preferred embodiment, the presence of an IgV domain is required for binding of PD-L2 to its natural binding partner, e.g., PD-1.

In another embodiment, a PD-L2 molecule of the present invention is identified based on the presence of a "extracellular domain" in the polypeptide or corresponding nucleic acid molecule. As used herein, the term "extracellular domain" represents the N-terminal amino acids which extend as a tail from the surface of a cell. An extracellular domain of the present invention includes an IgV domain and an IgC domain, and may include a signal peptide domain. Amino acid residues 1-219 of the native human PD-L2 polypeptide, and amino acid residues 1-200 of the predicted mature polypeptide, are predicted to comprise extracellular domains (see FIG. 3). Amino acid residues 1-219 of the native mouse PD-L2 polypeptide, and amino acid residues 1-200 of the predicted mature polypeptide, are also predicted to comprise extracellular domains (see FIG. 3).

In still another embodiment, a PD-L2 molecule of the present invention is identified based on the presence of a "cytoplasmic domain" in the polypeptide or corresponding nucleic acid molecule. As used herein, the term "cytoplasmic domain" represents the C-terminal amino acids which extend as a tail into the cytoplasm of a cell. Amino acid residues 244-273 of the native human PD-L2 polypeptide, and amino acid residues 225-273 of the predicted mature polypeptide, are predicted to comprise cytoplasmic domains (see FIG. 3). Amino acid residues 243-247 of the native mouse PD-L2 polypeptide, and amino acid residues 224-228 of the predicted mature polypeptide, are also predicted to comprise cytoplasmic domains.

In a preferred embodiment, the PD-L2 molecules of the invention include at least one or more of the following domains: a signal peptide domain, an IgV domain, an IgC domain, an extracellular domain, a transmembrane domain, and a cytoplasmic domain.

Isolated polypeptides of the present invention, preferably PD-L2 polypeptides, have an amino acid sequence sufficiently identical to the amino acid sequence of SEQ ID NO:2, or are encoded by a nucleotide sequence sufficiently identical to SEQ ID NO:1 or 3. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90-95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% homology and share a common functional activity are defined herein as sufficiently identical.

As used interchangeably herein, "PD-L2 activity", "biological activity of PD-L2" or "functional activity of PD-L2", refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor PD-1. Alternatively, a PD-L2 activity is an indirect activity, such as a cellular signaling activity mediated by interaction of the PD-L2 polypeptide with its natural binding partner, e.g., PD-1. The biological activities of PD-L2 are described herein. For example, the PD-L2 polypeptides of the present invention can have one or more of the following activities: 1) bind to and/or modulate the activity of the receptor PD-1 or other PD-L2 natural binding partners, 2) modulate intra- or intercellular signaling, 3) modulate activation of immune cells, e.g., T lymphocytes, and 4) modulate the immune response of an organism, e.g., a mouse or human organism.

Accordingly, another embodiment of the invention features isolated PD-L2 proteins and polypeptides having a PD-L2 activity. Other preferred polypeptides are PD-L2 polypeptides having one or more of the following domains: a signal peptide domain, an IgV domain, an IgC domain, an extracellular domain, a transmembrane domain, and a cytoplasmic domain, and, preferably, a PD-L2 activity.

Additional preferred PD-L2 polypeptides have at least one extracellular domain, and one or more of a signal peptide domain, an IgV domain, an IgC domain, an transmembrane domain, and a cytoplasmic domain, and are, preferably, encoded by a nucleic acid molecule having a nucleotide sequence which hybridizes under stringent hybridization conditions to a nucleic acid molecule comprising a complement of the nucleotide sequence of SEQ ID NO:1, 3, 4, or 6.

The nucleotide sequence of the isolated human PD-L2 cDNA and the predicted amino acid sequence of the human PD-L2 polypeptide are shown in FIG. 1 and in SEQ ID NO:1 and 2, respectively. The nucleotide sequence of the isolated mouse PD-L2 cDNA and the amino acid sequence of the mouse PD-L2 polypeptide are shown in FIG. 2 and in SEQ ID NO:4 and 5, respectively.

The human PD-L2 gene, which is approximately 1223 nucleotides in length, encodes a polypeptide having a molecular weight of approximately 30.0 kD and which is approximately 273 amino acid residues in length. The mouse PD-L2 gene, which is approximately 1655 nucleotides in length, encodes a polypeptide having a molecular weight of approximately 27.2 kD and which is approximately 247 amino acid residues in length.

Various aspects of the invention are described in further detail in the following subsections:

I. Isolated Nucleic Acid Molecules

One aspect of the invention pertains to isolated nucleic acid molecules that encode PD-L2 polypeptides or biologically active portions thereof, as well as nucleic acid fragments sufficient for use as hybridization probes to identify PD-L2-encoding nucleic acid molecules (e.g., PD-L2 mRNA) and fragments for use as PCR primers for the amplification or mutation of PD-L2 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid (i.e., sequences located at the 5' and 3' ends of the nucleic acid molecule) in the genomic DNA of the organism from which the nucleic acid is derived. For example, in various embodiments, the isolated PD-L2 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid molecule is derived. Moreover, an "isolated" nucleic acid molecule, such as a cDNA molecule, can be substantially free of other cellular material, or culture medium, when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1,3,4, or 6, or a portion thereof, can be isolated using standard molecular biology techniques and the sequence information provided herein. Using all or portion of the nucleic acid sequence of SEQ ID NO:1, 3, 4, or 6 as a hybridization probe, PD-L2 nucleic acid molecules can be isolated using standard hybridization and cloning techniques (e.g., as described in Sambrook, J. et al. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, 3, 4, or 6 can be isolated by the polymerase chain reaction (PCR) using synthetic oligonucleotide primers designed based upon the sequence of SEQ ID NO:1, 3, 4, or 6.

A nucleic acid molecule of the invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to PD-L2 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, 3, 4, or 6. This cDNA may comprise sequences encoding the human PD-L2 polypeptide (i.e., "the coding region", from nucleotides 274-1092), as well as 5' untranslated sequences (nucleotides 1-273) and 3' untranslated sequences (nucleotides 1093-1223) of SEQ ID NO:1. Alternatively, the nucleic acid molecule can comprise only the coding region of SEQ ID NO:1 (i.e., nucleotides 274-1092, corresponding to SEQ ID NO:3). Accordingly, in another embodiment, an isolated nucleic acid molecule of the invention comprises SEQ ID NO:3 and nucleotides 1-274 of SEQ ID NO:1. In yet another embodiment, the isolated nucleic acid molecule comprises SEQ ID NO:3 and nucleotides 1093-1223 of SEQ ID NO:1. In yet another embodiment, the nucleic acid molecule consists of the nucleotide sequence set forth as SEQ ID NO:1 or SEQ ID NO:3. In still another embodiment, the nucleic acid molecule can comprise the coding region of SEQ ID NO:1 (e.g., nucleotides 274-1092, corresponding to SEQ ID NO:3), as well as a stop codon (e.g., nucleotides 1093-1095 of SEQ ID NO:1).

This cDNA may also comprise sequences encoding the mouse PD-L2 polypeptide (i.e., the coding region, from nucleotides 210-950), as well as 5' untranslated sequences (nucleotides 1-209) and 3' untranslated sequences (nucleotides 951-1655) of SEQ ID NO:4. Alternatively, the nucleic acid molecule can comprise only the coding region of SEQ ID NO:4 (i.e., nucleotides 210-950, corresponding to SEQ ID NO:6). Accordingly, in another embodiment, an isolated nucleic acid molecule of the invention comprises SEQ ID NO:6 and nucleotides 1-210 of SEQ ID NO:4. In yet another embodiment, the isolated nucleic acid molecule comprises SEQ ID NO:6 and nucleotides 951-1655 of SEQ ID NO:4. In yet another embodiment, the nucleic acid molecule consists of the nucleotide sequence set forth as SEQ ID NO:4 or SEQ ID NO:6. In still another embodiment, the nucleic acid molecule can comprise the coding region of SEQ ID NO:4 (e.g., nucleotides 210-950, corresponding to SEQ ID NO:4), as well as a stop codon (e.g., nucleotides 951-953 of SEQ ID NO:4).

In another preferred embodiment, an isolated nucleic acid molecule of the invention comprises a nucleic acid molecule which is a complement of the nucleotide sequence shown in SEQ ID NO:1, 3, 4, or 6, or a portion of any of these nucleotide sequences. A nucleic acid molecule which is complementary to the nucleotide sequence shown in SEQ ID NO:1, 3, 4, or 6, is one which is sufficiently complementary to the nucleotide sequence shown in SEQ ID NO:1, 3, 4, or 6 such that it can hybridize to the nucleotide sequence shown in SEQ ID NO:1, 3, 4, or 6, respectively, thereby forming a stable duplex.

In still another preferred embodiment, an isolated nucleic acid molecule of the present invention comprises a nucleotide sequence which is at least about 70%, 75%, 80%, 85%, 90%, 91%, 92%, 93%, 94%, 95%, 96%, 97%, 98%, 99% or more identical to the entire length of the nucleotide sequence shown in SEQ ID NO:1, 3, 4, or 6, or a portion of any of these nucleotide sequences.

Moreover, the nucleic acid molecule of the invention can comprise only a portion of the nucleic acid sequence of SEQ ID NO:1, 3, 4, or 6, for example, a fragment which can be used as a probe or primer or a fragment which encodes a portion of a PD-L2 polypeptide, e.g., a biologically active portion of a PD-L2-polypeptide. The nucleotide sequences determined from the cloning of the human PD-L2 gene allow for the generation of probes and primers designed for use in identifying and/or cloning other PD-L2 family members, as well as PD-L2 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 3, 4, or 6; of an anti-sense sequence of SEQ ID NO:1, 3, 4, or 6; or of a naturally occurring allelic variant or mutant of SEQ ID NO:1, 3, 4, or 6.

In one embodiment, a nucleic acid molecule of the present invention comprises a nucleotide sequence which is greater than about 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150 or more nucleotides in length and hybridizes under stringent hybridization conditions to a nucleic acid molecule of SEQ ID NO:1, 3, 4, or 6, or the complement thereof. In a further embodiment, a nucleic acid molecule of the present invention comprises a nucleotide sequence which is greater than about 880-900, 900-950, 950-1000, 1000-1050, 1050-1100, 1100-1150 or more nucleotides in length and hybridizes under stringent hybridization conditions to a nucleic acid molecule of SEQ ID NO:1 or 3, or the complement thereof. In yet another embodiment, a nucleic acid molecule of the present invention comprises a nucleotide sequence which is greater than 50-100, 100-150, 150-200, 200-250, 250-300 or more nucleotides in length and hybridizes under stringent hybridization conditions to a nucleic acid molecule comprising nucleotides 1-358 of SEQ ID NO:1, or a complement thereof. In yet a further embodiment, a nucleic acid molecule of the present invention comprises a nucleotide sequence which is greater than about 50-100, 100-150, 150-200, 200-250, 250-300, 300-350, 350-400, 400-450, 450-500, 500-550, 550-600, 600-650, 650-700, 700-750, 750-800, 850-900, 900-950, 950-1000-1050-1100, 1100-1150 or more nucleotides in length, includes at least about 15 (i.e., 15 contiguous) nucleotides of the sequence comprising nucleotides 1-358 of SEQ ID NO:1, or a complement thereof, and hybridizes under stringent conditions to a nucleic acid molecule comprising the nucleotide sequence shown in SEQ ID NO:1, or a complement thereof.

Probes based on the PD-L2 nucleotide sequences can be used to detect transcripts or genomic sequences encoding the same or homologous polypeptides. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a PD-L2 polypeptide, such as by measuring a level of a PD-L2-encoding nucleic acid in a sample of cells from a subject e.g., detecting PD-L2 mRNA levels or determining whether a genomic PD-L2 gene has been mutated or deleted.

A nucleic acid fragment encoding a "biologically active portion of a PD-L2 polypeptide" can be prepared by isolating a portion of the nucleotide sequence of SEQ ID NO:1, 3, 4, or 6 which encodes a polypeptide having a PD-L2 biological activity (e.g., the ability to bind to its natural binding partner(s) (e.g., PD-1), and/or modulate immune cell activity), expressing the encoded portion of the PD-L2 polypeptide (e.g., by recombinant expression in vitro) and assessing the activity of the encoded portion of the PD-L2 polypeptide.

The invention further encompasses nucleic acid molecules that differ from the nucleotide sequence shown in SEQ ID NO:1, 3, 4, or 6 due to degeneracy of the genetic code and thus encode the same PD-L2 polypeptides as those encoded by the nucleotide sequence shown in SEQ ID NO:1, 3, 4, or 6. In another embodiment, an isolated nucleic acid molecule of the invention has a nucleotide sequence encoding a polypeptide having an amino acid sequence shown in SEQ ID NO:2 or 5.

In addition to the PD-L2 nucleotide sequences shown in SEQ ID NO:1, 3, 4, or 6, it will be appreciated by those skilled in the art that DNA sequence polymorphisms that lead to changes in the amino acid sequences of the PD-L2 polypeptides may exist within a population (e.g., the human population). Such genetic polymorphism in the PD-L2 genes may exist among individuals within a population due to natural allelic variation. As used herein, the terms "gene" and "recombinant gene" refer to nucleic acid molecules which include an open reading frame encoding a PD-L2 polypeptide, preferably a mammalian PD-L2 polypeptide, and can further include non-coding regulatory sequences, and introns.

Allelic variants of human or mouse PD-L2 include both functional and non-functional PD-L2 polypeptides. Functional allelic variants are naturally occurring amino acid sequence variants of the human or mouse PD-L2 polypeptide that maintain the ability to bind natural PD-L2 binding partner(s), e.g., PD-1, and/or modulate lymphocyte activation. Functional allelic variants will typically contain only conservative substitution of one or more amino acids of SEQ ID NO:2 or 5, or substitution, deletion or insertion of non-critical residues in non-critical regions of the polypeptide.

Non-functional allelic variants are naturally occurring amino acid sequence variants of the human or mouse PD-L2 polypeptide that do not have the ability to either bind natural PD-L2 binding partners, e.g., PD-1, and/or modulate any of the PD-L2 activities described herein. Non-functional allelic variants will typically contain a non-conservative substitution, deletion, or insertion or premature truncation of the amino acid sequence of SEQ ID NO:2 or 5, or a substitution, insertion or deletion in critical residues or critical regions of the polypeptide, e.g., in an IgV domain.

The present invention further provides non-human, non-mouse orthologues of the human or mouse PD-L2 polypeptide. Orthologues of the human or mouse PD-L2 polypeptide are polypeptides that are isolated from non-human, non-mouse organisms and possess the same PD-1-binding activity and/or lymphocyte activation-modulating activity of the PD-L2 polypeptide. Orthologues of the human or mouse PD-L2 polypeptide can readily be identified as comprising an amino acid sequence that is substantially identical to SEQ ID NO:2 or 5.

Moreover, nucleic acid molecules encoding other PD-L2 family members and, thus, which have a nucleotide sequence which differs from the PD-L2 sequences of SEQ ID NO:1, 3, 4, or 6 are intended to be within the scope of the invention. For example, another PD-L2 cDNA can be identified based on the nucleotide sequence of mouse or human PD-L2. Moreover, nucleic acid molecules encoding PD-L2 polypeptides from different species, and which, thus, have a nucleotide sequence which differs from the PD-L2 sequences of SEQ ID NO:1, 3, 4, or 6 are intended to be within the scope of the invention. For example, a monkey PD-L2 cDNA can be identified based on the nucleotide sequence of the mouse or human PD-L2.

Nucleic acid molecules corresponding to natural allelic variants and homologues of the PD-L2 cDNAs of the invention can be isolated based on their homology to the PD-L2 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the PD-L2 cDNAs of the invention can further be isolated by mapping to the same chromosome or locus as the PD-L2 gene.

Accordingly, in another embodiment, an isolated nucleic acid molecule of the invention is at least 15, 20, 25, 30 or more nucleotides in length and hybridizes under stringent conditions to the nucleic acid molecule comprising nucleotides 1-358 of the nucleotide sequence of SEQ ID NO:1, or nucleotides 1-85 of SEQ ID NO:3. In other embodiment, the nucleic acid is at least 880-900, 900-950, 950-1000, 1000-1050, 1050-1100, 1100-1150 or more nucleotides in length.

As used herein, the term "hybridizes under stringent conditions" is intended to describe conditions for hybridization and washing under which nucleotide sequences that are significantly identical or homologous to each other remain hybridized to each other.

Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual,* Sambrook et al., Cold Spring Harbor Press, Cold Spring Harbor, N.Y. (1989), chapters 7, 9 and 11. A preferred, non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further preferred, non-limiting example of stringent hybridization conditions includes hybridization at 6×SSC at 45° C., followed by one or more washes in 0.2×SSC, 0.1% SDS at 65° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4× or 6×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6 ($\log_{10}[Na^+]$)+0.41(%G+C)−(600/N), where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995 (or alternatively 0.2×SSC, 1% SDS).

Preferably, an isolated nucleic acid molecule of the invention that hybridizes under stringent conditions to the sequence of SEQ ID NO:1, 3, 4, or 6 corresponds to a naturally-occurring nucleic acid molecule. As used herein, a "naturally-occurring" nucleic acid molecule refers to an RNA or DNA molecule having a nucleotide sequence that occurs in nature (i.e., encodes a natural polypeptide).

In addition to naturally-occurring allelic variants of the PD-L2 sequences that may exist in the population, the skilled artisan will further appreciate that changes can be introduced by mutation into the nucleotide sequences of SEQ ID NO:1, 3, 4, or 6, thereby leading to changes in the amino acid sequence of the encoded PD-L2 polypeptides, without altering the functional ability of the PD-L2 polypeptides. For example, nucleotide substitutions leading to amino acid substitutions at "non-essential" amino acid residues can be made in the sequence of SEQ ID NO:1, 3, 4, or 6. A "non-essential" amino acid residue is a residue that can be altered from the wild-type sequence of PD-L2 (e.g., the sequence of SEQ ID NO:2 or 5) without altering the biological activity, whereas an "essential" amino acid residue is required for biological activity. For example, amino acid residues that are conserved among the PD-L2 polypeptides of the present invention, e.g., those present in an extracellular domain, are predicted to be particularly unamenable to alteration. Furthermore, additional amino acid residues that are conserved between the PD-L2 polypeptides of the present invention and other members of the PD-L2 family are not likely to be amenable to alteration.

Accordingly, another aspect of the invention pertains to nucleic acid molecules encoding PD-L2 polypeptides that contain changes in amino acid residues that are not essential for activity. Such PD-L2 polypeptides differ in amino acid sequence from SEQ ID NO:2 or 5, yet retain biological activity. In one embodiment, the isolated nucleic acid molecule comprises a nucleotide sequence encoding a polypeptide, wherein the polypeptide comprises an amino acid sequence at least about 71%, 75%, 80%, 85%, 90%, 91%, 92%, 93%, 94%, 95%, 96%, 97%, 98%, 99% or more identical to SEQ ID NO:2 or 5.

An isolated nucleic acid molecule encoding a PD-L2 polypeptide identical to the polypeptide of SEQ ID NO:2 or 5 can be created by introducing one or more nucleotide substitutions, additions or deletions into the nucleotide sequence of SEQ ID NO:1, 3, 4, or 6 such that one or more amino acid substitutions, additions or deletions are introduced into the encoded polypeptide. Mutations can be introduced into SEQ ID NO:1, 3, 4, or 6 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PD-L2 polypeptide is preferably replaced with another amino acid residue from the same side chain family. Alternatively, in another embodiment, mutations can be introduced randomly along all or part of a PD-L2 coding sequence, such as by saturation mutagenesis, and the resultant mutants can be screened for PD-L2 biological activity to identify mutants that retain activity. Following mutagenesis of SEQ ID NO:1, 3, 4, or 6, the encoded polypeptide can be expressed recombinantly and the activity of the polypeptide can be determined.

In a preferred embodiment, a mutant PD-L2 polypeptide can be assayed for the ability to bind to and/or modulate the activity of a natural PD-L2 binding partner, e.g., PD-1, modulate intra- or intercellular signaling, modulate activation of T lymphocytes, and/or modulate the immune response of an organism.

Yet another aspect of the invention pertains to isolated nucleic acid molecules encoding a PD-L2 fusion proteins. Such nucleic acid molecules, comprising at least a first nucleotide sequence encoding a PD-L2 protein, polypeptide or peptide operatively linked to a second nucleotide sequence encoding a non- a PD-L2 protein, polypeptide or peptide, can be prepared by standard recombinant DNA techniques.

In addition to the nucleic acid molecules encoding PD-L2 polypeptides described above, another aspect of the invention pertains to isolated nucleic acid molecules which are antisense thereto. An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PD-L2 coding strand, or to only a portion thereof. In one embodiment, an antisense nucleic acid molecule is antisense to a "coding region" of the coding strand of a nucleotide sequence encoding a PD-L2. The term "coding region" refers to the region of the nucleotide sequence comprising codons which are translated into amino acid residues (e.g., the coding region of human PD-L2 corresponds to SEQ ID NO:3). In another embodiment, the antisense nucleic acid molecule is antisense to a "noncoding region" of the coding strand of a nucleotide sequence encoding PD-L2. The term "noncoding region" refers to 5' and 3' sequences which flank the coding region that are not translated into amino acids (also referred to as 5' and 3' untranslated regions).

Given the coding strand sequences encoding human or mouse PD-L2 disclosed herein (e.g., SEQ ID NO:3 or 6, respectively), antisense nucleic acids of the invention can be designed according to the rules of Watson and Crick base pairing. The antisense nucleic acid molecule can be complementary to the entire coding region of PD-L2 mRNA, but more preferably is an oligonucleotide which is antisense to only a portion of the coding or noncoding region of PD-L2 mRNA. For example, the antisense oligonucleotide can be complementary to the region surrounding the translation start site of PD-L2 mRNA. An antisense oligonucleotide can be, for example, about 5, 10, 15, 20, 25, 30, 35, 40, 45 or 50 nucleotides in length. An antisense nucleic acid molecule of the invention can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PD-L2 polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res*. 15:6625-6641). The antisense nucleic acid molecule can also comprise a 2'-o-methylribonucleotide (Inoue et al. (1987) *Nucleic Acids Res*. 15:6131-6148) or a chimeric RNA-DNA analogue (Inoue et al. (1987) *FEBS Lett*. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585-591)) can be used to catalytically cleave PD-L2 mRNA transcripts to thereby inhibit translation of PD-L2 mRNA. A ribozyme having specificity for a PD-L2-encoding nucleic acid can be designed based upon the nucleotide sequence of a PD-L2 cDNA disclosed herein (i. e., SEQ ID NO:1, 3, 4, or 6). For example, a derivative of a *Tetrahymena* L-19 IVS RNA can be constructed in which the nucleotide sequence of the active site is complementary to the nucleotide sequence to be cleaved in a PD-L2-encoding mRNA. See, e.g., Cech et al., U.S. Pat. No. 4,987,071 and Cech et al., U.S. Pat. No. 5,116,742. Alternatively, PD-L2 mRNA can be used to select a catalytic RNA having a specific ribonuclease activity from a pool of RNA molecules. See, e.g., Bartel, D. and Szostak, J. W. (1993) *Science* 261: 1411-1418.

Alternatively, PD-L2 gene expression can be inhibited by targeting nucleotide sequences complementary to the regulatory region of the PD-L2 (e.g., the PD-L2 promoter and/or enhancers; e.g., nucleotides 1-273 of SEQ ID NO:1 or nucleotides 1-209 of SEQ ID NO:4) to form triple helical structures that prevent transcription of the PD-L2 gene in target cells. See generally, Helene, C. (1991) *Anticancer Drug Des.* 6(6): 569-84; Helene, C. et al. (1992) *Ann. N.Y. Acad. Sci.* 660:27-36; and Maher, L. J. (1992) *Bioessays* 14(12):807-15.

In yet another embodiment, the PD-L2 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) *Bioorg. Med. Chem.* 4(1):5-23). As used herein, the terms "peptide nucleic acids" or "PNAs" refer to nucleic acid mimics, e.g, DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) *Proc. Natl. Acad. Sci. USA* 93:14670-675.

PNAs of PD-L2 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of PD-L2 nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup and Nielsen (1996) supra)); or as probes or primers for DNA sequencing or hybridization (Hyrup and Nielsen (1996) supra; Perry-O'Keefe et al. (1996) supra).

In another embodiment, PNAs of PD-L2 can be modified (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PD-L2 nucleic acid molecules can be generated which may combine the advantageous properties of PNA and DNA. Such chimeras allow DNA recognition enzymes (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al. (1996) *Nucleic Acids Res.* 24 (17):3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a bridge between the PNA and the 5' end of DNA (Mag, M. et al. (1989) *Nucleic Acids Res.* 17:5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) *Biotechniques* 6:958-976) or intercalating agents (See, e.g., Zon (1988) *Pharm. Res.* 5:539-549). To this end, the oligonucleotide may be conjugated to another molecule (e.g., a peptide, hybridization triggered cross-linking agent, transport agent, or hybridization-triggered cleavage agent).

Alternatively, the expression characteristics of an endogenous PD-L2 gene within a cell line or microorganism may be modified by inserting a heterologous DNA regulatory element into the genome of a stable cell line or cloned microorganism such that the inserted regulatory element is operatively linked with the endogenous PD-L2 gene. For example, an endogenous PD-L2 gene which is normally "transcriptionally silent", i.e., a PD-L2 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous PD-L2 gene may be activated by insertion of a promiscuous regulatory element that works across cell types.

A heterologous regulatory element may be inserted into a stable cell line or cloned microorganism, such that it is operatively linked with an endogenous PD-L2 gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated PD-L2 Polypeptides and Anti-PD-L2 Antibodies

One aspect of the invention pertains to isolated PD-L2 polypeptides, and biologically active portions thereof, as well as polypeptide fragments suitable for use as immunogens to raise anti-PD-L2 antibodies. In one embodiment, native PD-L2 polypeptides can be isolated from cells or tissue sources by an appropriate purification scheme using standard protein purification techniques. In another embodiment, PD-L2 polypeptides are produced by recombinant DNA techniques. Alternative to recombinant expression, a PD-L2 protein or polypeptide can be synthesized chemically using standard peptide synthesis techniques.

An "isolated" or "purified" polypeptide or biologically active portion thereof is substantially free of cellular material or other contaminating proteins from the cell or tissue source from which the PD-L2 polypeptide is derived, or substantially free from chemical precursors or other chemicals when chemically synthesized. The language "substantially free of cellular material" includes preparations of PD-L2 polypeptide in which the polypeptide is separated from cellular components of the cells from which it is isolated or recombinantly produced. In one embodiment, the language "substantially free of cellular material" includes preparations of PD-L2 polypeptide having less than about 30% (by dry weight) of non-PD-L2 protein (also referred to herein as a "contaminating protein"), more preferably less than about 20% of non-PD-L2 protein, still more preferably less than about 10% of non-PD-L2 protein, and most preferably less than about 5% non-PD-L2 protein. When the PD-L2 polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PD-L2 polypeptide in which the polypeptide is separated from chemical precursors or other chemicals which are involved in the synthesis of the polypeptide. In one embodiment, the language "substantially free of chemical precursors or other chemicals" includes preparations of PD-L2 polypeptide having less than about 30% (by dry weight) of chemical precursors or non-PD-L2 chemicals, more preferably less than about 20% chemical precursors or non-PD-L2 chemicals, still more preferably less than about 10% chemical precursors or non-PD-L2 chemicals, and most preferably less than about 5% chemical precursors or non-PD-L2 chemicals.

As used herein, a "biologically active portion" of a PD-L2 polypeptide includes a fragment of a PD-L2 polypeptide which participates in an interaction between a PD-L2 molecule and a non-PD-L2 molecule, e.g., a natural ligand of PD-L2, e.g., PD-1. Biologically active portions of a PD-L2 polypeptide include peptides comprising amino acid sequences sufficiently identical to or derived from the amino acid sequence of the PD-L2 polypeptide, e.g., the amino acid sequence shown in SEQ ID NO:2 or 5, which include fewer amino acids than the full length PD-L2 polypeptides, and exhibit at least one activity of a PD-L2 polypeptide. Typically, biologically active portions comprise a domain or motif with at least one activity of the PD-L2 polypeptide, e.g., modulating PD-1 activity. A biologically active portion of a PD-L2 polypeptide can be a polypeptide which is, for example, 25, 50, 75, 100, 125, 150, 175, 200, 225 or more amino acids in length. Biologically active portions of a PD-L2 polypeptide can be used as targets for developing agents which modulate a PD-L2-mediated activity, e.g., immune cell activation.

In one embodiment, a biologically active portion of a PD-L2 polypeptide comprises at least a portion of an extracellular domain. It is to be understood that a preferred biologically active portion of a PD-L2 polypeptide of the present invention may contain at least a portion of an extracellular domain (e.g., comprising an IgV and/or an IgC domain), and one or more of the following domains: a signal peptide domain, a transmembrane domain, and a cytoplasmic domain. Moreover, other biologically active portions, in which other regions of the polypeptide are deleted, can be prepared by recombinant techniques and evaluated for one or more of the functional activities of a native PD-L2 polypeptide.

In a preferred embodiment, the PD-L2 polypeptide has an amino acid sequence shown in SEQ ID NO:2 or 5. In other embodiments, the PD-L2 polypeptide is substantially identical to SEQ ID NO:2 or 5, and retains the functional activity of the polypeptide of SEQ ID NO:2 or 5, yet differs in amino acid sequence due to natural allelic variation or mutagenesis, as described in detail in subsection I above. Accordingly, in another embodiment, the PD-L2 polypeptide is a polypeptide which comprises an amino acid sequence at least about 71%, 75%, 80%, 85%, 90%, 91%, 92%, 93%, 94%, 95%, 96%, 97%, 98%, 99% or more identical to SEQ ID NO:2 or 5.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the human PD-L2 amino acid sequence of SEQ ID NO:2 having 273 amino acid residues, at least 82, preferably at least 109, more preferably at least 137, even more preferably at least 164, and even more preferably at least 191, 218, 246 or more amino acid residues are aligned; when aligning a second amino acid sequence to the mouse PD-L2 amino acid sequence of SEQ ID NO:5 having 247 amino acid residues, at least 74, preferably at least 99, more preferably at least 124, even more preferably at least 148, and even more preferably at least 173, 198, 222 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970)) algorithm which has been incorporated into the GAP program in the GCG software package (available online through the Genetics Computer Group), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the Genetics Computer Group), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers, E. and Miller, W. (*Comput. Appl. Biosci.* 4:11-17 (1988)) which has been incorporated into the ALIGN program (version 2.0 or 2.0 U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to PD-L2 nucleic acid molecules of the invention. BLAST protein searches can be performed with the XBLAST program, score=100, wordlength=3 to obtain amino acid sequences homologous to PD-L2 polypeptide molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used. See the internet website for the National Center for Biotechnology Information.

The invention also provides PD-L2 chimeric or fusion proteins. As used herein, a PD-L2 "chimeric protein" or "fusion protein" comprises a PD-L2 polypeptide operatively linked to a non-PD-L2 polypeptide. A "PD-L2 polypeptide" refers to a polypeptide having an amino acid sequence corresponding to a PD-L2 molecule, whereas a "non-PD-L2 polypeptide" refers to a polypeptide having an amino acid sequence corresponding to a polypeptide which is not substantially homologous to the PD-L2 polypeptide, e.g., a polypeptide which is different from the PD-L2 polypeptide and which is derived from the same or a different organism. Within a PD-L2 fusion protein, the PD-L2 polypeptide can correspond to all or a portion of a PD-L2 polypeptide. In a preferred embodiment, a PD-L2 fusion protein comprises at least one biologically active portion of a PD-L2 polypeptide. In another preferred embodiment, a PD-L2 fusion protein comprises at least two domains of a PD-L2 polypeptide. Within the fusion protein, the term "operatively linked" is intended to indicate that the PD-L2 polypeptide and the non-PD-L2 polypeptide are fused in-frame to each other. The non-PD-L2 polypeptide can be fused to the N-terminus or C-terminus of the PD-L2 polypeptide and corresponds to a moiety that alters the solubility, binding affinity, stability, or valency of the PD-L2 polypeptide.

For example, in one embodiment, the fusion protein is a GST-PD-L2 fusion protein in which the PD-L2 sequences are fused to the C-terminus of the GST sequences. Such fusion proteins can facilitate the purification of recombinant PD-L2.

In another embodiment, the fusion protein is a PD-L2 polypeptide containing a heterologous signal sequence at its N-terminus. In certain host cells (e.g., mammalian host cells), expression and/or secretion of PD-L2 can be increased through use of a heterologous signal sequence.

In a preferred embodiment, the fusion protein is an Ig-PD-L2 fusion protein in which the PD-L2 sequences are fused to a portion of an Ig molecule. The Ig portion of the fusion protein can include and immunoglobulin constant region, e.g., a human Cγ1 domain or a Cγ4 domain (e.g., the hinge, CH2, and CH3 regions of human IgCγ1 or human IgCγ4 (see, e.g., Capon et al., U.S. Pat. Nos. 5,116,964; 5,580,756; 5,844, 095, and the like, incorporated herein by reference). A resulting fusion protein may have altered PD-L2 solubility, binding affinity, stability and/or valency (i.e., the number of binding sites per molecule) and may increase the efficiency of protein purification.

Particularly preferred PD-L2 Ig fusion proteins include an extracellular domain portion of PD-L2 coupled to an immunoglobulin constant region (e.g, the Fc region). The immunoglobulin constant region may contain genetic modifications which reduce or eliminate effector activity inherent in the immunoglobulin structure. For example, DNA encoding an extracellular portion of a PD-L2 polypeptide can be joined to DNA encoding the hinge, CH2, and CH3 regions of human IgGγ1 and/or IgGγ4 modified by site-directed mutagenesis, e.g., as taught in WO 97/28267.

The PD-L2 fusion proteins of the invention can be incorporated into pharmaceutical compositions and administered to a subject in vivo. The PD-L2 fusion proteins can be used to affect the bioavailability of a PD-L2 binding partner, e.g., PD-1. Use of PD-L2 fusion proteins may be useful therapeutically for the treatment of conditions or disorders that would benefit from modulation of the immune response.

Moreover, the PD-L2-fusion proteins of the invention can be used as immunogens to produce anti-PD-L2 antibodies in a subject, to purify PD-L2-binding proteins, and in screening assays to identify molecules which inhibit the interaction of PD-L2 with its natural binding partner, e.g., PD-1.

Preferably, a PD-L2 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology,* Ausubel et al., eds., John Wiley & Sons: 1992). Moreover, many expression vectors are commercially available that already encode a fusion moiety (e.g., a GST polypeptide). A PD-L2-encoding nucleic acid can be cloned into such an expression vector such that the fusion moiety is linked in-frame to the PD-L2 polypeptide.

The present invention also pertains to variants of the PD-L2 polypeptides which function as either PD-L2 agonists (mimetics) or as PD-L2 antagonists. Variants of the PD-L2 polypeptides can be generated by mutagenesis, e.g., discrete point mutation or truncation of a PD-L2 polypeptide. An agonist of the PD-L2 polypeptides can retain substantially the same, or a subset, of the biological activities of the naturally occurring form of a PD-L2 polypeptide. An antagonist of a PD-L2 polypeptide can inhibit one or more of the activities of the naturally occurring form of the PD-L2 polypeptide by, for example, competitively modulating a PD-L2-mediated activity of a PD-L2 polypeptide. Thus, specific biological effects can be elicited by treatment with a variant of limited function. In one embodiment, treatment of a subject with a variant having a subset of the biological activities of the naturally occurring form of the polypeptide has fewer side effects in a subject relative to treatment with the naturally occurring form of the PD-L2 polypeptide.

In one embodiment, variants of a PD-L2 polypeptide which function as either PD-L2 agonists (mimetics) or as PD-L2 antagonists can be identified by screening combinatorial libraries of mutants, e.g., truncation mutants, of a PD-L2 polypeptide for PD-L2 polypeptide agonist or antagonist activity. In one embodiment, a variegated library of PD-L2 variants is generated by combinatorial mutagenesis at the nucleic acid level and is encoded by a variegated gene library. A variegated library of PD-L2 variants can be produced by, for example, enzymatically ligating a mixture of synthetic oligonucleotides into gene sequences such that a degenerate set of potential PD-L2 sequences is expressible as individual polypeptides, or alternatively, as a set of larger fusion proteins (e.g., for phage display) containing the set of PD-L2 sequences therein. There are a variety of methods which can be used to produce libraries of potential PD-L2 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PD-L2 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acids Res.* 11:477).

In addition, libraries of fragments of a PD-L2 polypeptide coding sequence can be used to generate a variegated population of PD-L2 fragments for screening and subsequent selection of variants of a PD-L2 polypeptide. In one embodiment, a library of coding sequence fragments can be generated by treating a double stranded PCR fragment of a PD-L2 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PD-L2 polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PD-L2 polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PD-L2 variants (Arkin and Youvan (1992) *Proc. Natl. Acad. Sci. USA* 89:7811-7815; Delagrave et al. (1993) *Protein Eng.* 6(3):327-331).

In one embodiment, cell-based assays can be exploited to analyze a variegated PD-L2 library. For example, a library of expression vectors can be transfected into a cell line. The transfected cells are then contacted with PD-1-expressing cells and the effect of expression of the mutant on interaction of wild-type PD-L2 with its natural ligand(s), e.g., PD-1, can be detected. Plasmid DNA can then be recovered from the cells which score for inhibition of signaling via PD-1 (leading to T cell upregulation), or alternatively, potentiation of signaling by PD-1 (leading to T cell downregulation), and the individual clones further characterized.

In addition to PD-L2 polypeptides consisting only of naturally-occurring amino acids, PD-L2 peptidomimetics are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) *Adv. Drug Res.* 15:29; Veber and Freidinger (1985) *TINS* p.392; and Evans et al. (1987) *J. Med. Chem* 30:1229, which are incorporated herein by reference) and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i e., a polypeptide that has a biological or pharmacological activity), such as human or mouse PD-L2, but have one or more peptide linkages optionally replaced by a linkage selected from the group consisting of: —CH2NH—, —CH2S—, —CH2—CH2—, —CH=CH— (cis and trans), —COCH2—, —CH(OH)CH2—, and —CH2SO—, by methods known in the art and further described in the following references: Spatola, A. F. in *Chemistry and Biochemistry of Amino Acids, Peptides, and Proteins* Weinstein, B., ed., Marcel Dekker, New York, p. 267 (1983); Spatola, A. F., Vega Data (March 1983), Vol. 1, Issue 3, "Peptide Backbone Modifications"; Morley, J. S. (1980) *Trends. Pharm. Sci. pp.*463-468; Hudson, D. et al. (1979) *Int. J. Pept. Prot. Res.* 14:177-185 (—CH2NH—, CH2CH2—); Spatola, A. F. et al. (1986) *Life. Sci.* 38:1243-1249 (—CH2—S); Hann, M. M. (1982) *J. Chem. Soc. Perkin. Trans. I* 307-314 (—CH—CH—, cis and trans); Almquist, R. G. et al. (1980) *J. Med. Chem.* 23:1392-1398 (—COCH2—); Jennings-White, C. et al. (1982) *Tetrahedron Lett.* 23:2533 (—COCH2—); Szelke, M. et al., European Patent Application No. EP 45665 (1982) CA: 97:39405 (—CH(OH) CH2—); Holladay, M. W. et al. (1983) *Tetrahedron. Lett.* 24:4401-4404 (—C(OH)CH2—); and Hruby, V. J. (1982) *Life Sci.* 31:189-199 (—CH2—S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetic.

Systematic substitution of one or more amino acids of a PD-L2 amino acid sequence with a D-amino acid of the same type (e.g., D-lysine in place of L-lysine) can be used to generate more stable peptides. In addition, constrained peptides comprising a PD-L2 amino acid sequence or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences of the PD-L2 polypeptides identified herein will enable those of skill in the art to produce polypeptides corresponding to PD-L2 peptide sequences and sequence variants thereof. Such polypeptides can be produced in prokaryotic or eukaryotic host cells by expression of polynucleotides encoding a PD-L2 peptide sequence, frequently as part of a larger polypeptide. Alternatively, such peptides can be synthesized by chemical methods. Methods for expression of heterologous polypeptides in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology,* Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11:255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins,* Wiley Publishing, which are incorporated herein by reference).

Peptides can be produced, typically by direct chemical synthesis, and used e.g., as agonists or antagonists of a PD-L2/PD-1 interaction. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides can be used therapeutically to treat disease, e.g., by altering costimulation in a patient.

An isolated PD-L2 polypeptide, or a portion or fragment thereof, can be used as an immunogen to generate antibodies that bind PD-L2 using standard techniques for polyclonal and monoclonal antibody preparation. A full-length PD-L2 polypeptide can be used or, alternatively, the invention provides antigenic peptide fragments of PD-L2 for use as immunogens. In one embodiment, an antigenic peptide of PD-L2 comprises at least 8 amino acid residues of the amino acid sequence shown in SEQ ID NO:2 or 5 and encompasses an epitope of PD-L2 such that an antibody raised against the peptide forms a specific immune complex with the PD-L2 polypeptide. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of PD-L2 that are located in the extracellular domain of the polypeptide, e.g., hydrophilic regions, as well as regions with high antigenicity.

A PD-L2 immunogen typically is used to prepare antibodies by immunizing a suitable subject (e.g., rabbit, goat, mouse, or other mammal) with the immunogen. An appropriate immunogenic preparation can contain, for example, recombinantly expressed PD-L2 polypeptide or a chemically synthesized PD-L2 polypeptide. The preparation can further include an adjuvant, such as Freund's complete or incomplete adjuvant, or similar immunostimulatory agent. Immunization of a suitable subject with an immunogenic PD-L2 preparation induces a polyclonal anti-PD-L2 antibody response.

Accordingly, another aspect of the invention pertains to anti-PD-L2 antibodies. The term "antibody" as used herein refers to immunoglobulin molecules and immunologically active portions of immunoglobulin molecules, i.e., molecules that contain an antigen binding site which specifically binds (immunoreacts with) an antigen, such as a PD-L2. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PD-L2 molecules. The term "monoclonal antibody" or "monoclonal antibody composition", as used herein, refers to a population of antibody molecules that contain only one species of an antigen binding site capable of immunoreacting with a particular epitope of PD-L2. A monoclonal antibody composition thus typically displays a single binding affinity for a particular PD-L2 polypeptide with which it immunoreacts.

Polyclonal anti-PD-L2 antibodies can be prepared as described above by immunizing a suitable subject with a PD-L2 immunogen. The anti-PD-L2 antibody titer in the immunized subject can be monitored over time by standard techniques, such as with an enzyme linked immunosorbent assay (ELISA) using immobilized PD-L2. If desired, the antibody molecules directed against PD-L2 can be isolated from the mammal (e.g., from the blood) and further purified by well known techniques, such as protein A chromatography to obtain the IgG fraction. At an appropriate time after immunization, e.g, when the anti-PD-L2 antibody titers are highest, antibody-producing cells can be obtained from the subject and used to prepare monoclonal antibodies by standard techniques, such as the hybridoma technique originally described by Kohler and Milstein (1975) *Nature* 256:495-497 (see also Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy,* Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses,* Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with a PD-L2 immunogen as described above, and the culture supernatants of the resulting hybridoma cells are screened to identify a hybridoma producing a monoclonal antibody that binds PD-L2.

Any of the many well known protocols used for fusing lymphocytes and immortalized cell lines can be applied for the purpose of generating an anti-PD-L2 monoclonal antibody (see, e.g., Galfre, G. et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PD-L2, e.g., using a standard ELISA assay.

Further methods for producing antibodies that bind PD-L2 are described in Examples 4 and 5.

Alternative to preparing monoclonal antibody-secreting hybridomas, a monoclonal anti-PD-L2 antibody can be identified and isolated by screening a recombinant combinatorial immunoglobulin library (e.g., an antibody phage display library) with PD-L2 to thereby isolate immunoglobulin library members that bind PD-L2. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication WO 92/20791; Markland et al., PCT International Publication No. WO 92/15679; Breitling et al., PCT International Publication WO 93/01288; McCafferty et al., PCT International Publication No. WO 92/01047; Garrard et al., PCT International Publication No. WO 92/09690; Ladner et al., PCT International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-PD-L2 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al., International Application No. PCT/US86/02269; Akira et al., European Patent Application 184,187; Taniguchi, M., European Patent Application 171,496; Morrison et al., European Patent Application 173,494; Neuberger et al., PCT International Publication No. WO 86/01533; Cabilly et al., U.S. Pat. No. 4,816,567; Cabilly et al., European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559; Morrison, S. L. (1985) *Science* 229:1202-1207; Oi et al. (1986) *Biotechniques* 4:214; Winter, U.S. Pat. No. 5,225,539; Jones et al. (1986) *Nature* 321:552-525; Verhoeyen et al. (1988) *Science* 239:1534; and Beidler et al. (1988) *J. Immunol.* 141:4053-4060.

An anti-PD-L2 antibody (e.g., monoclonal antibody) can be used to isolate PD-L2 by standard techniques, such as affinity chromatography or immunoprecipitation. An anti-PD-L2 antibody can facilitate the purification of natural PD-L2 from cells and of recombinantly produced PD-L2 expressed in host cells. Moreover, an anti-PD-L2 antibody can be used to detect PD-L2 polypeptide (e.g., in a cellular lysate or cell supernatant) in order to evaluate the abundance and pattern of expression of the PD-L2 polypeptide. Anti-PD-L2 antibodies can be used diagnostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid molecule encoding a PD-L2 polypeptide (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PD-L2 polypeptides, mutant forms of PD-L2 polypeptides, fusion proteins, and the like).

The recombinant expression vectors of the invention can be designed for expression of PD-L2 polypeptides in prokaryotic or eukaryotic cells. For example, PD-L2 polypeptides can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of polypeptides in prokaryotes is most often carried out in *E. coli* with vectors containing constitutive or inducible promoters directing the expression of either fusion or non-fusion proteins. Fusion vectors add a number of amino acids to a polypeptide encoded therein, usually to the amino terminus of the recombinant polypeptide. Such fusion vectors typically serve three purposes: 1) to increase expression of recombinant polypeptide; 2) to increase the solubility of the recombinant polypeptide; and 3) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant polypeptide.

Purified fusion proteins can be utilized in PD-L2 activity assays (e.g., direct assays or competitive assays described in detail below), or to generate antibodies specific for PD-L2 polypeptides, for example. In a preferred embodiment, a PD-L2 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

Examples of suitable inducible non-fusion *E. coli* expression vectors include pTrc (Amann et al. (1988) *Gene* 69:301-315) and pET 11d (Studier et al. (1990) *Methods Enzymol.* 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant polypeptide expression in *E. coli* is to express the polypeptide in a host bacteria with an impaired capacity to proteolytically cleave the recombinant polypeptide (Gottesman, S. (1990) *Methods Enzymol.* 185:119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the PD-L2 expression vector is a yeast expression vector. Examples of vectors for expression in yeast *S. cerevisiae* include pYepSec1 (Baldari et al. (1987) *EMBO J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and picZ (Invitrogen Corp, San Diego, Calif.).

Alternatively, PD-L2 polypeptides can be expressed in insect cells using baculovirus expression vectors. Baculovirus vectors available for expression of polypeptides in cultured insect cells (e.g., Sf9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual. 2nd ed., Cold Spring Harbor Laboratory,* Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PD-L2 mRNA. Regulatory sequences operatively linked to a nucleic acid molecule cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics,* Vol. 1(1) 1986.

Another aspect of the invention pertains to host cells into which a PD-L2 nucleic acid molecule of the invention is introduced, e.g., a PD-L2 nucleic acid molecule within a recombinant expression vector or a PD-L2 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PD-L2 polypeptide can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual. 2nd, ed., Cold Spring Harbor Laboratory,* Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PD-L2 polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a PD-L2 polypeptide. Accordingly, the invention further provides methods for producing a PD-L2 polypeptide using the host cells of the invention. In one embodiment, the method comprises culturing the host cell of the invention (into which a recombinant expression vector encoding a PD-L2 polypeptide has been introduced) in a suitable medium such that a PD-L2 polypeptide is produced. In another embodiment, the method further comprises isolating a PD-L2 polypeptide from the medium or the host cell.

The host cells of the invention can also be used to produce non-human transgenic animals. For example, in one embodiment, a host cell of the invention is a fertilized oocyte or an embryonic stem cell into which PD-L2-coding sequences have been introduced. Such host cells can then be used to create non-human transgenic animals in which exogenous PD-L2 sequences have been introduced into their genome or homologous recombinant animals in which endogenous PD-L2 sequences have been altered. Such animals are useful for studying the function and/or activity of a PD-L2 and for identifying and/or evaluating modulators of PD-L2 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PD-L2 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a PD-L2-encoding nucleic acid into the male pronuclei of a fertilized oocyte, e.g., by microinjection, retroviral infection, and allowing the oocyte to develop in a pseudopregnant female foster animal. The PD-L2 cDNA sequence of SEQ ID NO:1 or 4 can be introduced as a transgene into the genome of a non-human animal. Alternatively, a nonhuman homologue of a human PD-L2 gene, such as a monkey or rat PD-L2 gene, can be used as a transgene. Alternatively, a PD-L2 gene homologue, such as another PD-L2 family member, can be isolated based on hybridization to the PD-L2 cDNA sequences of SEQ ID NO:1, 3, 4, or 6 (described further in subsection I above) and used as a transgene. Intronic sequences and polyadenylation signals can also be included in the transgene to increase the efficiency of expression of the transgene. A tissue-specific regulatory sequence(s) can be operably linked to a PD-L2 transgene to direct expression of a PD-L2 polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of a PD-L2 transgene in its genome and/or expression of PD-L2 mRNA in tissues or cells of the animals. A transgenic founder animal can then be used to breed additional animals carrying the transgene. Moreover, transgenic animals carrying a transgene encoding a PD-L2 polypeptide can further be bred to other transgenic animals carrying other transgenes.

To create a homologous recombinant animal, a vector is prepared which contains at least a portion of a PD-L2 gene into which a deletion, addition or substitution has been introduced to thereby alter, e.g., functionally disrupt, the PD-L2 gene. The PD-L2 gene can be a human gene (e.g., the cDNA of SEQ ID NO:1 or 3), but more preferably, is a non-human homologue of a human PD-L2 gene (e.g., a cDNA isolated by stringent hybridization with the nucleotide sequence of SEQ ID NO:1, 3, 4, or 6). For example, a mouse PD-L2 gene (e.g., the cDNA of SEQ ID NO:3 or 6) can be used to construct a homologous recombination nucleic acid molecule, e.g., a vector, suitable for altering an endogenous PD-L2 gene in the mouse genome. In a preferred embodiment, the homologous recombination nucleic acid molecule is designed such that, upon homologous recombination, the endogenous PD-L2 gene is functionally disrupted (i.e., no longer encodes a functional polypeptide; also referred to as a "knock out" vector). Alternatively, the homologous recombination nucleic acid molecule can be designed such that, upon homologous recombination, the endogenous PD-L2 gene is mutated or otherwise altered but still encodes functional polypeptide (e.g., the upstream regulatory region can be altered to thereby alter the expression of the endogenous PD-L2 polypeptide). In the homologous recombination nucleic acid molecule, the altered portion of the PD-L2 gene is flanked at its 5' and 3' ends by additional nucleic acid sequence of the PD-L2 gene to allow for homologous recombination to occur between the exogenous PD-L2 gene carried by the homologous recombination nucleic acid molecule and an endogenous PD-L2 gene in a cell, e.g., an embryonic stem cell. The additional flanking PD-L2 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced PD-L2 gene has homologously recombined with the endogenous PD-L2 gene are selected (see e.g., Li, E. et al. (1992) *Cell* 69:915). The selected cells can then be injected into a blastocyst of an animal (e.g., a mouse) to form aggregation chimeras (see e.g., Bradley, A. in *Teratocarcinomas and Embryonic Stem Cells: A Practical Approach,* Robertson, E. J., ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823-829 and in PCT International Publication Nos. WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected polypeptide are required. Such animals can be provided through the construction of "double" transgenic animals, e.g., by mating two transgenic animals, one containing a transgene encoding a selected polypeptide and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to the morula or blastocyte stage and then transferred to pseudopregnant female foster animal. The offspring borne of this female foster animal will be a clone of the animal from which the cell, e.g., the somatic cell, is isolated.

IV. Pharmaceutical Compositions

The PD-L2 molecules, e.g, the PD-L2 nucleic acid molecules, fragments of PD-L2 polypeptides, and anti-PD-L2 antibodies (also referred to herein as "active compounds" or "modulating agents") of the invention can be incorporated into pharmaceutical compositions suitable for administration. Such compositions typically comprise the nucleic acid molecule, polypeptide, or antibody and a carrier, e.g., a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., modulating agents such as a PD-L2 nucleic acid molecule, a fragment of a PD-L2 polypeptide, an anti-PD-L2 antibody, or a combination of an anti-PD-L2 antibody and an anti-PD-L1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity of PD-L2. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the scope of knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such polypeptides may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications,* Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy,* Baldwin et al. (eds.), pp. 303-16 (Academic Press 1985); and Thorpe et al. "The Preparation And Cytotoxic Properties Of Antibody-Toxin Conjugates", *Immunol. Rev.* 62:119-58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The PD-L2 molecules, e.g., the PD-L2 nucleic acid molecules, polypeptides, polypeptide homologues, and antibodies described herein can be used in one or more of the following methods: a) screening assays; b) predictive medicine (e.g., diagnostic assays, prognostic assays, and monitoring clinical trials); and c) methods of treatment (e.g., therapeutic and prophylactic, e.g., by up- or down-modulating the immune response). As described herein, a PD-L2 polypeptide of the invention has one or more of the following activities: 1) binds to and/or modulates the activity of its natural binding partner(s), e.g., PD-1, 2) modulates intra- or intercellular signaling, 3) modulates activation of T lymphocytes, 4) modulates the immune response of an organism, e.g., a mammalian organism, such as a mouse or human.

The isolated nucleic acid molecules of the invention can be used, for example, to express PD-L2 polypeptide (e.g., via a recombinant expression vector in a host cell in gene therapy applications), to detect PD-L2 mRNA (e.g., in a biological sample) or a genetic alteration in a PD-L2 gene, and to modulate PD-L2 activity, as described further below. The PD-L2 polypeptides can be used to treat conditions or disorders characterized by insufficient or excessive production of a PD-L2 polypeptide or production of PD-L2 inhibitors. In addition, the PD-L2 polypeptides can be used to screen for naturally occurring PD-L2 binding partner(s) (in addition to PD-1), to screen for drugs or compounds which modulate PD-L2 activity, as well as to treat conditions or disorders characterized by insufficient or excessive production of PD-L2 polypeptide or production of PD-L2 polypeptide forms which have decreased, aberrant or unwanted activity compared to PD-L2 wild-type polypeptide (e.g., immune system disorders such as severe combined immunodeficiency, multiple sclerosis, systemic lupus erythematosus, type I diabetes mellitus, lymphoproliferative syndrome, inflammatory bowel disease, allergies, asthma, graft-versus-host disease, and transplant rejection; immune responses to infectious pathogens such as bacteria and viruses; and immune system cancers such as lymphomas and leukemias). Moreover, the anti-PD-L2 antibodies of the invention can be used to detect and isolate PD-L2 polypeptides, regulate the bioavailability of PD-L2 polypeptides, and modulate PD-L2 activity, e.g., by modulating the interaction between PD-L2 and its natural binding partner(s) (e.g., PD-1).

A. Screening Assays:

The invention provides a method (also referred to herein as a "screening assay") for identifying modulators, i.e., candidate or test compounds or agents (e.g., peptides, peptidomimetics, small molecules or other drugs) which bind to PD-L2 polypeptides, have a stimulatory or inhibitory effect on, for example, PD-L2 expression or PD-L2 activity, or have a stimulatory or inhibitory effect on the interaction between PD-L2 and its natural binding partner(s), e.g., PD-1.

In one embodiment, the invention provides assays for screening candidate or test compounds which bind to the PD-L2 protein or polypeptide or biologically active portion thereof, e.g., modulate the ability of the PD-L2 polypeptide to interact with its natural binding partner(s). In a preferred embodiment, the binding partner is PD-1. In another embodiment, the invention provides assays for screening candidate or test compounds which bind to or modulate the activity of a PD-L2 protein or polypeptide or biologically active portion thereof (e.g., cofactor or coenzyme analogs, or inhibitory molecules).

In a preferred embodiment, the invention provides assays for screening candidate or test compounds which have a stimulatory or inhibitory effect on the interaction between PD-L2 and its natural binding partner(s). In an exemplary embodiment, the binding partner is PD-1. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or phage (Scott and Smith (1990) *Science* 249:386-390; Devlin (1990) *Science* 249:404-406; Cwirla et al. (1990) *Proc. Natl. Acad Sci. USA* 87:6378-6382; Felici (1991) *J. Mol. Biol.* 222:301-310; Ladner supra.).

In one embodiment, an assay is a cell-based assay in which a cell which expresses a PD-L2 polypeptide or biologically active portion thereof is contacted with a test compound, and the ability of the test compound to modulate PD-L2 activity is determined. Determining the ability of the test compound to modulate PD-L2 activity can be accomplished by monitoring, for example, the ability of PD-L2 to bind to its natural binding partner(s), e.g., PD-1, and modulate immune cell activity. The immune cell can be, e.g., a T cell, a B cell, or a myeloid cell. Determining the ability of the test compound to modulate PD-L2 binding to PD-1 can be accomplished, for example, by coupling PD-1 with a radioisotope or enzymatic label such that binding of the PD-1 to PD-L2 can be determined by detecting the labeled PD-1 in a complex. Alternatively, PD-L2 could be coupled with a radioisotope or enzymatic label to monitor the ability of a test compound to modulate PD-L2 binding to PD-1 in a complex. Determining the ability of the test compound to bind PD-L2 can be accomplished, for example, by coupling the compound with a radioisotope or enzymatic label such that binding of the compound to PD-L2 can be determined by detecting the labeled PD-L2 compound in a complex. For example, compounds (e.g, PD-1) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., PD-1) to interact with PD-L2 without the labeling of any of the interactants. For example, a microphysiometer can be used to detect the interaction of a compound with PD-L2 without the labeling of either the compound or the PD-L2 (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PD-L2.

In another embodiment, an assay is a cell-based assay comprising contacting a cell expressing a PD-L2 binding partner with a test compound and determining the ability of the test compound to modulate (e.g., stimulate or inhibit) the activity of the PD-L2 binding partner. In a preferred embodiment, the binding partner is PD-1. Determining the ability of the test compound to modulate the activity of a PD-L2 binding partner can be accomplished, for example, by determining the ability of the PD-L2 polypeptide to bind to or interact with the PD-L2 binding partner.

Determining the ability of the PD-L2 polypeptide, or a biologically active fragment thereof, to bind to or interact with a PD-L2 binding partner, e.g., PD-1, can be accomplished by one of the methods described above for determining direct binding. In a preferred embodiment, determining the ability of the PD-L2 polypeptide to bind to or interact with a PD-L2 binding partner can be accomplished by determining the activity of the binding partner. For example, the activity of the binding partner can be determined by detecting induction of a cellular second messenger (e.g., tyrosine kinase or phosphatase activity), detecting catalytic/enzymatic activity of an appropriate substrate, detecting the induction of a reporter gene (comprising a target-responsive regulatory element operatively linked to a nucleic acid encoding a detectable marker, e.g., luciferase), or detecting a target-regulated cellular response. For example, determining the ability of the PD-L2 polypeptide to bind to or interact with a natural PD-L2 binding partner, e.g., PD-1, can be accomplished by measuring the ability of a compound to modulate immune cell costimulation or inhibition in a proliferation assay, or by interfering with the ability of a PD-L2 polypeptide to bind to antibodies that recognize a portion of the PD-L2 polypeptide. In one embodiment, compounds that modulate T cell activation can be identified by determining the ability of a compound to modulate T cell proliferation or cytokine production. In a preferred embodiment, compounds that modulate T cell activation can be identified by determining the ability of a compound to modulate T cell proliferation or cytokine production at more than one antigen concentration.

In yet another embodiment, an assay of the present invention is a cell-free assay in which a PD-L2 polypeptide or biologically active portion thereof is contacted with a test compound and the ability of the test compound to bind to the PD-L2 polypeptide or biologically active portion thereof is determined. Preferred biologically active portions of the PD-L2 polypeptides to be used in assays of the present invention include fragments which participate in interactions with non-PD-L2 molecules, e.g., at least a portion of an extracellular domain which binds to a PD-L2 binding partner. In a further preferred embodiment, the binding partner is PD-1. Binding of the test compound to the PD-L2 polypeptide can be determined either directly or indirectly as described above. In a preferred embodiment, the assay includes contacting the PD-L2 polypeptide or biologically active portion thereof with a known compound which binds PD-L2 to form an assay mixture, contacting the assay mixture with a test compound, and determining the ability of the test compound to interact with a PD-L2 polypeptide, wherein determining the ability of the test compound to interact with a PD-L2 polypeptide comprises determining the ability of the test compound to preferentially bind to PD-L2 or biologically active portion thereof as compared to the known compound.

In another embodiment, the assay is a cell-free assay in which a PD-L2 polypeptide or biologically active portion thereof is contacted with a test compound and the ability of the test compound to modulate (e.g., stimulate or inhibit) the activity of the PD-L2 polypeptide or biologically active portion thereof is determined. Determining the ability of the test compound to modulate the activity of a PD-L2 polypeptide can be accomplished, for example, by determining the ability of the PD-L2 polypeptide to bind to a PD-L2 binding partner by one of the methods described above for determining direct binding. In a preferred embodiment, the binding partner is PD-1. Determining the ability of the PD-L2 polypeptide to bind to a PD-L2 binding partner can also be accomplished using a technology such as real-time Biomolecular Interaction Analysis (BIA) (Sjolander, S. and Urbaniczky, C. (1991) *Anal. Chem.* 63:2338-2345; Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a PD-L2 polypeptide can be accomplished by determining the ability of the PD-L2 polypeptide to further modulate the activity of a downstream effector of a PD-L2 binding partner (e.g., a downstream effector of PD-1). For example, the activity of the effector molecule on an appropriate target can be determined or the binding of the effector to an appropriate target can be determined as previously described.

The cell-free assays of the present invention are amenable to use of both soluble and/or membrane-bound forms of polypeptides (e.g., PD-L2 polypeptides or biologically active portions thereof, or binding partners to which PD-L2 binds, e.g., PD-1). In the case of cell-free assays in which a membrane-bound form a polypeptide is used (e.g., a cell-surface PD-L2), it may be desirable to utilize a solubilizing agent such that the membrane-bound form of the polypeptide is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either PD-L2 or its binding partner to facilitate separation of complexed from uncomplexed forms of one or both of the polypeptides, as well as to accommodate automation of the assay. In a preferred embodiment, the binding partner is PD-1. Binding of a test compound to a PD-L2 polypeptide, or interaction of a PD-L2 polypeptide with its binding partner in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the polypeptides to be bound to a matrix. For example, glutathione-S-transferase/PD-L2 fusion proteins or glutathione-S-transferase/binding partner fusion proteins can be adsorbed onto glutathione sepharose beads (Sigma Chemical, St. Louis, Mo.) or glutathione derivatized microtitre plates, which are then combined with the test compound or the test compound and either the non-adsorbed binding partner polypeptide or PD-L2 polypeptide, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of PD-L2 binding or activity determined using standard techniques.

Other techniques for immobilizing polypeptides on matrices can also be used in the screening assays of the invention. For example, either a PD-L2 polypeptide or a PD-L2 binding partner can be immobilized utilizing conjugation of biotin and streptavidin. In a preferred embodiment, the binding partner is PD-1. Biotinylated PD-L2 polypeptide or binding partners can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with PD-L2 polypeptide or binding partners but which do not interfere with binding of the PD-L2 polypeptide to its binding partner can be derivatized to the wells of the plate, and unbound binding partner or PD-L2 polypeptide is trapped in the wells by antibody conjugation. Methods for detecting such complexes, in addition to those described above for the GST-immobilized complexes, include immunodetection of complexes using antibodies reactive with the PD-L2 polypeptide or binding partner, as well as enzyme-linked assays which rely on detecting an enzymatic activity associated with the PD-L2 polypeptide or binding partner.

In an alternative embodiment, determining the ability of the test compound to modulate the activity of a PD-L2 polypeptide can be accomplished by determining the ability of the test compound to modulate the activity of a molecule that functions downstream of PD-L2, e.g., by interacting with the cytoplasmic domain of a PD-L2 binding partner, e.g., PD-1. For example, levels of second messengers, the activity of the interacting molecule on an appropriate target, or the binding of the interactor to an appropriate target can be determined as previously described.

In another embodiment, modulators of PD-L2 expression are identified in a method wherein a cell is contacted with a candidate compound and the expression of PD-L2 mRNA or polypeptide in the cell is determined. The level of expression of PD-L2 mRNA or polypeptide in the presence of the candidate compound is compared to the level of expression of PD-L2 mRNA or polypeptide in the absence of the candidate compound. The candidate compound can then be identified as a modulator of PD-L2 expression based on this comparison. For example, when expression of PD-L2 mRNA or polypeptide is greater (statistically significantly greater) in the presence of the candidate compound than in its absence, the candidate compound is identified as a stimulator of PD-L2 mRNA or polypeptide expression. Alternatively, when expression of PD-L2 mRNA or polypeptide is less (statistically significantly less) in the presence of the candidate compound than in its absence, the candidate compound is identified as an inhibitor of PD-L2 mRNA or polypeptide expression. The level of PD-L2 mRNA or polypeptide expression in the cells can be determined by methods described herein for detecting PD-L2 mRNA or polypeptide.

In yet another aspect of the invention, the PD-L2 polypeptides can be used as "bait proteins" in a two-hybrid assay or three-hybrid assay (see, e.g., U.S. Pat. No.5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other polypeptides which bind to or interact with PD-L2 ("PD-L2-binding proteins", "PD-L2 binding partners", or "PD-L2-bp") and are involved in PD-L2 activity. An example of such a binding protein is PD-1. Such PD-L2-binding proteins are also likely to be involved in the propagation of signals by the PD-L2 polypeptides or PD-L2 targets as, for example, downstream elements of a PD-L2-mediated signaling pathway. Alternatively, such PD-L2-binding polypeptides may be PD-L2 inhibitors.

The two-hybrid system is based on the modular nature of most transcription factors, which consist of separable DNA-binding and activation domains. Briefly, the assay utilizes two different DNA constructs. In one construct, the gene that codes for a PD-L2 polypeptide is fused to a gene encoding the DNA binding domain of a known transcription factor (e.g, GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming a PD-L2-dependent complex, the DNA-binding and activation domains of the transcription factor are brought into close proximity. This proximity allows transcription of a reporter gene (e.g, LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with the PD-L2 polypeptide.

In another aspect, the invention pertains to a combination of two or more of the assays described herein. For example, a modulating agent can be identified using a cell-based or a cell-free assay, and the ability of the agent to modulate the activity of a PD-L2 polypeptide can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., a PD-L2 modulating agent, an antisense PD-L2 nucleic acid molecule, a PD-L2-specific antibody, or a PD-L2 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the PD-L2 nucleotide sequences, described herein, can be used to map the location of the PD-L2 genes on a chromosome. The mapping of the PD-L2 sequences to chromosomes is an important first step in correlating these sequences with genes associated with disease.

Briefly, PD-L2 genes can be mapped to chromosomes by preparing PCR primers (preferably 15-25 bp in length) from the PD-L2 nucleotide sequences. Computer analysis of the PD-L2 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the PD-L2 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio, P. et al. (1983) *Science* 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the PD-L2 nucleotide sequences to design oligonucleotide primers, sublocalization can be achieved with panels of fragments from specific chromosomes. Other mapping strategies which can similarly be used to map a PD-L2 sequence to its chromosome include in situ hybridization (described in Fan, Y. et al. (1990) *Proc. Natl. Acad. Sci. USA* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time. For a review of this technique, see Verma et al., *Human Chromosomes: A Manual of basic Techniques* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data (such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature* 325:783-787.

Moreover, differences in the DNA sequences between individuals affected and unaffected with a disease associated with the PD-L2 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The PD-L2 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the PD-L2 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The PD-L2 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or 4 can comfortably provide positive individual identification with a panel of perhaps 10 to 1,000 primers which each yield a noncoding amplified sequence of 100 bases. If predicted coding sequences, such as those in SEQ ID NO:3 or 6 are used, a more appropriate number of primers for positive individual identification would be 500-2000.

If a panel of reagents from PD-L2 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of PD-L2 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i. e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 or 4 are particularly appropriate for this use as greater numbers of polymorphisms occur in the noncoding regions, making it easier to differentiate individuals using this technique. Examples of polynucleotide reagents include the PD-L2 nucleotide sequences or portions thereof, e.g., fragments derived from the noncoding regions of SEQ ID NO:1 or 4 having a length of at least 20 bases, preferably at least 30 bases.

The PD-L2 nucleotide sequences described herein can further be used to provide polynucleotide reagents, e.g., labeled or labelable probes which can be used in, for example, an in situ hybridization technique, to identify a specific tissue, e.g., lymphocytes. This can be very useful in cases where a forensic pathologist is presented with a tissue of unknown origin. Panels of such PD-L2 probes can be used to identify tissue by species and/or by organ type.

In a similar fashion, these reagents, e.g., PD-L2 primers or probes can be used to screen tissue culture for contamination (i.e., screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PD-L2 polypeptide and/or nucleic acid expression as well as PD-L2 activity, in the context of a biological sample (e.g., blood, serum, cells, or tissue) to thereby determine whether an individual is afflicted with a disease or disorder, or is at risk of developing a disorder, associated with aberrant or unwanted PD-L2 expression or activity. The invention also provides for prognostic (or predictive) assays for determining whether an individual is at risk of developing a disorder associated with PD-L2 polypeptide, nucleic acid expression or activity. For example, mutations in a PD-L2 gene can be assayed in a biological sample. Such assays can be used for prognostic or predictive purpose to thereby prophylactically treat an individual prior to the onset of a disorder characterized by or associated with PD-L2 polypeptide, nucleic acid expression or activity.

Another aspect of the invention pertains to monitoring the influence of agents (e.g., drugs, compounds) on the expression or activity of PD-L2 in clinical trials.

These and other agents are described in further detail in the following sections.

1. Diagnostic Assays

An exemplary method for detecting the presence or absence of PD-L2 polypeptide or nucleic acid in a biological sample involves obtaining a biological sample from a test subject and contacting the biological sample with a compound or an agent capable of detecting PD-L2 polypeptide or nucleic acid (e.g., mRNA or genomic DNA) that encodes PD-L2 polypeptide such that the presence of PD-L2 polypeptide or nucleic acid is detected in the biological sample. A preferred agent for detecting PD-L2 mRNA or genomic DNA is a labeled nucleic acid probe capable of hybridizing to PD-L2 mRNA or genomic DNA. The nucleic acid probe can be, for example, the PD-L2 nucleic acid set forth in SEQ ID NO:1, 3, 4, or 6, or a portion thereof, such as an oligonucleotide of at least 15, 30, 50, 100, 250 or 500 nucleotides in length and sufficient to specifically hybridize under stringent conditions to PD-L2 mRNA or genomic DNA. Other suitable probes for use in the diagnostic assays of the invention are described herein.

A preferred agent for detecting PD-L2 polypeptide is an antibody capable of binding to PD-L2 polypeptide, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i. e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect PD-L2 mRNA, polypeptide, or genomic DNA in a biological sample in vitro as well as in vivo. For example, in vitro techniques for detection of PD-L2 mRNA include Northern hybridizations and in situ hybridizations. In vitro techniques for detection of PD-L2 polypeptide include enzyme linked immunosorbent assays (ELISAs), Western blots, immunoprecipitations and immunofluorescence. In vitro techniques for detection of PD-L2 genomic DNA include Southern hybridizations. Furthermore, in vivo techniques for detection of PD-L2 polypeptide include introducing into a subject a labeled anti-PD-L2 antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting PD-L2 polypeptide, mRNA, or genomic DNA, such that the presence of PD-L2 polypeptide, mRNA or genomic DNA is detected in the biological sample, and comparing the presence of PD-L2 polypeptide, mRNA or genomic DNA in the control sample with the presence of PD-L2 polypeptide, mRNA or genomic DNA in the test sample.

The invention also encompasses kits for detecting the presence of PD-L2 in a biological sample. For example, the kit can comprise a labeled compound or agent capable of detecting PD-L2 polypeptide or mRNA in a biological sample; means for determining the amount of PD-L2 in the sample; and means for comparing the amount of PD-L2 in the sample with a standard. The compound or agent can be packaged in a suitable container. The kit can further comprise instructions for using the kit to detect PD-L2 polypeptide or nucleic acid.

2. Prognostic Assays

The diagnostic methods described herein can furthermore be utilized to identify subjects having or at risk of developing a disease or disorder associated with aberrant or unwanted PD-L2 expression or activity. As used herein, the term "aberrant" includes a PD-L2 expression or activity which deviates from the wild type PD-L2 expression or activity. Aberrant expression or activity includes increased or decreased expression or activity, as well as expression or activity which does not follow the wild type developmental pattern of expression or the subcellular pattern of expression. For example, aberrant PD-L2 expression or activity is intended to include the cases in which a mutation in the PD-L2 gene causes the PD-L2 gene to be under-expressed or over-expressed and situations in which such mutations result in a non-functional PD-L2 polypeptide or a polypeptide which does not function in a wild-type fashion, e.g., a polypeptide which does not interact with a PD-L2 binding partner (e.g, PD-1), or one which interacts with a non-PD-L2 binding partner. As used herein, the term "unwanted" includes an unwanted phenomenon involved in a biological response such as immune cell activation. For example, the term unwanted includes a PD-L2 expression or activity which is undesirable in a subject.

The assays described herein, such as the preceding diagnostic assays or the following assays, can be utilized to identify a subject having or at risk of developing a disorder associated with a misregulation in PD-L2 polypeptide activity or nucleic acid expression, such as an autoimmune disorder, an immunodeficiency disorder, an immune system cancer, or a tendency to have spontaneous abortions. Alternatively, the prognostic assays can be utilized to identify a subject having or at risk for developing a disorder associated with a misregulation of PD-L2 polypeptide activity or nucleic acid expression, such as an autoimmune disorder, and immunodeficiency disorder, an immune system cancer, or a tendency to have spontaneous abortions. Thus, the present invention provides a method for identifying a disease or disorder associated with aberrant or unwanted PD-L2 expression or activity in which a test sample is obtained from a subject and PD-L2 polypeptide or nucleic acid (e.g., mRNA or genomic DNA) is detected, wherein the presence of PD-L2 polypeptide or nucleic acid is diagnostic for a subject having or at risk of developing a disease or disorder associated with aberrant or unwanted PD-L2 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant or unwanted PD-L2 expression or activity. For example, such methods can be used to determine whether a subject can be effectively treated with an agent for an autoimmune disorder, immunodeficiency disorder, immune system cancer, or tendency to have spontaneous abortions. Thus, the present invention provides methods for determining whether a subject can be effectively treated with an agent for a disorder associated with aberrant or unwanted PD-L2 expression or activity in which a test sample is obtained and PD-L2 polypeptide or nucleic acid expression or activity is detected (e.g., wherein the abundance of PD-L2 polypeptide or nucleic acid expression or activity is diagnostic for a subject that can be administered the agent to treat a disorder associated with aberrant or unwanted PD-L2 expression or activity).

The methods of the invention can also be used to detect genetic alterations in a PD-L2 gene, thereby determining if a subject with the altered gene is at risk for a disorder characterized by misregulation in PD-L2 polypeptide activity or nucleic acid expression, such as an autoimmune disorder, an immunodeficiency disorder, an immune system cancer, or a tendency to have spontaneous abortions. In preferred embodiments, the methods include detecting, in a sample of cells from the subject, the presence or absence of a genetic alteration characterized by at least one alteration affecting the integrity of a gene encoding a PD-L2 polypeptide, or the mis-expression of the PD-L2 gene. For example, such genetic alterations can be detected by ascertaining the existence of at least one of 1) a deletion of one or more nucleotides from a PD-L2 gene, 2) an addition of one or more nucleotides to a PD-L2 gene, 3) a substitution of one or more nucleotides of a PD-L2 gene, 4) a chromosomal rearrangement of a PD-L2 gene, 5) an alteration in the level of a messenger RNA transcript of a PD-L2 gene, 6) aberrant modification of a PD-L2 gene, such as of the methylation pattern of the genomic DNA, 7) the presence of a non-wild type splicing pattern of a messenger RNA transcript of a PD-L2 gene, 8) a non-wild type level of a PD-L2 polypeptide, 9) allelic loss of a PD-L2 gene, and 10) inappropriate post-translational modification of a PD-L2 polypeptide. As described herein, there are a large number of assays known in the art which can be used for detecting alterations in a PD-L2 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in a PD-L2 gene (see Abravaya et al. (1995) *Nucleic Acids Res.* 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a PD-L2 gene under conditions such that hybridization and amplification of the PD-L2 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874-1878), transcriptional amplification system (Kwoh, D. Y. et al. (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PD-L2 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in PD-L2 can be identified by hybridizing a sample and control nucleic acids, e.g., DNA or RNA, to high density arrays containing hundreds or thousands of oligonucleotide probes (Cronin, M. T. et al. (1996) *Hum. Mutat.* 7:244-255; Kozal, M. J. et al. (1996) *Nat. Med.* 2:753-759). For example, genetic mutations in PD-L2 can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the PD-L2 gene and detect mutations by comparing the sequence of the sample PD-L2 with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad. Sci. USA* 74:5463. It is also contemplated that any of a variety of automated sequencing procedures can be utilized when performing the diagnostic assays (Naeve, C. W. (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the PD-L2 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type PD-L2 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397 and Saleeba et al. (1992) *Methods Enzymol.* 217: 286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in PD-L2 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a PD-L2 sequence, e.g., a wild-type PD-L2 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in PD-L2 genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) Mutat. Res. 285:125-144 and Hayashi (1992) *Genet. Anal. Tech. Appl.* 9:73-79). Single-stranded DNA fragments of sample and control PD-L2 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1 985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PD-L2 gene.

Furthermore, any cell type or tissue in which PD-L2 is expressed may be utilized in the prognostic assays described herein.

3. Monitoring of Effects During Clinical Trials

Monitoring the influence of agents (e.g., drugs) on the expression or activity of a PD-L2 polypeptide (e.g., the modulation of cell proliferation and/or migration) can be applied not only in basic drug screening, but also in clinical trials. For example, the effectiveness of an agent determined by a screening assay as described herein to increase PD-L2 gene expression, polypeptide levels, or upregulate PD-L2 activity, can be monitored in clinical trials of subjects exhibiting decreased PD-L2 gene expression, polypeptide levels, or downregulated PD-L2 activity. Alternatively, the effectiveness of an agent determined by a screening assay to decrease PD-L2 gene expression, polypeptide levels, or downregulate PD-L2 activity, can be monitored in clinical trials of subjects exhibiting increased PD-L2 gene expression, polypeptide levels, or PD-L2 activity. In such clinical trials, the expression or activity of a PD-L2 gene, and preferably, other genes that have been implicated in, for example, a PD-L2-associated disorder can be used as a "read out" or marker of the phenotype of a particular cell.

For example, and not by way of limitation, genes, including PD-L2, that are modulated in cells by treatment with an agent (e.g., compound, drug or small molecule) which modulates PD-L2 activity (e.g., identified in a screening assay as described herein) can be identified. Thus, to study the effect of agents on PD-L2-associated disorders (e.g., disorders characterized by dysregulated PD-1 activity), for example, in a clinical trial, cells can be isolated and RNA prepared and analyzed for the levels of expression of PD-L2 and other genes implicated in the PD-L2-associated disorder, respectively. The levels of gene expression (e.g., a gene expression pattern) can be quantified by Northern blot analysis or RT-PCR, as described herein, or alternatively by measuring the amount of polypeptide produced, by one of the methods as described herein, or by measuring the levels of activity of PD-L2 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression of a PD-L2 polypeptide, mRNA, or genomic DNA in the preadministration sample; (iii) obtaining one or more post-administration samples from the subject; (iv) detecting the level of expression or activity of the PD-L2 polypeptide, mRNA, or genomic DNA in the post-administration samples; (v) comparing the level of expression or activity of the PD-L2 polypeptide, mRNA, or genomic DNA in the pre-administration sample with the PD-L2 polypeptide, mRNA, or genomic DNA in the post administration sample or samples; and (vi) altering the administration of the agent to the subject accordingly. For example, increased administration of the agent may be desirable to increase the expression or activity of PD-L2 to higher levels than detected, i.e., to increase the effectiveness of the agent. Alternatively, decreased administration of the agent may be desirable to decrease expression or activity of PD-L2 to lower levels than detected, i.e., to decrease the effectiveness of the agent. According to such an embodiment, PD-L2 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder characterized by insufficient or excessive production of PD-L2 protein or production of PD-L2 protein forms which have decreased or aberrant activity compared to PD-L2 wild type protein. Moreover, the anti-PD-L2 antibodies of the invention can be used to detect and isolate PD-L2 proteins, regulate the bioavailability of PD-L2 proteins, and modulate PD-L2 activity e.g., by modulating the interaction of PD-L2 with PD-1.

1. Prophylactic Methods

In one aspect, the invention provides a method for preventing in a subject, a disease or condition associated with an aberrant or unwanted PD-L2 expression or activity, by administering to the subject a PD-L2 polypeptide or an agent which modulates PD-L2 expression or at least one PD-L2 activity. Subjects at risk for a disease or disorder which is caused or contributed to by aberrant or unwanted PD-L2 expression or activity can be identified by, for example, any or a combination of diagnostic or prognostic assays as described herein. Administration of a prophylactic agent can occur prior to the manifestation of symptoms characteristic of the PD-L2 aberrancy, such that a disease or disorder is prevented or, alternatively, delayed in its progression. Depending on the type of PD-L2 aberrancy, for example, a PD-L2 polypeptide, PD-L2 agonist or PD-L2 antagonist (e.g., an anti-PD-L2 antibody or a combination of anti-PD-L2 and anti-PD-L1 antibodies) agent can be used for treating the subject. The appropriate agent can be determined based on screening assays described herein.

2. Therapeutic Methods

Another aspect of the invention pertains to methods of modulating PD-L2 expression or activity or interaction with its natural binding partners, e.g., PD-1, for therapeutic purposes. PD-L2 has been demonstrated to inhibit the costimulation and proliferation of activated immune cells and to transmit an inhibitory signal to immune cells via PD-1. Accordingly, the activity and/or expression of PD-L2, as well as the interaction between PD-L2 and PD-1 can be modulated in order to modulate the immune response. Because PD-L2 binds to inhibitory receptors, upregulation of PD-L2 activity results in downregulation of immune responses, whereas downregulation of PD-L2 activity results in upregulation of immune responses. In a preferred embodiment, PD-L2 binds to inhibitory receptors. In a particularly preferred embodiment, PD-L2 binds to PD-1.

Modulatory methods of the invention involve contacting a cell with a PD-L2 polypeptide or agent that modulates one or more of the activities of PD-L2 polypeptide activity associated with the cell, e.g., an agent that modulates expression or activity of PD-L2 and/or modulates the interaction of PD-L2 and its natural binding partner(s). In a preferred embodiment, the binding partner is PD-1. An agent that modulates PD-L2 polypeptide activity can be an agent as described herein, such as a nucleic acid or a polypeptide, a naturally-occurring binding partner of a PD-L2 polypeptide (e.g., PD-1), a PD-L2 antibody, a combination of PD-L2 and PD-L1 antibodies, a PD-L2 agonist or antagonist, a peptidomimetic of a PD-L2 agonist or antagonist, a PD-L2 peptidomimetic, or other small molecule. Soluble forms of PD-L2 may also be used to interfere with the binding of PD-1 to any of its natural binding partner(s) or ligands.

An agent that modulates the expression of PD-L2 is, e.g., an antisense nucleic acid molecule, triplex oligonucleotide, ribozyme, or recombinant vector for expression of a PD-L2 polypeptide. For example, an oligonucleotide complementary to the area around a PD-L2 polypeptide translation initiation site can be synthesized. One or more antisense oligonucleotides can be added to cell media, typically at 200 µg/ml, or administered to a patient to prevent the synthesis of a PD-L2 polypeptide. The antisense oligonucleotide is taken up by cells and hybridizes to a PD-L2 mRNA to prevent translation. Alternatively, an oligonucleotide which binds double-stranded DNA to form a triplex construct to prevent DNA unwinding and transcription can be used. As a result of either, synthesis of PD-L2 polypeptide is blocked. When PD-L2 expression is modulated, preferably, such modulation occurs by a means other than by knocking out the PD-L2 gene.

Agents which modulate expression, by virtue of the fact that they control the amount of PD-L2 in a cell, also modulate the total amount of PD-L2 activity in a cell.

In one embodiment, the agent the modulates PD-L2 stimulates one or more PD-L2 activities. Examples of such stimulatory agents include active PD-L2 polypeptide and a nucleic acid molecule encoding PD-L2 that has been introduced into the cell. In another embodiment, the agent inhibits one or more PD-L2 activities. In a preferred embodiment, the agent inhibits or enhances the interaction of PD-L2 with its natural binding partner(s). In a particularly preferred embodiment, the binding partner is PD-1. Examples of such inhibitory agents include antisense PD-L2 nucleic acid molecules, anti-PD-L2 antibodies, PD-L2 inhibitors, and compounds identified in the subject screening assays. In a further preferred embodiment, an inhibitory agent is a combination of an anti-PD-L2 antibody and an anti-PD-L1 antibody.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of a PD-L2 polypeptide, e.g., a disorder characterized by unwanted, insufficient, or aberrant expression or activity of a PD-L2 polypeptide or nucleic acid molecule. In one embodiment, the method involves administering an agent (e.g., an agent identified by a screening assay described herein), or combination of agents that modulates (e.g., upregulates or downregulates) PD-L2 expression or activity. In another embodiment, the method involves administering a PD-L2 polypeptide or nucleic acid molecule as therapy to compensate for reduced, aberrant, or unwanted PD-L2 expression or activity.

Stimulation of PD-L2 activity is desirable in situations in which PD-L2 is abnormally downregulated and/or in which increased PD-L2 activity is likely to have a beneficial effect.

Likewise, inhibition of PD-L2 activity is desirable in situations in which PD-L2 is abnormally upregulated and/or in which decreased PD-L2 activity is likely to have a beneficial effect.

Exemplary agents for use in downmodulating PD-L2 (i.e., PD-L2 antagonists) include, e.g., antisense nucleic acid molecules, antibodies that recognize and block PD-L2, combinations of antibodies that recognize and block PD-L2 and antibodies that recognize and block PD-L1, and compounds that block the interaction of PD-L2 with its naturally occurring binding partner(s) on an immune cell (e.g., soluble, monovalent PD-L2 molecules; soluble forms of PD-L2 molecules that do not bind Fc receptors on antigen presenting cells; soluble forms of PD-L2 binding partners; and compounds identified in the subject screening assays). In a preferred embodiment, the binding partner is PD-1. Exemplary agents for use in upmodulating PD-L2 (i.e., PD-L2 agonists) include, e.g., nucleic acid molecules encoding PD-L2 polypeptides, multivalent forms of PD-L2, compounds that increase the expression of PD-L2, compounds that enhance the interaction of PD-L2 with its naturally occurring binding partners (e.g., PD-1) and cells that express PD-L2.

3. Downregulation of Immune Responses

There are numerous embodiments of the invention for upregulating the inhibitory function of a PD-L2 polypeptide to thereby downregulate immune responses. Downregulation can be in the form of inhibiting or blocking an immune response already in progress, or may involve preventing the induction of an immune response. The functions of activated immune cells can be inhibited by downregulating immune cell responses or by inducing specific anergy in immune cells, or both.

For example, in embodiments where PD-L2 binds to an inhibitory receptor, e.g., PD-1, forms of PD-L2 that bind to the inhibitory receptor, e.g., multivalent PD-L2 on a cell surface, can be used to downmodulate the immune response. Likewise, the PD-L2-PD-1 interaction can also be enhanced by the use of an additional agent, e.g., an agent that blocks the interaction of PD-L1 with PD-1, that can further downmodulate the immune response.

In one embodiment of the invention, an activating antibody used to stimulate PD-L2 activity is a bispecific antibody. For example, such an antibody can comprise a PD-L2 binding site and another binding site which targets a cell surface receptor on an immune cell, e.g., a T cell, a B cell, or a myeloid cell. In one embodiment, such an antibody, in addition to comprising a PD-L2 binding site, can further comprise a binding site which binds to a B cell antigen receptor, a T cell antigen receptor, or an Fe receptor, in order to target the molecule to a specific cell population. Selection of this second antigen for the bispecific antibody provides flexibility in selection of cell population to be targeted for inhibition.

Agents that promote a PD-L2 activity or which enhance the interaction of PD-L2 with its natural binding partners, e.g., PD-1 (e.g., PD-L2 activating antibodies or PD-L2 activating small molecules) can be identified by their ability to inhibit immune cell proliferation and/or effector function, or to induce anergy when added to an in vitro assay. For example, cells can be cultured in the presence of an agent that stimulates signal transduction via an activating receptor. A number of art-recognized readouts of cell activation can be employed to measure, e.g., cell proliferation or effector function (e.g., antibody production, cytokine production, phagocytosis) in the presence of the activating agent. The ability of a test agent to block this activation can be readily determined by measuring the ability of the agent to effect a decrease in proliferation or effector function being measured. In one embodiment, at low antigen concentrations, PD-L2-PD-1 interactions inhibit strong B7-CD28 signals. In another embodiment, at high antigen concentrations, PD-L2-PD-1 interactions reduce cytokine production but do not inhibit T cell proliferation. Accordingly, the ability of a test compound to block activation can be determined by measuring cytokine production and/or proliferation at different concentrations of antigen.

In one embodiment of the invention, tolerance is induced against specific antigens by co-administering an antigen with a PD-L2 agonist. For example, tolerance can be induced to specific polypeptides. In one embodiment, immune responses to allergens or foreign polypeptides to which an immune response is undesirable can be inhibited. For example, patients that receive Factor VIII frequently generate antibodies against this clotting factor. Co-administration of an agent that stimulates PD-L2 activity or interaction with its natural binding partner, e.g., PD-1, with recombinant factor VIII (or physically linking PD-L2 to Factor VIII, e.g., by cross-linking) can result in immune response downmodulation.

In one embodiment, a PD-L2 agonist and another agent that can block activity of costimulatory receptors on an immune cell can be used to downmodulate immune responses. Exemplary molecules include: agonists forms of other PD-1 ligands (e.g., PD-L1), soluble forms of CTLA-4, anti-B7-1 antibodies, anti-B7-2 antibodies, or combinations thereof. Alternatively, two separate peptides (for example, a PD-L2 polypeptide with blocking forms of B7-2 and/or B7-1 polypeptides), or a combination of antibodies (e.g., activating antibodies against a PD-L2 polypeptide with blocking anti-B7-2 and/or anti-B7-1 monoclonal antibodies) can be combined as a single composition or administered separately (simultaneously or sequentially) to downregulate immune cell mediated immune responses in a subject. Furthermore, a therapeutically active amount of one or more peptides having a PD-L2 polypeptide activity, along with one or more polypeptides having B7-1 and/or B7-1 activity, can be used in conjunction with other downmodulating reagents to influence immune responses. Examples of other immunomodulating reagents include antibodies that block a costimulatory signal (e.g., against CD28 or ICOS), antibodies that activate an inhibitory signal via CTLA4, and/or antibodies against other immune cell markers (e.g., against CD40, CD40 ligand, or cytokines), fusion proteins (e.g., CTLA4-Fc or PD-1-Fc), and immunosuppressive drugs (e.g., rapamycin, cyclosporine A, or FK506).

The PD-L2 polypeptides may also be useful in the construction of therapeutic agents which block immune cell function by destruction of cells. For example, portions of a PD-L2 polypeptide can be linked to a toxin to make a cytotoxic agent capable of triggering the destruction of cells to which it binds.

For making cytotoxic agents, polypeptides of the invention may be linked, or operatively attached, to toxins using techniques that are known in the art, e.g., via crosslinking or recombinant DNA techniques. The preparation of immunotoxins is, in general, well known in the art (see, e.g., U.S. Pat. No. 4,340,535 and EP 44167, both incorporated herein by reference). Numerous types of disulfide bond-containing linkers are known which can successfully be employed to conjugate the toxin moiety with a polypeptide. In one embodiment, linkers that contain a disulfide bond that is sterically "hindered" are to be preferred, due to their greater stability in vivo, thus preventing release of the toxin moiety prior to binding at the site of action.

A wide variety of toxins are known that may be conjugated to polypeptides or antibodies of the invention. Examples include: numerous useful plant-, fungus- or even bacteria-derived toxins, which, by way of example, include: various A chain toxins, particularly ricin A chain; ribosome inactivating proteins such as saporin or gelonin; alpha-sarcin; aspergillin; restrictocin; and ribonucleases such as placental ribonuclease, angiogenic, diphtheria toxin, or pseudomonas exotoxin. A preferred toxin moiety for use in connection with the invention is toxin A chain which has been treated to modify or remove carbohydrate residues, deglycosylated A chain. (U.S. Pat. No. 5,776,427).

Infusion of one or a combination of such cytotoxic agents (e.g., PD-L2 ricin (alone or in combination with PD-L1-ricin), into a patient may result in the death of immune cells, particularly in light of the fact that activated immune cells that express higher amounts of PD-L2 binding partners, e.g., PD-1. For example, because PD-1 is induced on the surface of activated lymphocytes, a PD-L2 polypeptide can be used to target the depletion of these specific cells by Fc-R dependent mechanisms or by ablation by conjugating a cytotoxic drug (e.g., ricin, saporin, or calicheamicin) to the PD-L2 polypeptide. In one another embodiment, the toxin can be conjugated to an anti-PD-L2 antibody in order to target for death PD-L2-expressing antigen-presenting cell. In a further embodiment, the PD-L2-antibody-toxin can be a bispecific antibody. Such bispecific antibodies are useful for targeting a specific cell population, e.g., using a marker found only on a certain type of cell, e.g., B lymphocytes, monocytes, dendritic cells, or Langerhans cells.

Downregulating immune responses by activating PD-L2 activity or the PD-L2-PD-1 interaction (and thus stimulating the negative signaling function of PD-1) is useful in downmodulating the immune response, e.g., in situations of tissue, skin and organ transplantation, in graft-versus-host disease (GVHD), or allergies, or in autoimmune diseases such as systemic lupus erythematosus and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of a molecule which promotes the activity of PD-L2 or the interaction of PD-L2 with its natural binding partner(s), e.g., PD-1, on immune cells (such as a soluble, multimeric form of a PD-L2 polypeptide) alone or in conjunction with another downmodulatory agent prior to or at the time of transplantation can inhibit the generation of a costimulatory signal. Moreover, promotion of PD-L2 activity or PD-L2-PD-1 interaction (and thus, a PD-1 inhibitory signal) may also be sufficient to anergize the immune cells, thereby inducing tolerance in a subject. Induction of long-term tolerance by promoting a PD-1-mediated inhibitory signal may avoid the necessity of repeated administration of these activating reagents.

To achieve sufficient immunosuppression or tolerance in a subject, it may also be desirable to block the costimulatory function of other molecules. For example, it may be desirable to block the function of B7-1 and B7-2 by administering a soluble form of a combination of peptides having an activity of each of these antigens or blocking antibodies against these antigens (separately or together in a single composition) prior to or at the time of transplantation. Alternatively, it may be desirable to promote inhibitory activity of PD-L2 and inhibit a costimulatory activity of B7-1 and/or B7-2. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune cell markers, or soluble forms of other receptor ligand pairs (e.g., agents that disrupt the interaction between CD40 and CD40 ligand (e.g., anti CD40 ligand antibodies)), antibodies against cytokines, or immunosuppressive drugs.

For example, activating PD-L2 activity or the interaction of PD-L2 with its natural binding partner(s), e.g., PD-1 (and thus the inhibitory function of said binding partner(s)), may also be useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. Administration of agents that promote activity of PD-L2 or PD-L2 interaction with its natural binding partner(s), e.g., PD-1, may induce antigen-specific tolerance of autoreactive immune cells which could lead to long-term relief from the disease. Additionally, co-administration of agents which block costimulation of immune cells by disrupting receptor-ligand interactions of B7 molecules with costimulatory receptors may be useful in inhibiting immune cell activation to prevent production of autoantibodies or cytokines which may be involved in the disease process. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840-856).

Inhibition of immune cell activation is useful therapeutically in the treatment of allergies and allergic reactions, e.g., by inhibiting IgE production. An agent that promotes PD-L2 activity or PD-L2 interaction with its natural binding partner(s), e.g., PD-1, can be administered to an allergic subject to inhibit immune cell-mediated allergic responses in the subject. Stimulation PD-L2 activity or PD-L2 interaction with its natural binding partner(s), e.g., PD-1, can be accompanied by exposure to allergen in conjunction with appropriate MHC molecules. Allergic reactions can be systemic or local in nature, depending on the route of entry of the allergen and the pattern of deposition of IgE on mast cells or basophils. Thus, immune cell-mediated allergic responses can be inhibited locally or systemically by administration of an agent that promotes PD-L2 activity or PD-L2-PD-1 interaction.

Inhibition of immune cell activation through stimulation of PD-L2 activity or PD-L2 interaction with its natural binding partner(s), e.g., PD-1, may also be important therapeutically in pathogenic infections of immune cells (e.g., by viruses or bacteria). For example, in the acquired immune deficiency syndrome (AIDS), viral replication is stimulated by immune cell activation. Stimulation of PD-L2 activity or PD-L2-PD-1 interaction may result in inhibition of viral replication and thereby ameliorate the course of AIDS.

Downregulation of an immune response via stimulation of PD-L2 activity or PD-L2 interaction with its natural binding partner(s), e.g., PD-1, may also be useful in promoting the maintenance of pregnancy. PD-L2 is normally highly expressed in placental trophoblasts, the layer of cells that forms the interface between mother and fetus and may play a role in preventing maternal rejection of the fetus. Females at risk for spontaneous abortion (e.g., those identified by screening for PD-L2 activity, as described in the "Prognostic Assays" section, those who have previously had a spontaneous abortion or those who have had difficulty conceiving) because of immunologic rejection of the embryo or fetus can be treated with agents that stimulate the activity of PD-L2 or its interaction with its natural binding partner(s), e.g., PD-1.

Downregulation of an immune response via stimulation of PD-L2 activity or PD-L2 interaction with its natural binding partner(s), e.g., PD-1, may also be useful in treating an autoimmune attack of autologous tissues. For example, PD-L2 is normally highly expressed in the heart and protects the heart from autoimmune attack. This is evidenced by the fact that the Balb/c PD-1 knockout mouse exhibits massive autoimmune attack on the heart with thrombosis. Thus, conditions that are caused or exacerbated by autoimmune attack (e.g., in this example, heart disease, myocardial infarction or atherosclerosis) may be ameliorated or improved by increasing PD-L2 activity or PD-L2 biding to its natural binding partner, e.g., PD-1. It is therefore within the scope of the invention to modulate conditions exacerbated by autoimmune attack, such as autoimmune disorders (as well as conditions such as heart disease, myocardial infarction, and atherosclerosis) by stimulating PD-L2 activity or PD-L2 interaction with PD-L1.

In an additional embodiment, in performing any of the methods described herein, it is within the scope of the invention to downregulate an immune response by stimulating the activities of both PD-L2 and PD-L1. PD-L1 is an additional PD-1 ligand which is described in the co-pending U.S. application Ser. No. 09/644,934; International Publication WO 01/14557; Dong, H. et al. (1999) *Nat. Med.* 5:1365-1369; and Freeman, G. J. et al. (2000) *J. Exp. Med.* 192:1027-1034; the contents of each of which are incorporated herein by reference. In a further additional embodiment, in performing any of the methods described herein, it is within the scope of the invention to downregulate an immune response by administering one or more additional agents. For example, the use of other agents known to downregulate the immune response can be used in conjunction with an agent that stimulates PD-L2 activity or PD-L2 interaction with its natural binding partner(s), e.g., PD-1.

4. Upregulation of Immune Responses

Inhibition of PD-L2 activity or PD-L2 interaction with its natural binding partner(s), e.g., PD-1, as a means of upregulating immune responses is also useful in therapy. Upregulation of immune responses can be in the form of enhancing an existing immune response or eliciting an initial immune response. For example, enhancing an immune response through inhibition of PD-L2 activity or PD-L2-PD-1 interaction is useful in cases of infections with microbes, e.g., bacteria, viruses, or parasites, or in cases of immunosulppression. For example, in one embodiment, an agent that inhibits PD-L2 activity or PD-L2-PD-1 interaction, e.g., a non-activating antibody (i.e., a blocking antibody) against PD-L2, a combination of non-activating antibodies against PD-L2 and PD-L1, or a soluble form of PD-L2, is therapeutically useful in situations where upregulation of antibody and cell-mediated responses, resulting in more rapid or thorough clearance of a virus, bacterium, or parasite, would be beneficial. These conditions include viral skin diseases such as Herpes or shingles, in which case such an agent can be delivered topically to the skin. In addition, systemic viral diseases such as influenza, the common cold, and encephalitis might be alleviated by the administration of such agents systemically. In certain instances, it may be desirable to further administer other agents that upregulate immune responses, for example, forms of B7 family members that transduce signals via costimulatory receptors, in order further augment the immune response.

Alternatively, immune responses can be enhanced in an infected patient by removing immune cells from the patient, contacting immune cells in vitro with an agent that inhibits the PD-L2 activity or PD-L2 interaction with its natural binding partner(s), e.g., PD-1, and reintroducing the in vitro-stimulated immune cells into the patient. In another embodiment, a method of enhancing immune responses involves isolating infected cells from a patient, e.g., virally infected cells, transfecting them with a nucleic acid molecule encoding a form of PD-L2 that cannot bind its natural binding partner(s), e.g., PD-1, such that the cells express all or a portion of the PD-L2 molecule on their surface, and reintroducing the transfected cells into the patient. The transfected cells may be capable of preventing an inhibitory signal to, and thereby activating, immune cells in vivo.

A agent that inhibits PD-L2 activity or PD-L2 interaction with its natural binding partner(s), e.g., PD-1, can be used prophylactically in vaccines against various polypeptides, e.g., polypeptides derived from pathogens. Immunity against a pathogen, e.g., a virus, can be induced by vaccinating with a viral polypeptide along with an agent that inhibits PD-L2 activity or PD-L2-PD-1 interaction, in an appropriate adjuvant. Alternately, a vector comprising genes which encode for both a pathogenic antigen and a form of PD-L2 that blocks PD-L2-PD-1 interaction can be used for vaccination. Nucleic acid vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. (1996) *J. Biotechnol.* 44:37)). Alternatively, nucleic acid vaccines can be administered by non-invasive means. For example, pure or lipid-formulated DNA can be delivered to the respiratory system or targeted elsewhere, e.g., Peyers patches by oral delivery of DNA (Schubbert (1997) *Proc. Natl. Acad. Sci. USA* 94:961). Attenuated microorganisms can be used for delivery to mucosal surfaces (Sizemore et al. (1995) *Science* 270:29).

In another embodiment, the antigen in the vaccine is a self-antigen. Such a vaccine is useful in the modulation of tolerance in an organism. Immunization with a self antigen and an agent that blocks PD-L2 activity or PD-L2 interaction with its natural binding partner (e.g., PD-1) can break tolerance (i.e., interfere with tolerance of a self antigen). Such a vaccine may also include adjuvants such as alum or cytokines (e.g., GM-CSF, IL-12, B7-1, or B7-2).

In one embodiment, an agent which inhibits PD-L2 activity or PD-L2 interaction with its natural binding partner(s), e.g., PD-1, can be administered with class I MHC polypeptides by, for example, a cell transfected to coexpress a PD-L2 polypeptide or blocking antibody and MHC class I $\alpha$ chain polypeptide and $\beta_2$ microglobulin to result in activation of T cells and provide immunity from infection. For example, viral pathogens for which vaccines are useful include: hepatitis B, hepatitis C, Epstein-Barr virus, cytomegalovirus, HIV-1, HIV-2, tuberculosis, malaria and schistosomiasis.

In another application, inhibition of PD-L2 activity or PD-L2 interaction with its natural binding partner(s), e.g., PD-1, can be useful in the treatment of tumor immunity. Tumor cells (e.g., sarcoma, melanoma, lymphoma, leukemia, neuroblastoma, or carcinoma) can be transfected with a nucleic acid molecule that inhibits PD-L2 activity or PD-L2-PD-1 interaction. These molecules can be, e.g., nucleic acid molecules which are antisense to PD-L2, or can encode non-activating anti-PD-L2 antibodies or combinations of anti-PD-L2 and anti-PD-1 antibodies. These molecules can also be the variable region of an anti-PD-L2 antibody and/or an anti-PD-L1 antibody. If desired, the tumor cells can also be transfected with other polypeptides which activate costimulation (e.g., B7-1 or B7-2). The transfected tumor cells are returned to the patient, which results in inhibition (e.g., local inhibition) of PD-L2 activity or PD-L2-PD-1 interaction. Alternatively, gene therapy techniques can be used to target a tumor cell for transfection in vivo.

Stimulation of an immune response to tumor cells can also be achieved by inhibiting PD-L2 activity or PD-L2 interaction with its natural binding partner(s), e.g., PD-1, by treating a patient with an agent that inhibits PD-L2 activity or PD-L2 interaction with its natural binding partner(s), e.g., PD-1. Preferred examples of such agents include, e.g., antisense nucleic acid molecules, antibodies that recognize and block PD-L2, a combination of antibodies that recognize and block PD-L2 and antibodies that recognize and block PD-L1, and compounds that block the interaction of PD-L2 with its naturally occurring binding partner(s) on an immune cell (e.g., soluble, monovalent PD-L2 molecules; soluble forms of PD-L2 molecules that do not bind to Fc receptors on antigen presenting cells; soluble forms of PD-L2 binding partner(s); and compounds identified in the subject screening assays). In a most preferred embodiment, the PD-L2 binding partner is PD-1.

In addition, tumor cells which lack MHC class I or MHC class II molecules, or which fail to express sufficient amounts of MHC class I or MHC class II molecules, can be transfected with nucleic acid encoding all or a portion of (e.g., a cytoplasmic-domain truncated portion) of an MHC class I α chain polypeptide and $\beta_2$ microglobulin polypeptide or an MHC class II α chain polypeptide and an MHC class II β chain polypeptide to thereby express MHC class I or MHC class II polypeptides on the cell surface. Expression of the appropriate class I or class II MHC in conjunction with an PD-L2 inhibiting polypeptide or antisense nucleic acid induces a T cell mediated immune response against the transfected tumor cell. Optionally, a gene encoding an antisense construct which blocks expression of an MHC class II-associated polypeptide, such as the invariant chain, can also be cotransfected with a DNA encoding a PD-L2 inhibiting polypeptide or antisense nucleic acid to promote presentation of tumor associated antigens and induce tumor specific immunity. Expression of B7-1 by B7-negative murine tumor cells has been shown to induce T cell mediated specific immunity accompanied by tumor rejection and prolonged protection to tumor challenge in mice (Chen, L. et al. (1992) *Cell* 71:1093-1102; Townsend, S. E. and Allison, J. P. (1993) *Science* 259: 368-370; Baskar, S. et al. (1993) *Proc. Natl. Acad. Sci.* 90:5687-5690). Thus, the induction of an immune cell-mediated immune response in a human subject can be sufficient to overcome tumor-specific tolerance in the subject.

In another embodiment, the immune response can be stimulated by the inhibition of PD-L2 activity or PD-L2 interaction with its natural binding partner(s), e.g., PD-1, such that preexisting tolerance is overcome. For example, immune responses against antigens to which a subject cannot mount a significant immune response, e.g., tumor-specific antigens, can be induced by administering an agent that inhibits the activity of PD-L2 activity or the ability of PD-L2 to bind to its natural binding partner, e.g., PD-1. PD-1 antagonists can be used as adjuvants to boost responses to foreign antigens in the process of active immunization.

In one embodiment, immune cells are obtained from a subject and cultured ex vivo in the presence of an agent that inhibits PD-L2 activity or PD-L2 interaction with its natural binding partner(s), e.g., PD-1, to expand the population of immune cells. In a further embodiment the immune cells are then administered to a subject. Immune cells can be stimulated to proliferate in vitro by, for example, providing the immune cells with a primary activation signal and a costimulatory signal, as is known in the art. Various forms of PD-L2 polypeptides or agents that inhibit PD-L2 activity or PD-L2-PD-1 and/or PD-L1/PD-1 interaction can also be used to costimulate proliferation of immune cells. In one embodiment, immune cells are cultured ex vivo according to the methods described in PCT Application No. WO 94/29436. The costimulatory molecule can be soluble, attached to a cell membrane or attached to a solid surface, such as a bead.

In an additional embodiment, in performing any of the methods described herein, it is within the scope of the invention to upregulate an immune response by administering one or more additional agents. For example, the use of other agents known to stimulate the immune response, such as cytokines, adjuvants, or stimulatory forms of costimulatory molecules or their ligands can be used in conjunction with an agent that inhibits PD-L2 activity or PD-L2 interaction with its natural binding partner(s), e.g., PD-1. For example, an agent that inhibits PD-L1 (e.g., a blocking antibody against PD-L1) can be used in conjunction with an agent that inhibits PD-L2 (e.g., a blocking antibody against PD-L2). PD-L1 is an additional PD-1 ligand which is described in the co-pending U.S. application Ser. No. 09/644,934; International Publication WO 01/14557; Dong, H. et al. (1999) *Nat. Med.* 5:1365-1369; and Freeman, G. J. et al. (2000) *J. Exp. Med.* 192:1027-1034; the contents of each of which are incorporated herein by reference.

E. Identification of Cytokines Modulated by Modulation of PD-L2 Activity or PD-L2-PD-1 Interaction The PD-L2 molecules described herein can be used to identify cytokines which are produced by or whose production is enhanced or inhibited in immune cells in response to modulation of PD-L2 activity or PD-L2 interaction with its natural binding partner(s), e.g., PD-1. Immune cells expressing PD-1 can be suboptimally stimulated in vitro with a primary activation signal, for example, T cells can be stimulated with phorbol ester, anti-CD3 antibody or preferably, antigen, in association with an MHC class II molecule, and given a costimulatory signal, e.g., by a stimulatory form of B7 family antigen, for instance by a cell transfected with nucleic acid encoding a B7 polypeptide and expressing the peptide on its surface, or by a soluble, stimulatory form of the peptide. The cells can then be contacted with cells expressing PD-L2 and/or treated with agents which inhibit PD-L2-PD-1 interaction (e.g., antibodies against PD-L2, or combinations of antibodies against PD-L2 and antibodies against PD-L1). Known cytokines released into the media can be identified by ELISA or by the ability of an antibody which blocks the cytokine to inhibit immune cell proliferation or proliferation of other cell types that are induced by the cytokine. For example, an IL-4 ELISA kit is available from Genzyme (Cambridge, Mass.), as is an IL-7 blocking antibody. Blocking antibodies against IL-9 and IL-12 are available from Genetics Institute (Cambridge, Mass.). The effect of stimulating or blocking PD-L2 activity or the interaction of PD-L2 and PD-1 on the cytokine profile can then be determined.

An in vitro immune cell costimulation assay as described above can also be used in a method for identifying novel cytokines which can be modulated by modulation of PD-L2 activity or PD-L2-PD-1 interaction. For example, where stimulation of the CD28/CTLA4 pathway seems to enhance IL-2 secretion, stimulation of the ICOS pathway seems to enhance IL-10 secretion (Hutloff al. (1999) *Nature* 397: 263). If a particular activity induced upon costimulation, e.g., immune cell proliferation, cannot be inhibited by addition of blocking antibodies to known cytokines, the activity may result from the action of an unknown cytokine. Following costimulation, this cytokine can be purified from the media by conventional methods and its activity measured by its ability to induce immune cell proliferation.

To identify cytokines which may play a role the induction of tolerance, an in vitro T cell costimulation assay as described above can be used. In this case, T cells would be given the primary activation signal and contacted with a selected cytokine, but would not be given the costimulatory signal. After washing and resting the immune cells, the cells would be rechallenged with both a primary activation signal and a costimulatory signal. If the immune cells do not respond (e.g., proliferate or produce cytokines) they have become tolerized and the cytokine has not prevented the induction of tolerance. However, if the immune cells respond, induction of tolerance has been prevented by the cytokine. Those cytokines which are capable of preventing the induction of tolerance can be targeted for blockage in vivo in conjunction with reagents which block B lymphocyte antigens as a more efficient means to induce tolerance in transplant recipients or subjects with autoimmune diseases. For example, one could administer a cytokine blocking antibody to a subject along with an agent that promotes PD-L2 activity or PD-L2-PD-1 interaction.

This invention is further illustrated by the following examples, which should not be construed as limiting. The contents of all references, patents, and published patent applications cited throughout this application, as well as the Figures and Sequence Listing, are incorporated herein by reference.

EXAMPLES

The following Materials and Methods were used in Examples 1-9.

Materials and Methods

Mice

Hoffman-La Roche, Nutley, N.J., provided mice expressing a TCR transgene (DO11.10) which is specific for OVA peptide (323-339) in association with $IA^d$. Balb/c mice were obtained from Taconic Farms (Germantown, N.Y.). All mice were used between the ages of 6-12 weeks. The mice were cared for in accordance with institutional guidelines.

Molecular Cloning

A BLAST search of the non-redundant database of the National Center for Biotechnology Information (NCBI) using the human PD-L1 protein sequence as a query identified GenBank Accession No. AF 142780 (also referred to herein as mouse PD-L2) as having 38% amino acid identity with PD-L1. PD-L1 is a PD-1 ligand described in the co-pending U.S. application Ser. No. 09/644,934; International Publication WO 01/14557; Dong, H. et al. (1999) *Nat. Med.* 5:1365-1369; and Freeman, G. J. et al. (2000) *J. Exp. Med.* 192:1027-1034; the contents of each of which are incorporated herein by reference. The AF142780 coding region was amplified by PCR using as primers 5'-dGTCGACCACCAT-GCTGCTCCTGCTGCCGATA-3' (SEQ ID NO: 7) and 5'-dGTCGACTCACTAGATCCTCTTTCTCTG-GATTATCAC-3' (SEQ ID NO: 8) and cloned into pEF6 (Invitrogen, Carlsbad, Calif.). A search of the NCBI EST database identified 2 human fetal heart ESTs (GenBank Accession Nos. AA247117 and AA247128) with homology to murine PD-L2. A 101 bp region was amplified by PCR using as primers 5'-dGTACATAATAGAGCATGGCAGCA-3' (SEQ ID NO: 9) and 5'-dCCACCTTTTGCAAACTG-GCTGT-3' (SEQ ID NO: 10). The PCR product was biotin-labeled and used to isolate a full-length cDNA by Cloncapture (Clontech, Palo Alto, Calif.) from a human placenta cDNA library in the pAXEF vector (Freeman, G. J. et al. (2000) *J. Exp. Med.* 192:1027-1034). The full-length human PD-L2 cDNA sequence has been deposited with GenBank (accession number to be assigned).

Fusion Proteins and Cell Transfections

The Ig fusion proteins consist of the complete extracellular region of a receptor linked to the hinge-CH2-CH3 domains of murine Ig γ2a (with four point mutations blocking Fc receptor and complement binding) to give Ig(γ2a) fusions (Duncan, A. R. et al. (1988) *Nature* 332:563-564; Morgan, A. et al. (1995) *Immunology* 86:319-324). Control.Ig consists of the Oncostatin-M leader sequence linked to murine Ig γ2a. These recombinant proteins were produced in stably transfected CHO cell lines and purified from conditioned media using protein A-Sepharose. The murine PD-L2 cDNA in pEF6 was linearized with ScaI and co-electroporated into CHO.I-$A^d$, or CHO.I-$A^d$.mB7-2 cells with a plasmid construct containing a puromycin resistance gene under the control of a phosphoglycerate kinase gene promoter. The human PD-L2 cDNA in pAXEF was linearized with ApaLI and co-electroporated into CHO.K1 cells with a puromycin-resistance gene under the control of a phosphoglycerate kinase gene promoter. Transfectants were selected in 10 µg/ml puromycin, stained with hPDI.Ig, sorted, and cloned by limiting dilution.

Northern Blot Analysis

Mouse and human multiple tissue northern blots (Clontech, Palo Alto, Calif.) were probed with $^{32}$P-dCTP radiolabeled cDNA probes in QuikHyb (Stratagene, La Jolla, Calif.) according to manufacturer's instructions. The human PD-L2 probe consisted of a 1.2 kb XbaI fragment spanning the coding region and 3' UTR sequence. The mouse PD-L2 probe consisted of a 444 kb KpnI/EcoRV cDNA fragment spanning the coding region. Actin probes were supplied by Clontech. Blots were washed twice at room temperature in 2×SSC, 0.1% SDS, followed by 0.1×SSC, 0.1% SDS at 65° C., and examined by autoradiography.

Flow Cytometry

For detection of PD-L2, $5\times10^4$ transfected CHO cells were incubated with 5 µg/ml of human PD-1Ig (hPD-1.Ig) (Genetics Institute, Cambridge, Mass.) and developed with goat anti-mouse IgG2a-phycoerythrin (PE) (Southern Biotechnology Associates Inc, Birmingham, Ala.). In addition, cells were stained separately with 5 µg/ml anti-$IA^d$-PE or B7.2-PE (Pharmingen, San Diego, Calif.).

$CD4^+$ T cells were incubated with biotinylated anti-PD-1 (or biotinylated anti-CD28 (Pharmingen) or biotinylated anti-CD25 (Pharmingen) and developed with streptavidin-PE (Pharmingen). All isotype controls were obtained from Pharmingen. Following each step, cells were washed three times with PBS/1% BSA/0.02% sodium azide. After the final incubation, cells were fixed with 1% paraformaldehyde. Ten thousand events were analyzed on a FACSCalibar (Becton Dickinson, Mountain View, Calif.). All isotype controls were all obtained from Pharmingen.

Activation of T Cells

To generate activated antigen-specific T cells, splenocytes were prepared from DO11.10 mice and treated with Tris-$NH_4Cl$ to deplete erythrocytes. Cells were cultured with 1

µg/ml of OVA peptide for 72 hours (Analytical Biotechnology Services, Boston, Mass.) in RPMI 1640 (Life Technologies, Grand Island, N.Y.) supplemented with 10% FCS (Sigma, St Louis, Mo.), 2 mM L-glutamine, 100 U/ml penicillin, 100 mg/ml streptomycin, 250 ng/ml amphotericin B, 10 mM Hepes, 50 pM 2-ME (all from Life Technologies) and 15 mg/ml of gentamicin (BioWhittaker, Walkersville, Md.). $CD4^+$ T cells were purified by positive selection using magnetic-activated cell sorting separation columns (Miltenyi Biotec, Auburn, Calif.) with resulting purity of >98%. Cells were rested overnight before re-stimulation.

Bead Stimulation of T Cells

Anti-CD3 Ab (2C11; Pharmingen, La Jolla, Calif.), mPD-L2.Ig, and control.Ig were covalently attached to polyurethane-coated tosyl-activated Dynabeads (Dynal, Lake Success, N.Y.). Beads were prepared with a constant sub-optimal anti-CD3 Ab concentration (60% of the total bound protein) and mPD-L2.Ig or control Ig (40% of total bound protein). Beads have a protein binding capacity of 5 µg/$10^7$ beads. T cells were purified from Balb/c lymph nodes by negative selection using cell enrichment columns (R & D Systems, Minneapolis, Minn.). 0.5-1×$10^5$ T cells were cultured per well in 96 well plates with a 2:1 ratio of the indicated coated tosyl beads:cells. Proliferation was measured by [$^3$H]-thymidine incorporation for the last 10 hours of a 72 hr culture.

CHO Cell Stimulation of T Cells

Proliferation of transfected CHO cells was inhibited by incubation with 50 µg/ml of mitomycin C (Bristol Laboratories, Princeton, N.J.) or 16 hours at 37° C. At the end of the incubation period, the cells were harvested with 10 mM EDTA in PBS, washed twice and left on ice for 1 hour. The cells were subsequently washed three times and resuspended in culture medium. $10^5$ previously activated $CD4^+$ T cells were cultured with varying concentrations of OVA peptide and $10^4$ mitomycin C-treated CHO transfectants in 96 well plates. To assay proliferation, cultures were incubated for 48 hrs and pulsed with 1 µCi/well of [$^3$H] thymidine (New England Nuclear, Boston, Mass.) for the last 6 hours of the incubation period.

Cytokine ELISA

Aliquots of supernatants were harvested at various times after initiation of cultures. IL-2, IL-4, IFN-γ and IL-10 levels were analyzed using mAbs and recombinant cytokine standards from Pharmingen. Detection limits were as follows: IL-2: 20 pg/ml; IL-4: 40 pg/ml; IFN-γ: 100 pg/ml;and IL-10: 200 pg/ml.

RNAase Protection Assay (RPA)

$CD4^+$ T cells were restimulated with various CHO cell transfectants and 0.01 µg/ml OVA peptide. After 48 hours, cells were harvested and mRNA was isolated using TRIzol® reagent (Life Technologies, Grand Island, N.Y.). 5 µg mRNA was analyzed for cytokine levels by RNAase protection assay using RiboQuant multiprobe kit mCK1 according to manufacturer's instructions (Pharmingen, San Diego, Calif.).

Cell Cycle Analysis $CD4^+$ T cells were restimulated with 0.01 µg/ml peptide and CHO transfectants as described above. After 36 hours of culture, cells were recovered and stained with anti-CD4-FITC. Cells were washed in PBS, fixed in 70% ethanol for 1 hour on ice and then resuspended in PBS containing 10 µg/ml RNase (Sigma, St. Louis, Mo.) and 50 µg/ml propidium iodide (Sigma). Analysis was performed within an hour of staining using a FACSCalibar.

Example 1

Identification and Characterization of Human and Mouse PD-L2 cDNA

In this example, the identification and characterization of the genes encoding human PD-L2 and mouse PD-L2 is described.

Isolation of the Human PD-L2 cDNA

The invention is based, at least in part, on the discovery of human genes encoding novel polypeptides, referred to herein as human PD-L2. The human PD-L2 cDNA was isolated from a human placental cDNA library using as a probe the human EST AA247117. The entire sequence of human PD-L2 was determined and found to contain an open reading frame termed human "PD-L2"

The nucleotide sequence encoding the human PD-L2 is shown in FIG. 1 and is set forth as SEQ ID NO: 1. The polypeptide encoded by this nucleic acid comprises about 273 amino acids and has the amino acid sequence shown in FIG. 1 and set forth as SEQ ID NO: 2. The coding region (open reading frame) of SEQ ID NO: 1 is set forth as SEQ ID NO: 3.

The nucleotide sequence encoding the mouse PD-L2 is shown in FIG. 2 and is set forth as SEQ ID NO: 4. The polypeptide encoded by this nucleic acid comprises about 247 amino acids and has the amino acid sequence shown in FIG. 2 and set forth as SEQ ID NO: 5. The coding region (open reading frame) of SEQ ID NO: 4 is set forth as SEQ ID NO: 6.

Analysis of the Human and Mouse PD-L2 Molecules

Each of the amino acid sequences of human and mouse PD-L2 was analyzed by comparison to other B7 family members for the presence of a signal peptide. These analyses resulted in the identification of a signal peptide domain in the amino acid sequence of the native human PD-L2 (SEQ ID NO: 2) at about residues 1-19 (FIG. 3). These analyses further identified a signal peptide domain in the amino acid sequence of the native mouse PD-L2 (SEQ ID NO: 5) at about residues 1-19 (FIG. 3).

Each of the amino acid sequences of human and mouse PD-L2 was also analyzed by comparison to other B7 family members for the presence of an IgV domain. These analyses resulted in the identification of an IgV domain in the amino acid sequence of the native human PD-L2 (SEQ ID NO: 2) at about residues 20-120 (FIG. 3), and at about residues 1-101 in the predicted mature polypeptide. These analyses further identified an IgV domain in the amino acid sequence of the native mouse PD-L2 (SEQ ID NO: 5) at about residues 20-120 (FIG. 3), and at about residues 1-101 in the predicted mature polypeptide.

Additionally, each of the amino acid sequences of human and mouse PD-L2 was analyzed by comparison to other B7 family members for the presence of an IgC domain. These analyses resulted in the identification of an IgC domain in the amino acid sequence of the native human PD-L2 (SEQ ID NO: 2) at about residues 121-219 (FIG. 3), and at about residues 102-200 in the predicted mature polypeptide. These analyses further identified an IgC domain in the amino acid sequence of the native mouse PD-L2 (SEQ ID NO: 5) at about residues 121-219 (FIG. 3), and at about residues 102-200 in the predicted mature polypeptide.

Each of the amino acid sequences of human and mouse PD-L2 was further analyzed by comparison to other B7 family members for the presence of an extracellular domain. These analyses resulted in the identification of an extracellular domain in the amino acid sequence of the native human PD-L2 (SEQ ID NO: 2) at about residues 1-219 (FIG. 1), and at about residues 1-200 in the predicted mature polypeptide. These analyses further identified an extracellular domain in the amino acid sequence of the native mouse PD-L2 (SEQ ID NO: 5) at about residues 1-219 (FIG. 2), and at about residues 1-200 in the predicted mature polypeptide.

Each of the amino acid sequences of human and mouse PD-L2 was also analyzed by comparison to other B7 family members for the presence of a transmembrane domain. These analyses resulted in the identification of a transmembrane domain in the amino acid sequence of the native human PD-L2 (SEQ ID NO: 2) at about residues 220-243 (FIG. 3), and at about residues 201-224 in the predicted mature polypeptide. These analyses further identified a transmembrane domain in the amino acid sequence of the native mouse PD-L2 (SEQ ID NO: 5) at about residues 220-242 (FIG. 3), and at about residues 201-223 in the predicted mature polypeptide.

Each of the amino acid sequences of human and mouse PD-L2 was further analyzed by comparison to other B7 family members for the presence of a cytoplasmic domain. These analyses resulted in the identification of a cytoplasmic domain in the amino acid sequence of the native human PD-L2 (SEQ ID NO: 2) at about residues 244-273 (FIG. 3), and at about residues 225-254 in the predicted mature polypeptide. These analyses further identified a cytoplasmic domain in the amino acid sequence of the native mouse PD-L2 (SEQ ID NO: 5) at about residues 243-247 (FIG. 3), and at about residues 224-228 in the predicted mature polypeptide.

The mouse PD-L2 protein has 38% amino acid identity with mouse PD-L1 (see FIG. 6). Mouse and human PD-L2 have 70% amino acid identity (FIG. 6), which is higher than the 46-50% identity between human and murine B7-1 or B7-2.

Example 2

Expression of Recombianant PD-L2 Polypeptide in Bacterial Cells

In this example, human PD-L2 is expressed as a recombinant glutathione-S-transferase (GST) fusion polypeptide in *E. coli* and the fusion polypeptide is isolated and characterized. Specifically, PD-L2 is fused to GST and this fusion polypeptide is expressed in *E. coli*, e.g., strain PEB199. Expression of the GST-PD-L2 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Binding of PD-L2 TO PD-1

COS cells were transfected with an expression plasmid containing AF142780, the mouse PD-L2 cDNA, or a control mouse PD-1 ligand. After 72 hours, the transfected COS cells were detached by incubation in PBS containing 0.5 mM EDTA for 30 min. at 37° C.

The ability of COS cells expressing PD-L2 to bind to various Ig fusion proteins was tested. FACS analysis of binding of IgG2a (control Ig), ICOS-IgG, and PD-1-Ig by PD-L2-tranfected COS cells showed that neither IgG2a or ICOS-IgG was bound by PD-L2 or the control PD-1 ligand. PD-1-Ig, however, was shown to bind to PD-L2 and to the control PD-1 ligand (FIG. 4).

Experiments using the human PD-L2 cDNA yielded results similar to those obtained using the mouse PD-L2 cDNA.

Figure 7A:
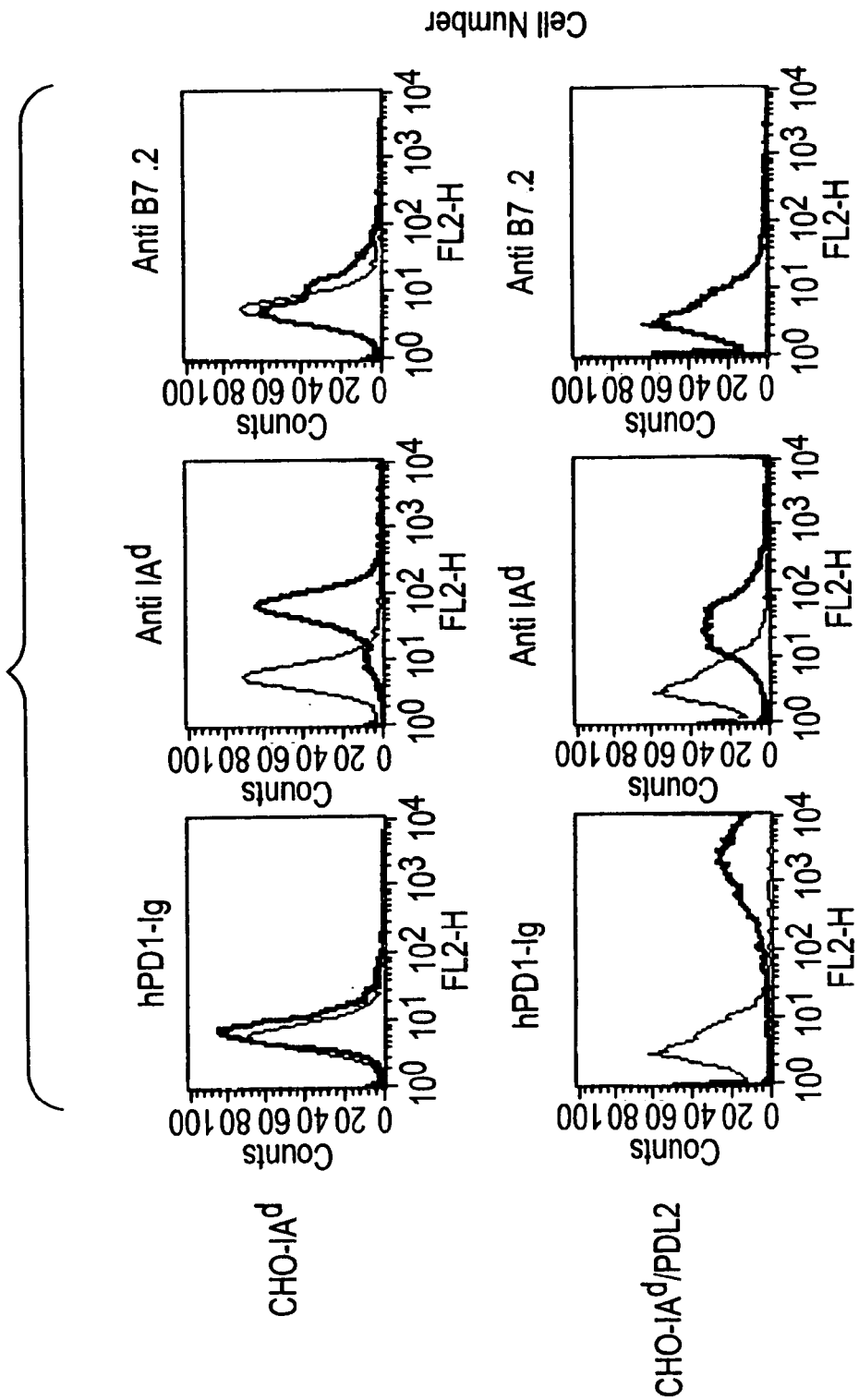
FIGS. 7A and B depict the binding of PD-1 to PD-L2. A and B are both graphical representations of the data obtained from experiments where CHO cells expressing I-$A^d$ alone (A) or I-$A^d$ and B7-2 (B) were either not transfected or stably transfected with mouse PD-L2. Cells were stained with hPD-1-Ig and stained with PE-goat anti-mouse IgG2a (thick line). CHO cells were stained separately using PE-anti-I-$A^d$ or PE-anti-B7-2 (thick line). The thin lines indicate staining with isotype control monoclonal antibody. Ten-thousand events were analyzed.
Figure 7B:
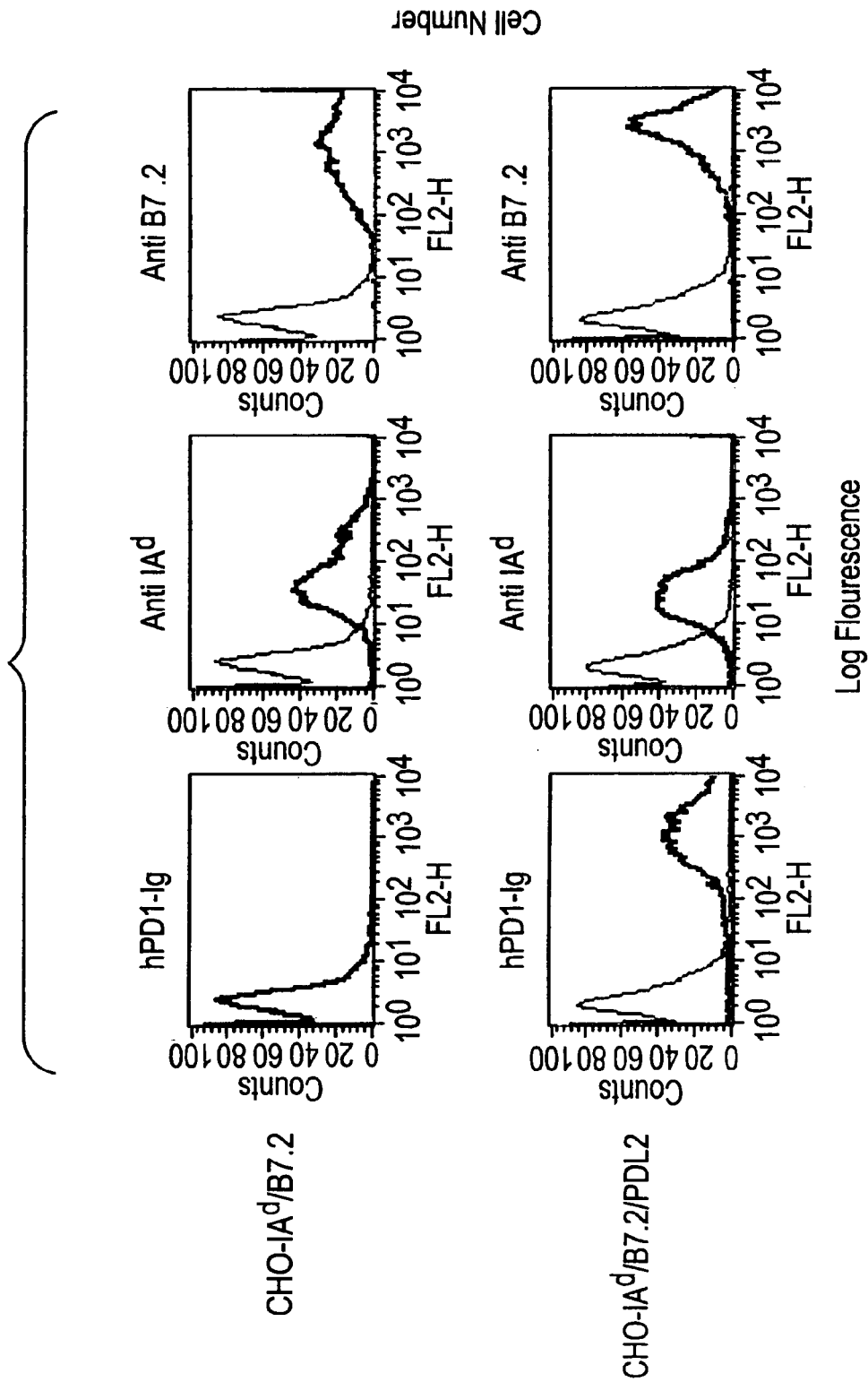

Experiments were also preformed using CHO cells. Flow cytometry studies indicate that hPD-1-Ig recognizes CHO cells stably transfected with PD-L2 (FIGS. 7A and 7B). This staining was specific, since there was no binding to control transfectants (CHO-IA$^d$, CHO-IA$^d$/B7.2). CHO cells transfected with PD-L2 showed no staining with CTLA4-Ig, CD28-Ig or ICOS-Ig. An alternatively spliced variant of murine PD-L2, wherein the IgV exon is deleted, was also isolated. This variant did not bind PD-1-Ig, indicating that the IgV domain is necessary for PD-L2 binding to PD-1.

Example 4

Generation of Fully Human Antibodies to PD L2

In this example, fully human antibodies against PD-L2 are made in mice that are transgenic for human immunoglobulin framework genes. Transgenic mice are made using standard methods, e.g., according to Hogan et al., *Manipulating the Mouse Embryo: A Laboratory Manual*, Cold Spring Harbor Laboratory, which is incorporated herein by reference, or are purchased commercially. Embryonic stem cells are manipulated according to published procedures (*Teratocarcinomas and embryonic stem cells: a practical approach*, Robertson, E. J. ed., IRL Press, Washington, D.C., 1987; Zijlstra et al. (1989) *Nature* 342:435-438; and Schwartzberg et al. (1989) *Science* 246:799-803, each of which is incorporated herein by reference). DNA cloning procedures are carried out according to Sambrook, J. et al. in *Molecular Cloning: A Laboratory Manual*, 2d ed., 1989, Cold Spring Harbor Laboratory Press, Cold Spring Harbor, N.Y., which is incorporated herein by reference. Oligonucleotides are synthesized, e.g., on an Applied Bio Systems oligonucleotide synthesizer according to specifications provided by the manufacturer or are purchased commercially.

Transgenic mice are immunized using a purified or recombinant PD-L2 or a fusion protein comprising at least an immunogenic portion of the extracellular domain of PD-L2. Approximately four hundred pg of PD-L2 in 100 µL of phosphate buffered saline (PBS) is injected intraperitoneally into each mouse. Serum samples are collected approximately six days later by retro-orbital sinus bleeding.

Antibody reactivity and specificity for PD-L2 are assessed using an indirect enzyme-linked immunosorbent assay (ELISA). Several immunoglobulin superfamily molecules are tested as controls (e.g., CTLA4 and CD28) to analyze the antibody specificity of the antibody for PD-L2. Antibodies having human framework regions which bind to PD-L2 are detected by enzyme conjugates specific for human IgM and human IgG sub-classes with no cross reactivity to mouse immunoglobulin. Briefly, PVC microtiter plates are coated with PD-L2 by coating wells overnight at 37° C. with 5µg/mL PD-L2 in PBS. Serum samples are diluted in PBS, 5% serum, 0.5% Tween-20 and are incubated in the wells for 1 hour at room temperature, followed by anti-human IgG Fc and IgG F(ab')-horseradish peroxidase or anti-human IgM Fc-horseradish peroxidase in the same diluent. After 1hour at room temperature enzyme activity is assessed by addition of ABTS substrate (Sigma, St. Louis, Mo.) and read after 30 minutes at 415-490 nm. In pre-immunization serum samples from the same mice, titers of human antibodies to the same target antigens are also tested.

Spleen cells isolated from mice having appropriate antibody titers are harvested. The spleen cells are fused to appropriate fusion partners (e.g., myeloma cells) to make hybridomas. Hybridomas and antibodies are manipulated according to *Antibodies: A Laboratory Manual,* Ed Harlow and David Lane, Cold Spring Harbor Laboratory (1988), which is incorporated herein by reference.

Example 5

Generation of Antibodies to PD-L2

Anti-human PD-L2 Antibodies

Anti-PD-L2 antibodies can also be prepared by cDNA immunization of mice. For production of anti-human PD-L2 antibodies, female Balb/c mice (Harlan Sprague-Dawley, Inc., Indianapolis, Ind.) were prepared for cDNA immunization by injecting 50 µl of 10 mM cardiotoxin (Sigma Chemical Company, St. Louis, Mo.) in 0.9% saline into the tibialis anterior muscle of each hind limb. Five days later, 50 µl of 1 mg/ml purified hPD-L2 cDNA in the pAXEF mammalian expression vector in 0.9% saline was injected into each regenerating anterior tibialis anterior muscle of each mouse. The cDNA immunization was repeated twice at 2 week intervals. The mice were then rested for four weeks, followed by three boosts of 100 µg cDNA per mouse, spread 3-4 weeks apart. Five days before fusion, a mouse selected for fusion was boosted with cDNA intramuscularly. Spleen cells were fused with SP2/0 myeloma cells, cloned, and the hybridomas screened by ELISA for reactivity with hPD-L2-mIgG2a fusion protein, followed by cell surface staining of hPD-L2 transfected 300.19 and COS cells and for lack of reactivity with untransfected cells and hPD-L1 transfected cells.

Nine mouse anti-human PD-L2 monoclonal antibodies (mAbs) were isolated. In order to determine the capacity of these antibodies to block the PD-1/PD-L2 interaction, the anti-PD-L2 mAbs were preincubated with PD-L2 transfected cells. Inhibition of the interaction was measured as the capacity of the mAb to reduce the binding of biotinylated PD-1-Ig to PD-L2 transfected cells. The best mAbs were antibodies 24F.10C12 (also referred to herein as 10C12) and 24F7G12 (also referred to herein as 7G12). The results are as follows:

| mAb | mean fluorescence intensity of biotinylated hPD-1-Ig bound to 300-hPD-L2 cells |
|---|---|
| 7G12 | 0.110 |
| 10C12 | 0.109 |
| positive control | 2.57 |

Anti-mouse PD-L2 Antibodies

For production of anti-mouse PD-L2 antibodies, female Lewis strain rats (Harlan Sprague-Dawley, Inc., Indianapolis, Ind.) were prepared for cDNA immunization by injecting 100 µl of 10 mM cardiotoxin (Sigma Chemical Company, St. Louis, Mo.) in 0.9% saline into the tibialis anterior muscle of each hind limb. Five days later, 100 µl of 1 mg/ml purified murine PD-L2 cDNA in the pEF6 mammalian expression vector in 0.9% saline was injected into each regenerating anterior tibialis anterior muscle of each rat. The cDNA immunization was repeated three times at 2-3 week intervals. The rats were then immunized with 1-5×10$^7$ CHO-mPD-L2 transfectants four times at 2-5 week intervals. Five days before fusion, a rat selected for fusion was immunized with both cDNA (200 µg) and cells (5×10$^7$). Spleen cells were fused with SP2/0 myeloma cells, cloned, and the hybridomas screened by cell surface staining of mPD-L2 transfected 300.19 and COS cells and for lack of reactivity with untransfected cells and mPD-L1 transfected cells. Monoclonal antibodies were produced that specifically recognize mPD-L2.

Example 6

Expression of PD-L2

To analyze the expression PD-L2, mRNA expression was analyzed by Northern blot hybridization in a variety of tissues and in activated antigen presenting cells. Human and murine PD-L2 mRNAs are expressed highly in normal placenta, and are expressed at low levels in normal spleen, lymph nodes, and thymus. PD-L2 is also expressed in human heart, but is expressed at a low level in mouse heart. Other tissues in which PD-L2 is expressed are human pancreas, lung and liver. PD-L2 mRNA was not detected in unstimulated human monocytes but was upregulated by IFN-γ stimulation. The induction of PD-L2 was slightly delayed in kinetics as compared to the upregulation of PD-L1 (Freeman, G. J. et al. (2000) *J. Exp. Med.* 192:1027-1034). Northern blot analysis of murine tumor cell lines revealed PD-L2 mRNA expression in lines of lymphoid origin such as PU5-1.8 (myeloid lymphoma), RAW 264.7 (macrophage lymphoma), R1.1 (T lymphoma), L1210 (lymphocytic leukemia), P388D1 (monocyte/macrophage lymphoma), and P815 (mastocytoma). PD-L2 was expressed poorly or not at all in fibroblast cell lines (M-MSV Balb/3T3, K-Balb, LM) and the P19 teratocarcinoma cell line. PD-L2 is also expressed in hepatoma (Hepa 1-6) and neuroblastoma (NB41A3) cell lines.

Example 7

PD-L2-PD-1 Interaction Inhibits TCR Mediated Responses

Figure 8:
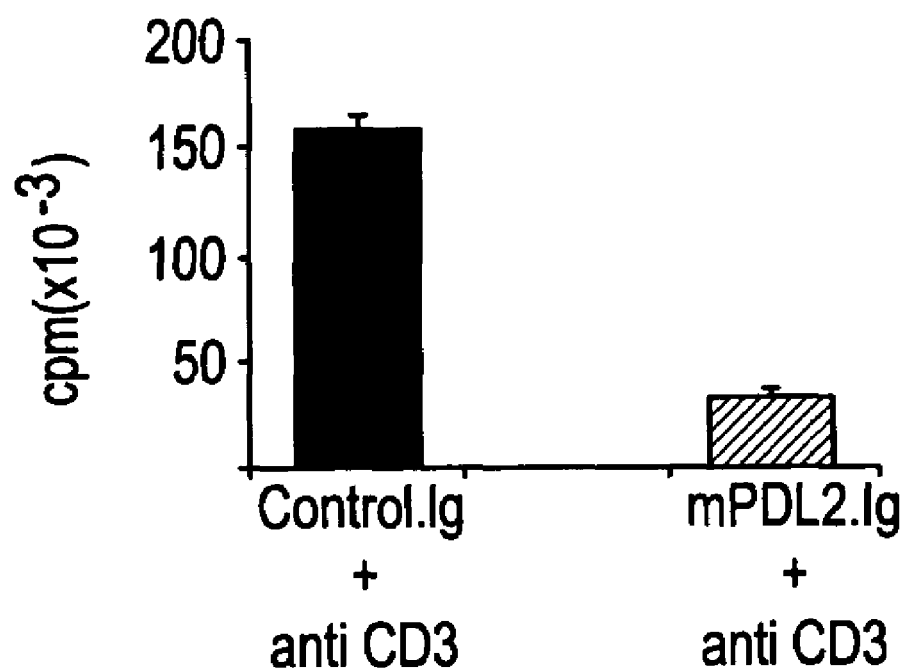
FIG. 8 depicts inhibition of TCR-mediated responses by PD-L2-PD-1 interaction. Purified T cells from BALB/c lymph nodes were stimulated at a 2:1 bead:cell ratio with tosyl beads coated with anti-CD3+control Ig or anti-CD3+ mPD-L2-Ig. Proliferation was measured after 72 hours. These data are representative of more than eight independent experiments.

To investigate the role of the PD-L2-PD-1 pathway in T cell activation, a Dynal bead-based T cell activation system was used. Purified T cells from Balb/c lymph nodes were activated with beads coated with anti-CD3 plus control.Ig or mPD-L2.Ig. Proliferation was measured by $^3$H-thymidine incorporation. T cells activated with anti-CD3 plus mPD-L2.Ig coated beads showed a marked decrease in proliferation relative to anti-CD3 plus control.Ig activated cells (FIG. 8). Thus, engagement of PD-1 on T cells by PD-L2 leads to inhibition of T cell proliferation.

Figure 9:
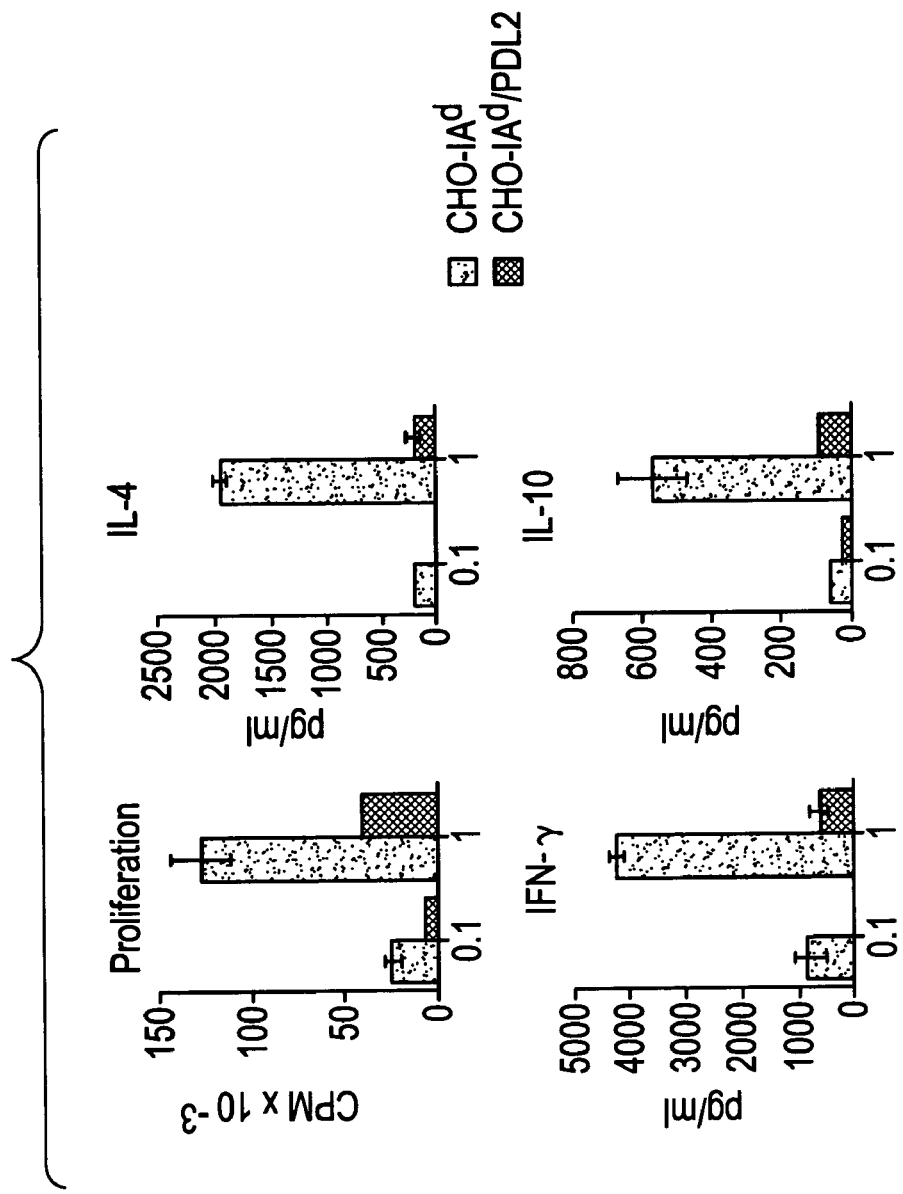
FIG. 9 depicts inhibition of TCR-mediated responses by PD-L2-PD-1 interaction. Splenocytes from DO11.10 transgenic mice were activated with OVA peptide (1 μg/ml). $CD4^+$ T cells were isolated and rested overnight. Previously activated T cells ($10^5$) were restimulated with peptide (1 or 0.1 μg/ml) presented by CHO-I-$A^d$ or CHO-I-$A^d$-PD-L2 for 48 hours. [$^3$H]thymidine incorporation was measured in triplicate. Aliquots of supernatents were collected at 36 hours after initiation of cultures and cytokines measured by ELISA. These data are representative of four independent experiments.

In order to study antigen specific signals, CHO cells co-expressing PD-L2 and I-A$^d$ and CHO cells expressing similar levels of I-A$^d$ alone (FIG. 7) were compared in their ability to activate DO11.10 CD4$^+$ T cells. Because PD-1 is upregulated after activation, pre-activated DO11.10 T cells were used to enable maximal PD-L2 interaction. Pre-activated CD4$^+$ T cells were incubated with a range of concentrations of OVA (323-339) peptide and mitomycin-C treated CHO transfectants. As seen in FIG. 9, pre-activated DO11.10 CD4$^+$ T cells gave a moderate proliferative response to OVA peptide presented by CHO.I-A$^d$. In contrast, this response was significantly reduced in the presence of PD-L2. Interleukin (IL)-4, IFN-γ and IL-10 productions were also markedly reduced (FIG. 9). IL-2 was not detected under these conditions of activation. These data show that PD-1-PD-L2 interactions can inhibit TCR mediated proliferation and cytokine production. The inhibitory effects of the PD-1-PD-L2 pathway and the expression of PD-L2 in non-lymphoid organs points to a role in controlling autoimmune reactions.

Example 8

PD-L2 Can Inhibit TCR-CD28 Signals

Figure 10:
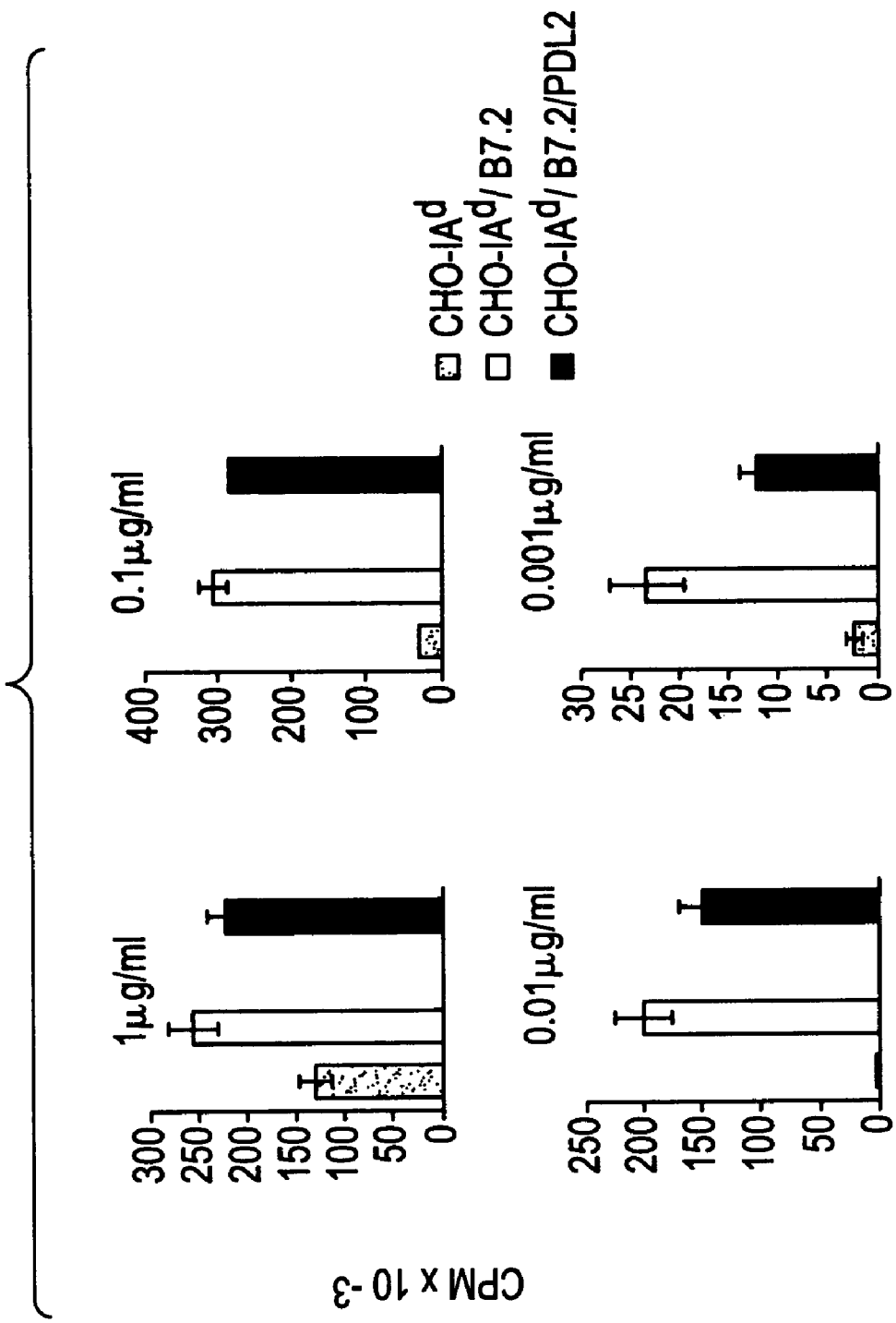
FIG. 10 depicts inhibition of TCR and CD28 mediated responses by PD-L2-PD-1 interaction. Splenocytes from DO 11.10 transgenic mice were activated with OVA peptide (1 μg/ml) for 4 days. $CD4^+$ T cells were isolated and rested overnight. Previously activated T cells ($10^5$) were restimulated, with varying peptide concentrations (0.001 μg/ml, 0.01 μg/ml, 0.1 μg/ml and 1 μ/ml), by the indicated CHO transfectants for 48 hours. [$^3$H]thymidine incorporation was measured in triplicate. These data are representative of six independent experiments.
Figure 11:
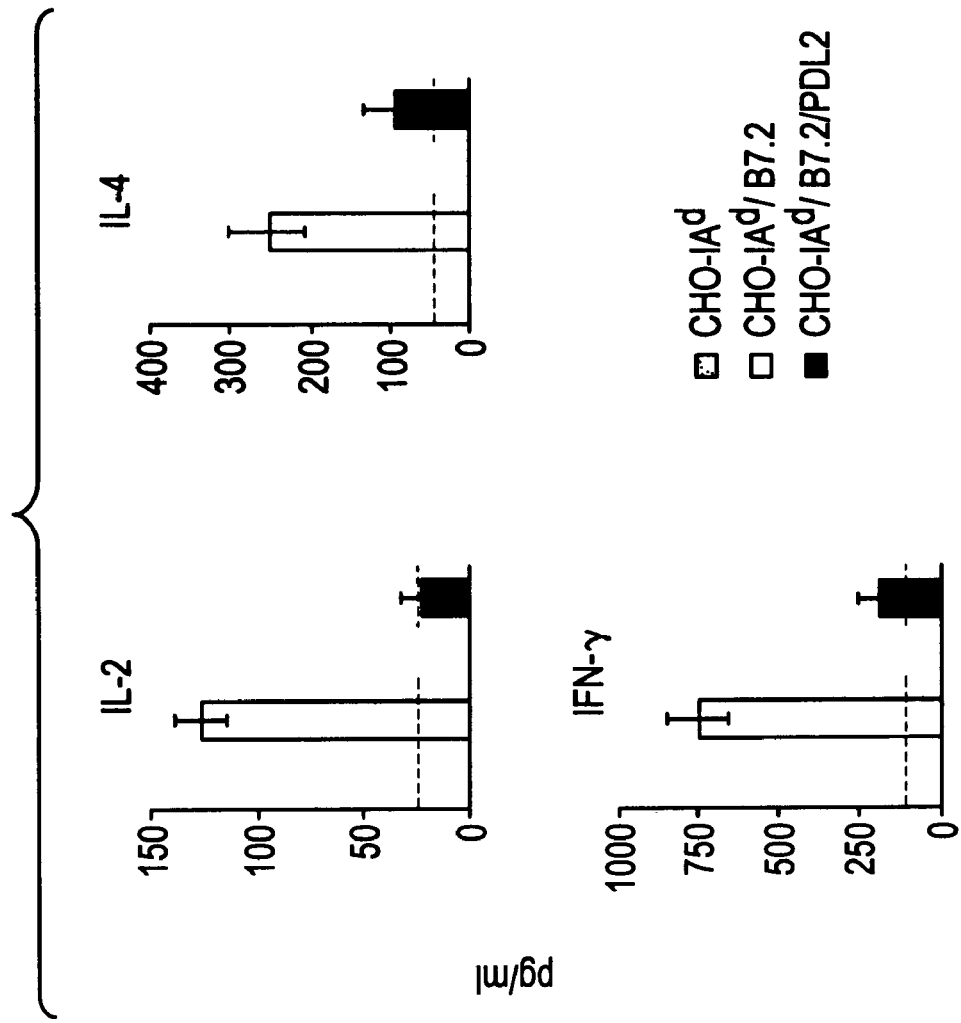
FIG. 11 depicts inhibition of TCR and CD28 mediated responses by PD-L2-PD-1 interaction. Previously activated T cells ($10^5$) were cultured with 0.01 μg/ml OVA peptide presented by the indicated CHO transfectants. Aliquots of supernatents were collected at 36 hours after initiation of cultures and cytokines measured by ELISA. The broken line indicates the sensitivity of the ELISA.
Figure 12:
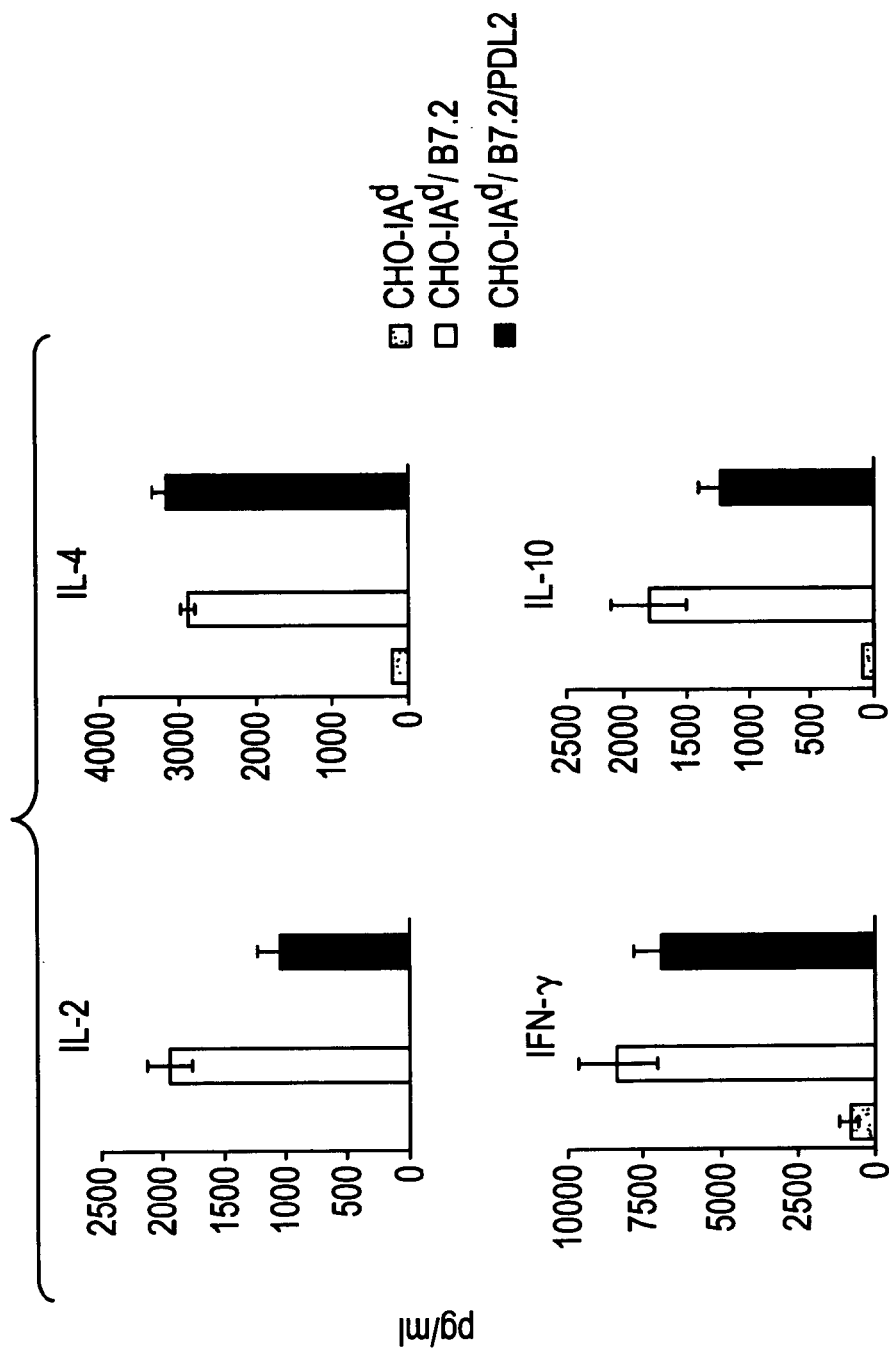
FIG. 12 depicts inhibition of TCR and CD28 mediated responses by PD-L2-PD-1 interaction. Previously activated T cells ($10^5$) were cultured with 0.1 μg/ml OVA peptide presented by the indicated CHO transfectants. Aliquots of supernatents were collected at 36 hours after initiation of cultures and cytokines measured by ELISA. The broken line indicates the sensitivity of the ELISA.

Since optimal T cell clonal expansion requires both TCR and CD28 signals, the interplay between the TCR plus CD28 and PD-L2-PD-1 signals was examined. To address this issue, the following CHO transfectants were used: CHO.I-$A^d$.B7-2 and CHO.I-$A^d$.B7-2.PD-L2. The ability of these CHO transfectants to stimulate previously activated DO11.10 CD4$^+$ T cells with OVA peptide was compared. The expression of I-$A^d$ and B7-2 was similarly high on these CHO transfectants (FIG. 7). The level of PD-L2 expression, as measured by PD-1.Ig binding, was high. As expected, introduction of B7-2 led to an increase in proliferative responses by T cells at all antigen concentrations, with the most marked stimulation at low antigen concentrations (FIG. 10). Co-expression of PD-L2 on CHO transfectants inhibited TCR and B7-2 mediated proliferative responses at low peptide concentrations (0.01 μg/ml and 0.001 μg/ml) (FIG. 10). At 0.01 μg/ml peptide concentration, PD-L2 significantly inhibited TCR-B7-2 mediated cytokine production, consistent with the inhibition of proliferation (FIG. 11). At 0.1 μg/ml peptide concentration, where there was only a weak inhibition of proliferation, cytokine production was inhibited when DO11.10 CD4$^+$ T cells were cultured with peptide and CHO.I-$A^d$.B7-2.PD-L2 transfectants (FIG. 12). Therefore, PD-1 engagement by PD-L2 can downregulate TCR-CD28 mediated stimulation of cytokine production.

To determine whether the diminished cytokine production was due to reduced mRNA levels, cytokine mRNA levels were measured by RNAase protection assay. Interleukin-4, IL-10, IL-13, IL-2, IL-6 and IFN-γ mRNAs were readily detected in previously activated DO11.10 CD4$^+$ T cells after stimulation with 0.01 μg/ml OVA peptide presented by CHO.I-$A^d$.B7-2. However, the introduction of PD-L2 into the CHO.I-$A^d$.B7-2 transfectants significantly reduced mRNA levels for both $T_h1$ and $T_h2$ cytokines. There was minimal expression of cytokine mRNAs when previously activated T cells were incubated alone or with peptide presented by CHO.I-$A^d$. These results further demonstrate the capacity of the PD-L2-PD-1 pathways to antagonize a B7-CD28 signal when antigenic stimulation is weak or limiting.

To assess whether the ability of the PD-L2-PD-1 pathway to inhibit at low antigen concentrations was related to variations in levels of CD28 and PD-1 expression at different antigen concentrations, surface expression of PD-1 and CD28 was examined. Table 1 shows the mean fluorescence intensity of PD-1, CD28 and CD25 on DO11.10 CD4$^+$ T cells following different activation conditions.

TABLE 1

MFI of CD28, PD-1, and CD25 on freshly isolated and previously activated DO11.10 CD4$^+$ T cells and during restimulation with CHO.I-$A^d$.B7-2

| | Antibody | MFI | | | | | | | |
|---|---|---|---|---|---|---|---|---|---|
| Freshly isolated CD4$^+$DO11.10 T cells | CD28 | 33 | | | | | | | |
| | PD-1 | 14 | | | | | | | |
| | CD25 | 27 | | | | | | | |
| | Isotype | 16 | | | | | | | |
| | | Expt. 1 | | | | Expt. 2 | | | |
| Previously activated CD4$^+$ DO11.10 T cells Restimulated | CD28 | 50 | | | | 117 | | | |
| | PD-1 | 51 | | | | 51 | | | |
| | CD25 | 373 | | | | 2705 | | | |
| | Isotype | 12 | | | | 17 | | | |
| | | Peptide Conc. (μg/ml) | | | | | | | |
| CD4$^+$DO11.10 T cells | | 0.001 | 0.01 | 0.1 | 1.0 | 0.001 | 0.01 | 0.1 | 1.0 |
| | | Expt. 1 | | | | Expt. 2 | | | |
| | CD28 | 77 | 106 | 123 | 165 | 77 | 121 | 338 | 516 |
| | PD-1 | 78 | 56 | 41 | 39 | 117 | 92 | 84 | 55 |
| | CD25 | 334 | 417 | 560 | 1154 | 2507 | 2602 | 2971 | 7021 |
| | Isotype | 11 | 14 | | | | | | |

CD4$^+$ T cells were incubated with biotinylated anti-PD-1, biotinylated anti-CD28, biotinylated anti-CD25, or biotinylated isotype control and developed with streptavidin-PE.

Freshly isolated DO11.10 CD4$^+$ T cells expressed CD28, but neither PD-1 nor CD25. T cells stimulated with 1 μg/ml of peptide presented by splenic APCs upregulated CD28 modestly and strongly upregulated PD-1 and CD25. After restimulation of previously activated DO11.10 CD4$^+$ T cells with various concentrations of peptide presented by CHO.I-$A^d$.B7.2, CD28 and CD25 expression increased on CD4$^+$ T cells with higher peptide concentration. In contrast, PD-1 expression was highest on T cells activated at low peptide concentration and decreased at higher peptide concentrations. The higher expression of PD-1 at lower antigen doses further suggests a mechanism whereby the PD-L2-PD-1 pathway can attenuate weak antigen responses.

Example 9

Mechanism of Action of the PD-1-PD-L2 Pathway

Figure 13:
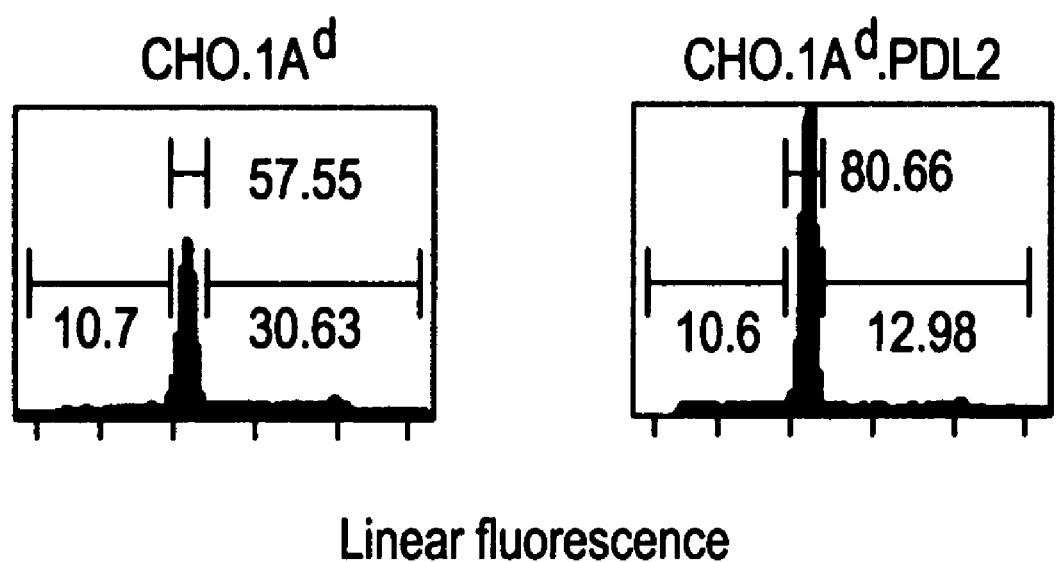
FIG. 13 depicts cell cycle arrest and apoptosis as a result of the engagement of the PD-L2-PD-1 pathway. Previously activated T cells were restimulated with OVA peptide (1 μg/ml) and the indicated CHO transfectants. Cells were collected after 36 hours of culture, stained with anti-CD4 and fixed in 70% ethanol. Cells were resuspended in propidium iodide solution. FACS profiles are propidium iodide staining of the CD4+ population. Subdiploid, diploid, and supradiploid populations are indicated. Ten-thousand events were collected and analyzed at a constant flow rate. These data are representative of three independent experiments.

Cross-linking of CTLA-4 has been shown to inhibit cell cycle progression in naive T cells (Krummel, M. F. and Allison, J. P. (1996) *J. Exp. Med.* 183:2533-2540; Walunas, T. L. et al. (1996) *J. Exp. Med.* 183:2541-2550). As PD-1 was isolated from murine cell lines undergoing apoptosis, a possible mechanism of action of the PD-1:PD-L2 pathway might be to increase programmed cell death (e.g., activation-induced cell death or AICD). To address this issue, DO11.10 CD4$^+$ T cells were restimulated with 0.01 μg/ml peptide and various CHO transfectants, and cell cycle progression was analyzed. After 48 hours, cells were recovered, stained with CD4-FITC, permeabilized, and incubated with propidium iodide to analyze the $G_0/G_1$, $S/G_2$ and sub-diploid populations. CD4$^+$ T cells restimulated with peptide presented by CHO-IA$^d$ or CHO-IA$^d$/PD-L2 both have a large proportion of cells in the sub-diploid population, indicative of apoptosis (FIG. 13). These results were confirmed by annexin staining. In cultures where CD4$^+$ T cells were stimulated by peptide presented by CHO-IA$^d$ (1 µg/ml), there were increased number of cells in the S/G$_2$ phase, indicating that the cells were in cycle. The introduction of PD-L2 into I-A$^d$ transfectants led to an increased number of cells in the G$_0$/G$_1$ phase, suggesting cell cycle arrest.

Figure 14:
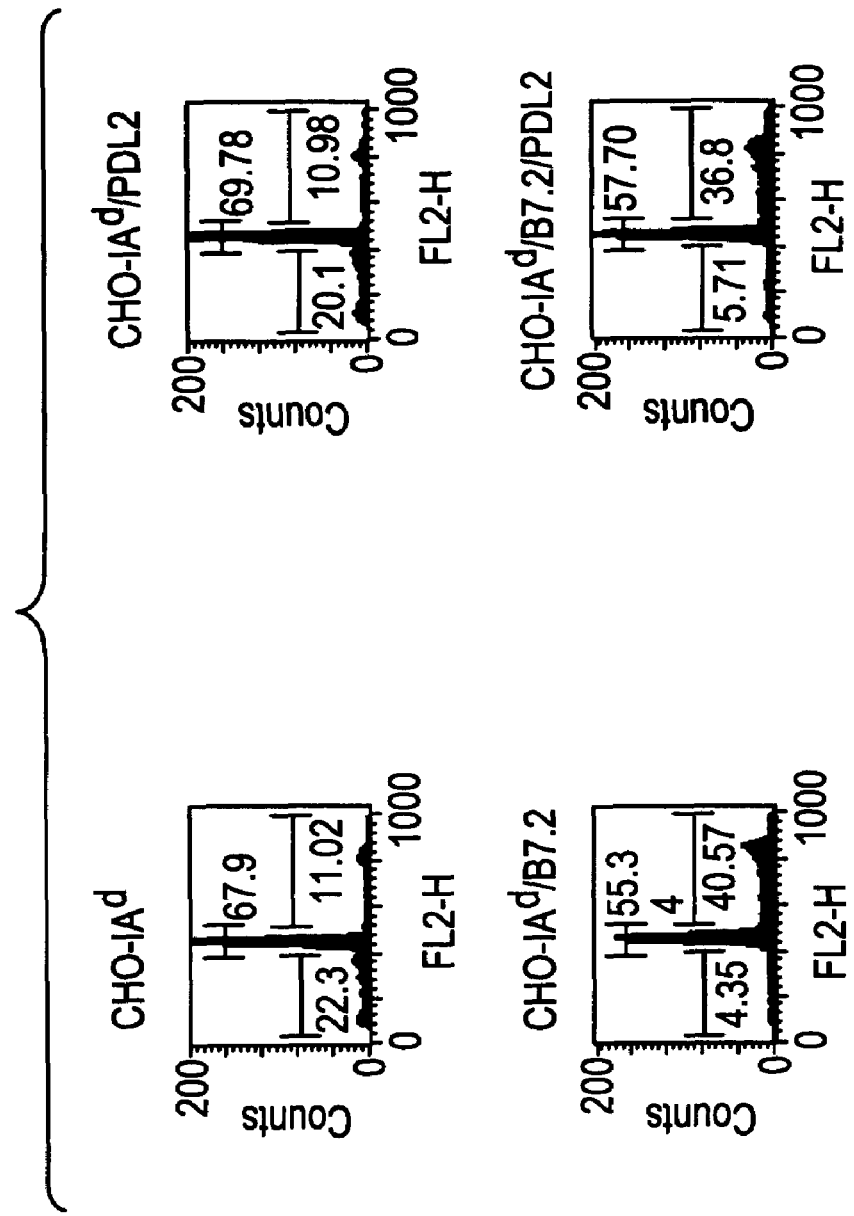
FIG. 14 depicts cell cycle arrest and apoptosis as a result of the engagement of the PD-L2-PD-1 pathway. Previously activated T cells were restimulated with OVA peptide (0.01 μg/ml) and the indicated CHO transfectants. Cells were collected after 36 hours of culture, stained with anti-CD4 and fixed in 70% ethanol. Cells were resuspended in propidium iodide solution. FACS profiles are propidium iodide staining of the CD4+ population. Subdiploid, diploid, and supradiploid populations are indicated. Ten-thousand events were collected and analyzed at a constant flow rate. These data are representative of three independent experiments.

Cell cycle progression in the presence of B7-2 and PD-L2 signals was then compared. CD4$^+$ T cells stimulated by 0.01 µg/ml peptide presented by CHO.I-A$^d$.B7-2 showed an increased number of cells in the S/G$_2$ phase and a decreased number in the sub-diploid population indicating cells were in cycle and rescued from apoptosis by B7-CD28 costimulation (FIG. 14). As seen with the CHO.I-A$^d$ transfectants at higher peptide concentrations, introduction of PD-L2 into B7-2 transfectants led to an increased number of cells in the G$_0$/G$_1$ phase and a corresponding decrease in those in S phase. There was no difference in the proportion of apoptotic cells between B7-2 and B7-2.PD-L2 stimulated T cells, indicating that PD-1 crosslinking did not lead to an increase in cell death.

Example 10

Stimulation of T Cell Activation by Inhibtion of PD-1D-Ligand Interaction

As shown above, signaling via PD-1 is dominated by strong TCR/CD28 costimulatory signals; the PD-1 signaling pathway inhibits moderate TCR/CD28 costimulatory signals, with cytokine production being reduced first without a decrease in T cell proliferation. As the TCR/CD28 costimulatory signals weaken, the PD-1 pathway dominates, with a great reduction in cytokine production accompanied by a reduction in proliferation. Accordingly, in order to determine whether inhibition of the PD-1 pathway via inhibition of the interaction with PD-L1 or PD-L2 would enhance T cell activation, mixed lymphocyte reactions (MLRs) were performed using weakly functioning antigen presenting cells (APCs) (i.e., antigen presenting cells with weak TCR/CD28 costimulation).

Mature dendritic cells are potent APCs. However, treatment with IL-10 reduces their potency. Previous reports indicate that IL-10 greatly reduces dendritic cell APC potency, and this has been attributed to a reduction in the expression of MHC, B7-1, and B7-2. However, experiments herein indicate that the reduction is modest; moreover, IL-10 treated dendritic cells express PD-L1 and PD-L2.

Immature myeloid dendritic cells were isolated by culturing human peripheral blood monocytes in IL-4 and GM-CSF. Exposure of immature dendritic cells to an inflammatory cocktail of IL-1β, TNF-α, IL-6, and PGE$_2$ elicits the development of mature dendritic cells that function as APCs. However, the addition of IL-10 to the inflammatory cytokines given during the maturation phase results in APCs that function only ⅙ to ⅓ as well.

Figure 15:
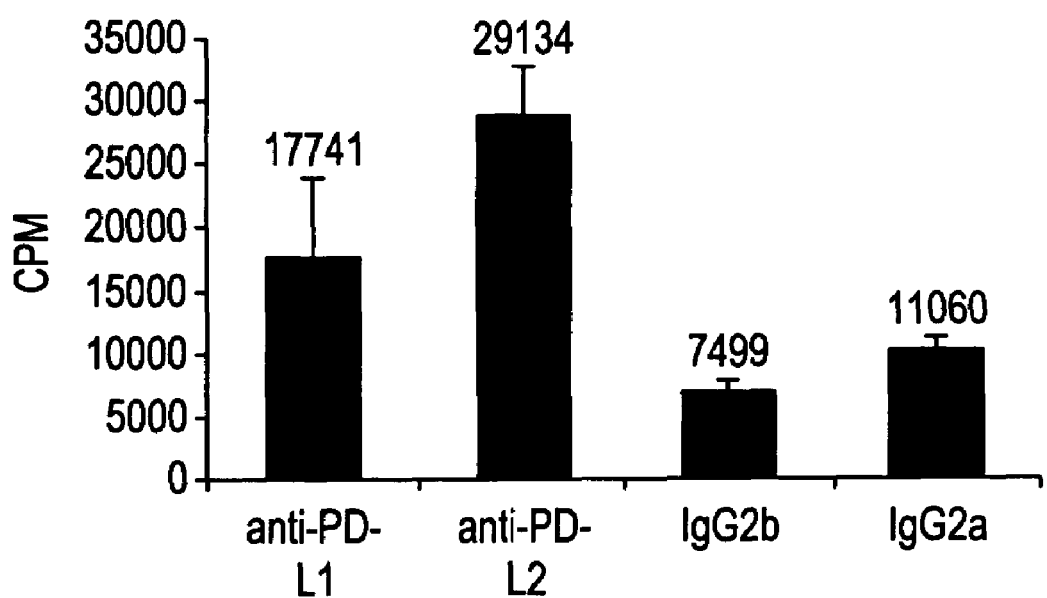
FIG. 15 depicts the enhancement of T cell proliferation in the presence of anti-PD-L1 or anti PD-L2 antibodies. Allogeneic CD4+ T cells were stimulated in a mixed lymphocyte reaction by IL-10 treated dendritic cells.

T cell activation assays (MLRs) were performed as described generally above, using IL-10 treated dendritic cells as APCs, in the presence of antibodies to PD-L1 and/or PD-L2, or control antibodies. The addition of anti-PD-L1 or PD-L2 mAb to cultures of IL-10 treated dendritic cells plus allogeneic T cells resulted in a 3-fold increase in T cell proliferation, as compared to control IgG treated cultures (FIG. 15). A combination of anti-PD-L1 and anti-PD-L2 antibodies resulted in an increase in stimulation greater than that seen with either antibody alone (FIG. 16). This stimulation is consistent with the result expected from blockade of the immunoinhibitory signal mediated by PD-L1 and/or PD-L2 binding to PD-1.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method of identifying a compound which upmodulates T cell activation at both a low and high antigen concentration comprising:

a) contacting a T cell expressing PD-1 with a test compound at a low concentration of antigen to which the T cell is specific in the presence of a costimulatory signal and a PD-1 ligand having the amino acid sequence of SEQ ID NO:2 or SEQ ID NO:5, wherein the low concentration of antigen is minimally sufficient to induce T cell proliferation to levels above background in the absence of a PD-1-mediated signal and wherein the low concentration of antigen is 0.001 μg/ml–0.01 μg/ml;

b) determining the ability of the test compound to upmodulate T cell proliferation or cytokine production at the low antigen concentration;

c) contacting a T cell expressing PD-1 with the test compound at a high antigen concentration in the presence of a costimulatory signal and a PD-1 ligand having the amino acid sequence selected from the group consisting of SEQ ID NO:2 or SEQ ID NO:5, wherein the high antigen concentration is 0.1 μg/ml–1.0 μg/ml; and d) determining the ability of the test compound to upmodulate T cell proliferation or cytokine production at the high antigen concentration, wherein the ability of the compound to upmodulate T cell proliferation or cytokine production at both the low and high antigen concentration identifies the compound as one that upmodulates T cell activation at a both a low and high antigen concentration.

2. A method of identifying a compound which upmodulates T cell activation at both a low and high antigen concentration comprising:

a) contacting a T cell expressing PD-1 with a test compound at a low concentration of antigen to which the T cell is specific in the presence of a costimulatory signal and a PD-1 ligand having the amino acid sequence of SEQ ID NO:2 or SEQ ID NO:5, wherein the low concentration of antigen is minimally sufficient to induce T cell proliferation to levels above background in the absence of a PD-1-mediated signal and wherein the low concentration of antigen is 0.001 μg/ml–0.01 μg/ml;

b) determining the ability of the test compound to upmodulate T cell proliferation or cytokine production at the low antigen concentration;

c) contacting a T cell expressing PD-1 with the test compound at a high antigen concentration in the presence of a costimulatory signal and a PD-1 ligand having the amino acid sequence selected from the group consisting of SEQ ID NO:2 or SEQ ID NO:5, wherein the high antigen concentration is 0.01 μg/ml–1.0 μg/ml and wherein the high antigen concentration is always greater than the low antigen concentration; and d) determining the ability of the test compound to upmodulate T cell proliferation or cytokine production at the high antigen concentration, wherein the ability of the compound to upmodulate T cell proliferation or cytokine production at both the low and high antigen concentration identifies the compound as one that upmodulates T cell activation at a both a low and high antigen concentration.

3. The method of claim 1 or 2, wherein T cell proliferation or cytokine production is measured at the low antigen concentration.

4. The method of claim 1 or 2, wherein cytokine production is measured at the high antigen concentration.

5. A method of identifying a compound which overcomes a PD-1-mediated negative signal, comprising:

a) contacting a T cell expressing PD-1 with a test compound at low concentration of antigen to which the T cell is specific in the presence of a costimulatory signal and a PD-1 ligand having the amino acid sequence of SEQ ID NO:2 or SEQ ID NO:5, wherein the low antigen concentration is minimally sufficient to induce T cell proliferation to levels above background in the absence of a PD-1-mediated signal;

b) contacting a T cell expressing PD-1 with a test compound at low concentration of antigen to which the T cell is specific in the presence of a costimulatory signal and in the absence of a PD-1 ligand having the amino acid sequence of SEQ ID NO:2 or SEQ ID NO:5;

c) determining the ability of the test compound to upmodulate T cell proliferation or cytokine production under each condition;

d) comparing the ability of the compound to upmodulate T cell proliferation or cytokine production in the presence and the absence of the PD-1 ligand, wherein the ability of the compound to upmodulate T cell proliferation or cytokine production in the presence of the PD-1 ligand and not in the absence of the PD-1 ligand identifies the compound as one that overcomes a PD-1-mediated negative signal.

6. A method of identifying a compound which overcomes a PD-1-mediated negative signal, comprising:

a) contacting a T cell expressing PD-1 with a test compound and a weak TCR:CD28-mediated signal and a PD-1 ligand having the amino acid sequence of SEQ ID NO:2 or SEQ ID NO:5, wherein the weak TCR:CD28-mediated signal is minimally sufficient to induce T cell proliferation to levels above background in the absence of a PD-1-mediated signal;

b) contacting a T cell expressing PD-1 with a test compound and a weak TCR:CD28-mediated signal in the absence of a PD-1 ligand having the amino acid sequence of SEQ ID NO:2 or SEQ ID NO:5;

c) determining the ability of the test compound to upmodulate T cell proliferation or cytokine production under each condition;

d) comparing the ability of the compound to upmodulate T cell proliferation or cytokine production in the presence and the absence of the PD-1 ligand, wherein the ability of the compound to upmodulate T cell proliferation or cytokine production in the presence of the PD-1 ligand and not in the absence of the PD-1 ligand identifies the compound as one that overcomes a PD-1-mediated negative signal.

7. The method of claim 5 or 6, wherein the cells express high levels of PD-1 and low levels of CD28.

8. The method of claim 5 or 6, wherein the ability of the compound to upmodulate T cell proliferation is measured.

9. The method of claim 5 or 6, wherein the ability of the compound to upmodulate cytokine production is measured.

10. The method of claim 9, wherein upmodulation of cytokine production is indicated by an increase in cytokine mRNA expression.

11. The method of claim 9, wherein the cytokine is a Th1 cytokine.

12. The method of claim 9, wherein the cytokine is a Th2 cytokine.

13. The method of claim 9, wherein the cytokine is selected from the group consisting of IL-2, IL-10 and IFN-y.

* * * * *

UNITED STATES PATENT AND TRADEMARK OFFICE
CERTIFICATE OF CORRECTION

PATENT NO. : 7,432,059 B2  
APPLICATION NO. : 09/895837  
DATED : October 7, 2008  
INVENTOR(S) : Gordon J. Freeman et al.

Page 1 of 1

It is certified that error appears in the above-identified patent and that said Letters Patent is hereby corrected as shown below:

In the Specification

At column 1, line 16, under Government Funding should read:

--This invention was made with government support under AI039671, CA084500, AI041584, AI038310 and AI040614 awarded by the National Institutes of Health. The government has certain rights in the invention.--

Signed and Sealed this
Eighth Day of September, 2015

Michelle K. Lee
*Director of the United States Patent and Trademark Office*